(12) United States Patent
Hill et al.

(10) Patent No.: US 8,771,943 B2
(45) Date of Patent: Jul. 8, 2014

(54) METHOD FOR PREDICTING ATHLETIC PERFORMANCE POTENTIAL

(75) Inventors: Emmeline Hill, Dublin (IE); David MacHugh, Dublin (IE); Nick Orr, Dublin (IE); JingJing Gu, Dublin (IE); Lisa Katz, Dublin (IE)

(73) Assignee: University College Dublin—National University of Ireland, Dublin (IE)

( * ) Notice: Subject to any disclaimer, the term of this patent is extended or adjusted under 35 U.S.C. 154(b) by 21 days.

(21) Appl. No.: 13/063,715

(22) PCT Filed: Sep. 11, 2009

(86) PCT No.: PCT/IE2009/000062
§ 371 (c)(1),
(2), (4) Date: May 27, 2011

(87) PCT Pub. No.: WO2010/029527
PCT Pub. Date: Mar. 18, 2010

(65) Prior Publication Data
US 2011/0223600 A1   Sep. 15, 2011

Related U.S. Application Data

(60) Provisional application No. 61/136,533, filed on Sep. 11, 2008, provisional application No. 61/213,125, filed on May 8, 2009.

(51) Int. Cl.
*C07H 21/04* (2006.01)
*C12Q 1/68* (2006.01)

(52) U.S. Cl.
USPC ......... 435/6.1; 435/6.12; 435/6.13; 435/91.1; 435/91.2; 536/23.1; 536/24.3

(58) Field of Classification Search
None
See application file for complete search history.

(56) References Cited

U.S. PATENT DOCUMENTS

| | | | |
|---|---|---|---|
| 2003/0092019 A1* | 5/2003 | Meyer et al. | 435/6 |
| 2008/0187928 A1 | 8/2008 | Evans et al. | |
| 2011/0262915 A1 | 10/2011 | Hill et al. | |

FOREIGN PATENT DOCUMENTS

| WO | WO 2006/003436 A1 | 1/2006 |
|---|---|---|
| WO | WO 2008/034177 A1 | 3/2008 |

OTHER PUBLICATIONS

Tang (GenBank Accession No. AY840554, Mar. 31, 2005).*
Hill et al. (PLoS One, vol. 5, No. 1, e8645, Jan. 2010).*
Hill et al. (BMC Genomics, vol. 11, No. 552, Oct. 11, 2010).*
Tozaki et al. (Animal Genetics, vol. 43, pp. 42-53, 2011).*
Ioannidis (Nature Genetics, vol. 29, pp. 306-309, Nov. 2001).*
Hirschhorn et al. (Genetics in Medicine. vol. 4, No. 2, pp. 45-61, Mar. 2002).*
Lucentini (The Scientist; 2004, vol. 24, p. 20).*
Ballard et al., "The Mitochondrial Genome: Mutation, Selection and Recombination" *Current Opinion in Genetics & Development*, 11:667-672 (2001).

(Continued)

*Primary Examiner* — Jeanine A Goldberg
(74) *Attorney, Agent, or Firm* — Finnegan, Henderson, Farabow, Garrett & Dunner, LLP

(57) ABSTRACT

A method and assay for predicting athletic performance potential of a subject, such as a thoroughbred race horse, comprising the steps of assaying a biological sample from a subject for the presence of a single nucleotide polymorphism in one or more genes associated with athletic performance. The athletic performance genes may be selected from one or more of MSTN, COX4I2, PDK4, CKM and COX4I1.

25 Claims, 10 Drawing Sheets

(56) References Cited

OTHER PUBLICATIONS

Barrett et al., "Haploview: Analysis and Visualization of LD and Haplotype Maps" *Bioinformatics*, 21(2):263-265 (2005).
Barrett, "Haploview: Visualization and Analysis of SNP Genotype Data" *Cold Spring Harbor Protocols*, 2009, pdb.ip71 [online]. Retrieved from: www.cshprotocols.cshlp.org, pp. 1-3.
Barrey et al., "Heritability of Percentage of Fast Myosin Heavy Chains in Skeletal Muscles and Relationship with Performance" *Equine Veterinary Journal*, 30(Suppl.):289-292 (1999).
Binns et al., "Identification of the Myostatin Locus (*MSTN*) As Having a Major Effect on Optimum Racing Distance in the Thoroughbred Horse in the USA" *Animal Genetics*, 41(Suppl. 2):154-158 (2010).
Blier et al., "National Selection and the Evolution of mtDNA-Encoded Peptides: Evidence for Intergenomic Co-Adaptation" *TRENDS in Genetics*, 17(7):400-406 (2001).
Bray et al., "The Human Gene Map for Performance and Health-Related Fitness Phenotypes: The 2006-2007 Update" *Medicine & Science in Sports & Exercise*, 41(1):34-73 (2008).
Buitrago et al., "The Transcriptional Repressor Nab1 Is a Specific Regulator of Pathological Cardiac Hypertrophy" *Nature Medicine*, 11(8):837-844 (2005).
Burgomaster et al., "Divergent Response of Metabolite Transport Proteins in Human Skeletal Muscle After Sprint Interval Training and Detraining" *Am. J. Physiol. Regul. Integr. Comp. Physiol.*, 292:R1970-R1976 (2007).
Cartharius et al., "MatInspector and Beyond: Promoter Analysis Based on Transcription Factor Binding Sites" *Bioinformatics*, 21(13):2933-2942 (2005).
Clop et al., "A Mutation Creating a Potential Illegitimate MicroRNA Target Site in the Myostatin Gene Affects Muscularity in Sheep" *Nature Genetics*, 38(7):813-818 (2006).
Cunningham et al., "Microsatellite Diversity, Pedigree Relatedness and the Contributions of Founder Lineages to Thoroughbred Horses" *Animal Genetics*, 32:360-364 (2001).
Das, "The Role of Mitochondrial Respiration in Physiological and Evolutionary Adaptation" *BioEssays*, 28:890-901 (2006).
Database EMBL EBI Dbfetch, "Equus caballus MSTN gene, complete cds" [online]: retrieved from www.ebi.ac.uk, Accession No. AY840554, 3 pages (Nov. 14, 2006).
Database NCBI Single Nucleotide Polymorphism (SNP) Cluster Report: rs69276449 [online]; retrieved from www.ncbi.nlm.nih.gov, 2 pages (Aug. 12, 2008).
Database NCBI Single Nucleotide Polymorphism (SNP) Cluster Report: rs68819557 [online]; retrieved from www.ncbi.nlm.nih.gov, 2 pages (Aug. 12, 2008).
Database NCBI Single Nucleotide Polymorphism (SNP) Cluster Report: rs69586789 [online]; retrieved from www.ncbi.nlm.nih.gov, 2 pages (Aug. 12, 2008).
Database NCBI Single Nucleotide Polymorphism (SNP) Cluster Report: rs68518550 [online]; retrieved from www.ncbi.nlm.nih.gov, 2 pages (Aug. 12, 2008).
Dempsey and Wagner, "Exercise-induced Arterial Hypoxemia" *J. Appl. Physiol.*, 87(6):1997-2006 (1999).
Eaton et al, "Maximal accumulated oxygen deficit in thoroughbred horses" *J. Appl. Physiol.*, 78:1564-1568 (1995).
Eivers et al., "Alterations in Oxidative Gene Expression in Equine Skeletal Muscle Following Exercise and Training" *Physiol. Genomics*, 40:83-93 (2010).
Flück, "Functional, Structural and Molecular Plasticity of Mammalian Skeletal Muscle in Response to Exercise Stimuli" *J. Exp. Biol.*, 209:2239-2248 (2006).
Fukuda et al., "HIF-1 Regulates Cytochrome Oxidase Subunits to Optimize Efficiency of Respiration in Hypoxic Cells" *Cell*, 129:111-122 (2007).
Gordon et al., "*Consed*: A Graphical Tool for Sequence?Finishing" *Genome Res.*, 8:195-202 (1998).
Gramkow et al., "Correlation of Race Earnings with Velocity at Maximal Heart Rate During a Field Exercise Test in Thoroughbred Racehorses" *Equine Vet. J.*, 38(Suppl. 36):118-122 (2006).
Grobet et al., "A Deletion in the Bovine Myostatin Gene Causes the Double-Muscled Phenotype in Cattle" *Nature Genetics*, 17:71-74 (1997).
Gu et al., "A Genome Scan for Positive Selection in Thoroughbred Horses" *PLoS ONE* 4(6): e5767, pp. 1-17 (2009).
Gu et al., "Association of Sequence Variants in *CKM* (Creatine Kinase, Muscle) and *COX4I2* (Cytochrome C Oxidase, Subunit 4, Isoform 2) Genes with Racing Performance in Thoroughbred Horses" *Equine Vet. J.*, 42 (Suppl. 38):569-575 (2010).
Gunn, "Muscle, Bone and Fat Proportions and Muscle Distribution of Thoroughbreds and Other Horses" *Equine Exercise Physiology 2*. Davis, CA: ICEEP; pp. 253-264 (1987).
Hallstrom et al., "Balancing the Decision of Cell Proliferation and Cell Fate" *Cell Cycle*, 8(4):532-535 (2009).
Harkins et al., "Effect of Furosemide on Physiologic Variables in Exercising Horses" *Am. J. Vet. Res.*, 54(12):2104-2109 (1993).
Hill et al., "A Genome-Wide SNP-Association Study Confirms a Sequence Variant (g.66493737C>T) in the Equine Myostatin (*MSTN*) Gene as the Most Powerful Predictor of Optimum Racing Distance for Thoroughbred Racehorses" *BMC Genomics*, 11:552 (2010).
Hill et al., "A Sequence Polymorphism in *MSTN* Predicts Sprinting Ability and Racing Stamina in Thoroughbred Horses" *PLoS One*, 5(1):e8645 (2010).
Hill et al., "Moderate and High Intensity Sprint Exercise Induce Differential Responses in *COX4I2* and *PDK4* Gene Expression in Thoroughbred Horse Skeletal Muscle" *Equine Vet. J.*, 42(Suppl. 38):576-581 (2010).
Hill et al., "Targets of Selection in the Thoroughbred Genome Contain Exercise-Relevant Gene SNPs Associated with Elite Racecourse Performance" *Animal Genetics*, 41(Suppl. 2):56-63 (2010).
Hoppeler et al., "Muscle Tissue Adaptations to Hypoxia" *J. Exp. Biol.*, 204:3133-3139 (2001).
International Preliminary Report on Patentability issued by the European Patent Office in International Application No. PCT/IE2009/000062, mailed Mar. 24, 2011.
International Search Report and Written Opinion issued by the European Patent Office in International Application No. PCT/IE2009/000062, mailed Jan. 12, 2010.
Jorgensen et al., "Hypothesis-Driven Candidate Gene Association Studies: Practical Design and Analytical Considerations" *Am. J. Epidemiol.*, 170(8):986-993 (2009).
Joulia, "Mechanisms Involved in the Inhibition of Myoblast Proliferation and Differentiation by Myostatin" *Exp. Cell Res.*, 286:263-275 (2003).
Langley et al., "Myostatin Inhibits Myoblast Differentiation by Down-Regulating MyoD Expression" *J. Biol. Chem.*, 277(51):49831-49840 (2002).
Love et al., "Prevalence, Heritability and Significance of Musculoskeletal Conformational Traits in Thoroughbred Yearlings" *Equine Veterinary Journal*, 38(7):597-603 (2006).
MacArthur et al., "Genes and Human Elite Athletic Performance" *Hum. Genet.*, 116:331-339 (2005).
Matoba et al, "p53 Regulates Mitochondrial Respiration" *Science*, 312:1650-1653 (2006).
McGivney et al., "Transcriptional Adaptations Following Exercise in Thoroughbred Horse Skeletal Muscle Highlights Molecular Mechanisms that Lead to Muscle Hypertrophy" *BMC Genomics*, 9(10):638, p. 1-18 (2009).
McGivney, "Characterization of the Equine Skeletal Muscle Transcriptome Identifies Novel Functional Responses to Exercise Training" *BMC Genomics*, 11:398, p. 1-17 (2010).
McPherron et al., "Double Muscling in Cattle Due to Mutations in the Myostatin Gene" *Proc. Natl. Acad. Sci. USA*, 94:12457-12461 (1997).
McPherron et al., "Regulation of Skeletal Muscle Mass in Mice by a New TGF-β Superfamily Member" *Nature*, 387:83-90 (1997).
Meiklejohn et al., "Positive and Negative Selection on the Mitochondrial Genome" *TRENDS in Genetics*, 23(6):259-263 (2007).
Mosher et al., "A Mutation in the Myostatin Gene Increases Muscle Mass and Enhances Racing Performance in Heterozygote Dogs" *PLoS Genet.*, 3(5):e79, pp. 0779-0786 (2007).

(56) References Cited

OTHER PUBLICATIONS

Park et al., "Molecular Characterization and Mutational Screening of the PRKAG3 Gene in the Horse" *Cytogenet. Genome Res.*, 102:211-216 (2003).
Polager et al., "p53 and E2f: Partners in Life and Death" *Nat. Rev. Cancer*, 9:738-748 (2009).
Purcell et al., "PLINK: A Tool Set for Whole-Genome Association and Population-Based Linkage Analyses" *Am. J. Hum. Genet.*, 81:559-575 (2007).
Revington, "Haematology of the Racing Thoroughbred in Australia 2: Haematological Values Compared to Performance" *Equine Veterinary Journal*, 15(2):145-148 (1983).
Rivero et al., "Effects of intensity and duration of exercise on muscular responses to training of thoroughbred racehorses" *J. Appl. Physiol.*, 102:1871-1882 (2007).
Rivero et al., "Muscle Fiber Type Composition and Fiber Size in Successfully and Unsuccessfully Endurance-Raced Horses" *J. Appl. Physiol.*, 75:1758-1766 (1993).
Rozen et al., "Primer3 on the WWW for General Users and for Biologist Programmers" *Methods in Molecular Biology*, 132:365-386 (2000).
Saleem et al., "Role of p53 in Mitochondrial Biogenesis and Apoptosis in Skeletal Muscle" *Physiol. Genomics*, 37:58-66 (2009).
Sambrook and Russell, *Molecular Cloning—A Laboratory Manual on the Web*. Cold Spring Harbor Laboratory Press, 2001 [online]. Retrieved from www.molecularcloning.com on Feb. 16, 2002.
Schuelke et al., "Myostatin Mutation Associated with Gross Muscle Hypertrophy in a Child" *N. Engl. J. Med.*, 350:2682-2688 (2004).
Seaman et al., "Exercise Induced Ventilation/Perfusion Inequality in the Horse" *Equine Veterinary Journal*, 27(2):104-109 (1995).
Tabor et al., "Candidate-Gene Approaches for Studying Complex Genetic Traits: Practical Considerations" *Nature Reviews, Genetics*, 3:391-397 (May 2002).

Taylor et al., "Therapeutic Targets for Hypoxia-Elicited Pathways" *Pharmaceutical Res.*, 16(10):1498-1505 (1999).
Thiel et al., "The Human Transcriptional Repressor Protein NAB1: Expression and Biological Activity" *Biochimica et Biophysica Acta*, 1493:289-301 (2000).
Thomas et al., "Myostatin, a Negative Regulator of Muscle Growth, Functions by Inhibiting Myoblast Proliferation" *J. Biol. Chem.*, 275(51):40235-40243 (2000).
Tozaki et al., "A Genome-Wide Association Study for Racing Performances in Thoroughbreds Clarifies a Candidate Region Near the *MSTN* Gene" *Animal Genetics*, 41(Suppl. 2):28-35 (2010).
Van Baren et al., "The PCR Suite" *Bioinformatics*, 20(4):591-593 (2004).
Van Deursen et al., "Skeletal Muscles of Mice Deficient in Muscle Creatine Kinase Lack Burst Activity" *Cell*, 74:621-631 (1993).
Wade et al., "Genome Sequence, Comparative Analysis, and Population Genetics of the Domestic Horse" *Science*, 326:865-867 (2009).
Weber et al., "Glucocorticoid Hormone Stimulate Mitochondrial Biogenesis Specifically in Skeletal Muscle" *Endocrinology*, 143:177-184 (2002).
Willliamson et al., "The Inheritance of Speed, Stamina and Other Racing Performance Characters in the Australian Thoroughbred" *J. Anim. Breed. Genet.*, 115:1-16 (1998).
Yang et al., "Improving the Prediction of Complex Diseases by Testing for Multiple Disease-Susceptibility Genes" *Am. J. Hum. Genet.*, 72:636-649 (2003).
Young et al., "Left Ventricular Size and Systolic Function in Thoroughbred Racehorses and Their Relationships to Race Performance" *J. Appl. Physiol.*, 99:1278-1285 (2005).
Zhou et al., "In Silico Detection and Characteristics of Novel microRNA Genes in the Equus Caballus Genome Using an Integrated Ab Initio and Comparative Genomic Approach" *Genomics*, 94:125-131 (2009).

\* cited by examiner

C

D

METHOD FOR PREDICTING ATHLETIC PERFORMANCE POTENTIAL

CROSS REFERENCE TO RELATED APPLICATIONS

This application is a national phase application based on PCT/IE2009/000062, filed Sep. 11, 2009, which claims the benefit of U.S. Provisional Application Nos. 61/136,533, filed Sep. 11, 2008, and 61/213,125, filed May 8, 2009, the contents of all of which are incorporated herein by reference.

The invention relates to a method for predicting the athletic performance potential of a subject.

INTRODUCTION

The Thoroughbred horse industry is a multi-billion euro international industry involved in the breeding, training and racing of Thoroughbred horses. Often multi-million euro decisions are made on the purchase of individual animals with perceived racing potential. The integration of genomics information into the Thoroughbred racing and breeding industries has huge potential for early 'talent identification'. Thoroughbreds are traditionally selected for racing and breeding based on pedigree information as well as numerous phenotypic characteristics. Early identification of genetic potential, by traditional or new means, is paramount to success. Within the industry the quest to find an 'edge' pushes those involved to constantly consider new methods and techniques. Therefore, genomics information has the potential to directly assist breeders and trainers to fine-tune often multi-million dollar decisions by providing previously inaccessible information.

Oxygen is an essential regulator of muscle function, influencing energy production, muscle contraction and removal of by-products. During exercise the requirement for energy is greatly limited by the availability of oxygen. Mammalian cells have evolved elaborate adaptive mechanisms to respond to low cellular oxygen environments (Taylor & Colgan 1999). In studies of human exercise, adaptation to such a hypoxic environment in trained skeletal muscle causes a shift in substrate selection to increased oxidation of carbohydrates and stimulates cells to improve conditions for oxygen transport and utilisation (Hoppeler & Vogt 2001). In Thoroughbred horses, despite a number of structural and functional adaptations in the cardiovascular and respiratory systems that improve oxygen carrying capacity and delivery during high-intensity short-duration exercise, the oxygen transport system lags far behind peripheral demand reflected in the routine development of an exercise-induced arterial hypoxemia and hypercapnia (Dempsey & Wagner, 1999; Seaman, 1995). The Thoroughbred response is extreme in comparison to other animal species, including trained human athletes, reflecting the enormous requirement of the musculature for energy. Remarkably, even faced with a limited oxygen supply, Thoroughbreds remain elite athletes exquisitely adapted to extreme exercise.

Thoroughbred horses excel in both sprint (<1 mile) and longer distance (>1 mile) races. The physiological requirements for these disciplines differ and are regulated by the partitioning of metabolic pathways. During the first 75 seconds of exercise at supramaximal intensities (105-125% $VO_2max$) horses experience an oxygen deficit because oxygen supply cannot meet the demand of exercising muscles (Dempsey & Wagner, 1999; Seaman, 1995). Despite this, it has been estimated that during sprint races (<1000 m) approximately 70% of the total energy will be supplied aerobically. Horses competing over longer distances and for longer duration (>75 seconds) reach steady-state $VO_2$ and therefore are not oxygen deficient.

A range of approaches has been taken to investigate measurable associations with athletic performance phenotype in Thoroughbred racehorses including assessment of heart size (Young et al 2005), muscle fibre type (Rivero et al. 2007) musculoskeletal conformation (Love et al 2006), speed at maximum heart rate (Gramkow & Evans 2006), haematological (Revington 1983) and other physiological variables (Harkins et al 1993).

WO2006003436 describes the association between performance and gene variants encoded by the mitochondrial genome. However, mitochondrial DNA (mtDNA) haplotypes are inherited strictly from the maternal parent and therefore relate solely to female contributions to the phenotype. As there is a limited number of mtDNA haplotypes (n=17) in the Thoroughbred population and just 10 females contribute to 74% of present maternal lineages (Cunningham et al 2002) it is unlikely that these haplotype variants have a significant effect as the favourable haplotypes would become 'fixed' quickly in a population where there is targeted selection for performance; in addition, the effective population size (of mtDNA variants) is one third of nuclear-encoded variants (Ballard and Dean 2001, Blier et al 2001, Das 2006, Meiklejohn et al 2007). Also, mtDNA haplotypes can be directly inferred from pedigree information.

It is an object of the invention to provide a method for predicting the athletic performance potential of a subject that overcomes some of these problems.

STATEMENTS OF INVENTION

This invention provides DNA-based tests for detecting variation in nuclear-encoded genes. This approach is a superior to mitochondrial DNA (mtDNA) testing because variation in nuclear encoded genes reflects inheritance of favourable gene variants from all possible ancestors whereas mtDNA testing is restricted to female ancestry.

The methods and assays described herein are performed ex vivo and can be considered to be ex vivo or in vitro methods and assays.

Any suitable biological sample which contains genetic material for example, blood, saliva, hair, skin, bone marrow, soft tissue, internal organs, biopsy sample, semen, skeletal muscle tissue and the like, may be used as a biological sample for the methods described herein. Blood and hair samples are particularly suitable as a biological sample.

"Athletic performance" as used herein includes racing such as competitive racing and equestrian sports such as racing, showjumping, eventing, dressage, endurance events, riding, hunting and the like. The equestrian sports may be competitive sports.

Competitive racing species include equines (horses), camels, dogs, elephants, hares, kangaroos, ostriches, pigeons, Homo sapiens and birds of prey such as hawks or falcons. The competitive racing species may be a Thoroughbred race horse or a showjumping horse.

By "primer" we mean a nucleic acid sequence containing between about 15 to about 40 for example between about 18 to about 25 contiguous nucleotides from a nucleic acid sequence of interest. The primer may be a forward (5' or 3') or reverse (3' to 5') primer or a primer designed on a complementary nucleic acid sequence to the sequence of interest. In the present invention, the sequence of interest is the genomic sequence of a gene associated with athletic performance, for example a gene listed in the appendices or one or more of the COX4I1, COX4I2, PDK4, CKM or MSTN genes. In one embodiment, the primer may comprise between about 15 to about 40 for example between about 18 to about 25 contiguous nucleotides from SEQ ID No. 1, SEQ ID No. 2, SEQ ID No. 3, SEQ ID No. 31 or SEQ ID No. 32 or between about 15 to about 40 for example between about 18 to about 25 contiguous nucleotides from a complementary sequence to SEQ ID No. 1, SEQ ID No. 2, SEQ ID No. 3, SEQ ID No. 31 or SEQ ID No. 32. By "complementary sequence" we mean a sequence that binds to the sequence of interest using conventional Watson-Crick base pairing i.e. adenine binds to thymine and cytosine binds to guanine.

The invention provides single nucleotide polymorphisms (SNPs) that are associated with elite athletic performance. The invention provides a method of predicting the athletic performance of a subject comprising the step of assaying a biological sample from the subject for the presence of a single nucleotide polymorphism (SNP) in one or more of the genes listed in the appendices wherein the SNP has a significant association with athletic performance.

According to the invention there is provided a method for predicting the athletic performance potential of a subject comprising the step of assaying a biological sample from a subject for the presence of a single nucleotide polymorphism (SNP) in one or more of the MSTN gene, COX4I2 gene, PDK4 gene, CKM gene or COX4I1 gene.

The SNP may be MSTN__66493737 (T/C). The presence of a C allele is indicative of elite athletic performance. The presence of a homozygous CC genotype may indicative of elite athletic performance. The elite athletic performance may be elite sprinting performance The SNP may be COX4I2__22684390 (C/T). The presence of a T allele may be indicative of elite athletic performance. The presence of a homozygous TT genotype may be indicative of elite athletic performance.

The SNP may be PDK4__38973231 (A/G). The presence of an A allele may be indicative of elite athletic performance. The presence of a homozygous AA genotype may be indicative of elite athletic performance.

The SNP may be CKM__15884567 (G/A). The presence of an A allele may be indicative of elite athletic performance. The presence of a homozygous AA genotype may be indicative of elite athletic performance.

The SNP may be COX4I1__32772871 (T/C). The presence of a T allele may be indicative of elite athletic performance. The presence of a homozygous TT genotype may be indicative of elite athletic performance.

The biological sample of the subject may be selected from the group comprising: blood, saliva, skeletal muscle, skin, semen, biopsy, bone marrow, soft tissue, internal organs and hair.

The subject may be from a competitive racing species. The subject may be an equine such as a Thoroughbred race horse.

The invention further provides an assay for determining the athletic performance potential of a subject comprising the steps of:
    obtaining a sample;
    extracting or releasing DNA from the sample; and
    identifying a single nucleotide polymorphism (SNP) in a target sequence from a gene associated with athletic performance in the extracted or released DNA
wherein the athletic performance potential of a subject is associated with the SNP.

The gene associated with athletic performance may be selected from one or more of MSTN, COX4I2, PDK4, CKM or COX4I1.

The assay may comprise the step of:
    amplifying a target sequence from a gene associated with athletic performance in the extracted or released DNA prior to the step of identifying a single nucleotide polymorphism.

The DNA may be genomic DNA

The invention further provides an assay for use in determining the athletic performance potential of a subject comprising means for detecting the presence of a single nucleotide polymorphism (SNP) in one or more of the MSTN gene, COX4I2 gene, PDK4 gene, CKM gene or COX4I1 gene.

The SNP may be MSTN__66493737 (T/C). The presence of a C allele is indicative of elite athletic performance. The presence of a homozygous CC genotype may indicative of elite athletic performance. The elite athletic performance may be elite sprinting performance.

The SNP may be COX4I2__22684390 (C/T). The presence of a T allele may be indicative of elite athletic performance. The presence of a homozygous TT genotype may be indicative of elite athletic performance.

The SNP may be PDK4__38973231 (A/G). The presence of an A allele may be indicative of elite athletic performance. The presence of a homozygous AA genotype may be indicative of elite athletic performance.

The SNP may be CKM__15884567 (G/A). The presence of an A allele may be indicative of elite athletic performance. The presence of a homozygous AA genotype may be indicative of elite athletic performance.

The SNP may be COX4I1__32772871 (T/C). The presence of a T allele may be indicative of elite athletic performance. The presence of a homozygous TT genotype may be indicative of elite athletic performance.

The invention also provides an assay for determining the athletic potential of a subject comprising the step of:
    obtaining a sample;
    extracting or releasing DNA from the sample;
    identifying the genotype of the MSTN__66493737 (T/C) SNP in the extracted or released DNA
wherein the presence of a C allele in the MSTN__66493737 (T/C) SNP is indicative of elite athletic performance.

The assay may comprise the step of:
    amplifying a target sequence encoding the MSTN__66493737 (T/C) SNP in the extracted or released DNA prior to the step of identifying the genotype of the MSTN__66493737 (T/C) SNP.

The presence of a homozygous CC genotype indicative of elite athletic performance.

The elite athletic performance may be elite sprinting performance.

The DNA may be genomic DNA.

The sample from the subject may be selected from the group comprising: blood, saliva, skeletal muscle skin, bone marrow, biopsy, soft tissue, semen, internal organ and hair.

The subject may be from a competitive racing species. The subject may be an equine such as a Thoroughbred race horse.

We have also shown that homozygous carriers of the T allele of the COX4I2 gene (EquCab2.0 22676361-C/T) single nucleotide polymorphism (SNP), i.e. those that have the polymorphism in both alleles of the COX4I2 gene, are statistically more likely to be elite sprinting racehorses compared to subjects that are heterozygous for the SNP. i.e. subjects that have the polymorphism in one of the alleles of the COX4I2 gene, or subjects that do not have the SNP in either allele of the COX4I2 gene.

We describe a method of predicting athletic performance of a subject comprising the step of assaying a biological sample from the subject for the presence or absence of a single nucleotide polymorphism (SNP) in the COX4I2 gene. The SNP may be EquCab 2.0 COX4I2-22676361-C/T. The presence of a homozygous TT genotype may be indicative of elite athletic performance. The presence of a homozygous TT genotype may be indicative of elite aerobic performance. The presence of a homozygous TT genotype may be indicative of elite sprinting performance. The biological sample of the subject may be selected from the group comprising: blood, saliva, skeletal muscle, semen, biopsy, internal organ, skin, bone marrow (or any other biological tissue) and hair. The subject may be from a competitive racing species. The subject may be an equine. The subject may be a Thoroughbred race horse.

We also describe an assay for use in determining athletic performance of a subject comprising means for detecting the presence or absence of a single nucleotide polymorphism (SNP) in the COX4I2 gene. The SNP may be EquCab 2.0 COX4I2-22676361-C/T. The presence of a homozygous TT genotype may be indicative of elite athletic performance. The biological sample of the subject may be selected from the group comprising: blood, saliva, skeletal muscle, semen, biopsy, internal organ, skin, bone marrow (or any other biological tissue) and hair. The subject may be from a competitive racing species. The subject may be an equine. The subject may be a Thoroughbred race horse.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION

Figure 1:
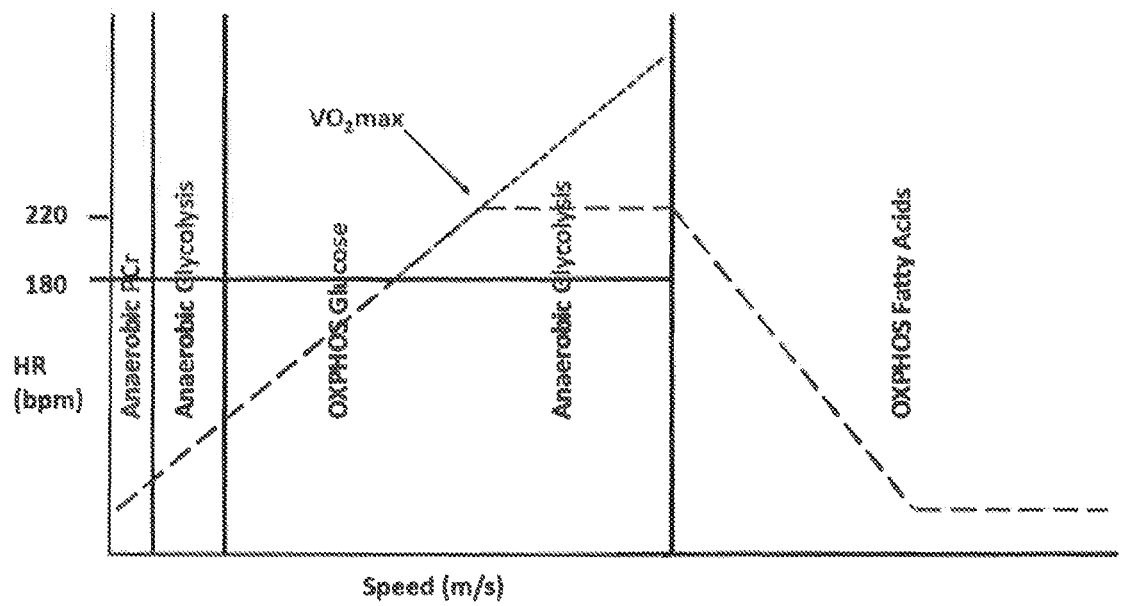
FIG. 1 is a schematic of the partitioning of energy during exercise in horses.

Intense selection for elite racing performance in the Thoroughbred horse (*Equus caballus*) has resulted in a number of adaptive physiological phenotypes relevant to exercise, however the underlying molecular mechanisms responsible for these characteristics are not well understood.

Eivers et al (2009) investigated adaptive changes in mRNA expression in equine skeletal muscle for a panel of candidate exercise-response genes following a standardised incremental-step treadmill exercise test in eight unconditioned Thoroughbred horses. In the study, biopsy samples were obtained from the gluteus medius pre-exercise ($T_0$), immediately post-exercise ($T_1$) and four hours post-exercise ($T_2$). They detected significant (P<0.05) fold differences relative to $T_0$ in eight genes (CKM, COX4I1, COX4I2, PDK4, PPARGC1A, PRKAA1, SLC2A1, and SLC2A4) at $T_2$. By studying the relationships between mRNA and velocity at maximum heart rate ($VHR_{max}$) and peak post-exercise plasma lactate concentration ($[La]T_1$), they demonstrated significant (P<0.05) associations with COX4I1 and PPARCG1A at $T_2$ and between $[La]T_1$, and COX4I1 at $T_0$. In a follow-on study they investigated gene expression changes in a second cohort of horses after a ten month period of conditioning. They showed that in resting samples, the COX4I1 gene had a significant increase in abundance following conditioning and, after exercise in the conditioned cohort, significant fold differences were identified in COX4I2, PDK4 and PPARGC1A at $T_2$. They also detected significant relationships with $VHR_{max}$ and $[La]T_1$ for PPARGC1A and COX4I1.

The present invention relates to a previously unknown relationship between sequence variants (such as SNPs) in a number of candidate exercise response genes (listed in the appendices) and retrospective athletic performance (given as racecourse success i.e. Group winner or non-winner, handicap rating (RPR) and best race distance for Group winners) in Thoroughbred race horses. In some aspects, the invention relates to SNPs in the COX4I1, COX4I2, PDK4, CKM and MSTN genes.

COX4I1 and COX4I2

Cytochrome C oxidase (COX) is a multi-subunit enzyme (Complex IV) that catalyzes the electron transfer from reduced cytochrome C to oxygen in mitochondrial respiration. COX is a dimer in which each monomer is made up of 13 subunits, three of which are encoded by the mitochondrial genome (COX1, 2 and 3). Nuclear encoded COX4 is responsible for the regulation and assembly of mitochondrially encoded subunits on the inner mitochondrial membrane (Fukuda et al. 2007). In human skeletal muscle, COX4 mRNA levels have been shown to be associated with mitochondrial volume and, by extension, $VO_{2max}$. COX4 comprises two isoforms (COX4-1 and COX4-2) encoded by the COX4I1 and COX4I2 genes that are differentially regulated in normoxic and hypoxic environments (Fukuda et al. 2007). In normal oxygen environments COX4I1 is preferentially transcribed. In limited oxygen environments HIF-1 activates transcription of COX4I2 and the mitochondrial LON gene. As LON inhibits the expression of COX4I1, these control mechanisms result in increased COX4I2 transcription and protein synthesis and decreased COX4-1 availability. This mechanism has been postulated to be a strategy to maximise the efficiency of cellular respiration in limited oxygen environments (Fukuda et al. 2007).

The physiological requirements during a race differ depending on the energy demand and are regulated by the partitioning of metabolic pathways to provide energy in the most efficient manner. During the first 75 seconds of exercise at supramaximal intensities (105-125% $VO_{2max}$) horses experience an oxygen deficit because oxygen supply cannot meet the demand of exercising muscles (Dempsey and Wagner 1999; Seaman et al. 1995). Over longer distances and for longer duration (>75 seconds) horses reach steady-state $VO_2$ and rely principally on aerobic metabolism. At the end of a race anaerobic demand increases as horses pass the 'lactate threshold'. During short distance races (<1,000 m) approximately 70% of the total energy in the form of ATP, necessary for muscle contraction, is generated by aerobic metabolic pathways (Eaton et al. 1995). In Thoroughbred horses exercising at supramaximal intensities over short distances this hypoxic environment may trigger the well-conserved metabolic switch from COX4-1 to COX4-2 utilisation (Fukuda et al. 2007). This environmental regulation of COX4-2 may increase the efficiency of cellular respiration. COX4-2 may therefore be an important regulator of energy supply in the early stages of a race and towards the end of a race when oxygen is limited. As can be seen from FIG. 1, large amounts of energy are required while peripheral physiological systems (i.e. skeletal muscle) are operating in limited oxygen environments in the early stages of exercise and towards the end of a race. Generation of energy via COX4-2 may be important during both these stages.

It has been suggested that regulation of mitochondrial biogenesis may be mediated by glucocorticoid hormone (Weber et al 2002). The COX4I2 gene contains a glucocorticoid receptor element (TGTT) which may be targeted to increase COX4-2 expression and therefore increase mitochondrial volume. Also, the COX4I2 gene contains a p53 tumor suppressor binding site (CATG). Recent studies have suggested that p53 may play a role in regulation of mitochondrial biogenesis and aerobic metabolism via COX (Matoba et al. 2006; Saleem et al. 2009).

CKM

Creatine kinase (CK), also known as creatine phosphokinase (CPK) or phosphocreatine kinase, is an enzyme (EC 2.7.3.2) expressed by various tissue types. It catalyses the conversion of creatine and consumes adenosine triphosphate (ATP) to create phosphocreatine and adenosine diphosphate (ADP). In tissues that consume ATP rapidly, especially skeletal muscle, but also brain and smooth muscle, phosphocreatine serves as an energy reservoir for the rapid regeneration of ATP. Thus creatine kinase is an important enzyme in such tissues.

In most cells the CK enzyme consists of two subunits, which can be either B (brain type) or M (muscle type). There are, therefore, three different isoenzymes: CK-MM, CK-BB and CK-MB. The genes for these subunits are located on different chromosomes. In addition, there are two mitochondrial creatine kinases, the ubiquitous and sarcomeric form. The different types of CK isoenzymes are listed in Table 1.

TABLE 1

| Isoenzymes of creatine kinase | |
|---|---|
| gene | protein |
| CKB | creatine kinase, brain |
| CKBE | creatine kinase, ectopic expression |
| CKM | creatine kinase, muscle |
| CKMT1A | creatine kinase, mitochondrial 1A |
| CKMT1B | creatine kinase, mitochondrial 1B |
| CKMT2 | creatine kinase, mitochondrial 2 (sarcomeric) |

Isoenzyme patterns differ depending on tissue type. For example, CK-BB occurs mainly in brain tissues, and its levels rarely have any significance in skeletal muscle. Skeletal muscle expresses CK-MM (98%) and low levels of CK-MB (1%) whereas in contrast the myocardium (heart muscle) expresses CK-MM at about 70% and CK-MB at 25-30%.

The mitochondrial creatine kinase ($CK_m$), which produces ATP from ADP by converting creatine phosphate to creatine, is present in the mitochondrial intermembrane space. Apart from the mitochondrial form, there are three forms present in the cytosol—$CK_a$ (in times of acute need, produces ATP in the cytosol at the cost of creatine phosphate), $CK_c$ (maintains critical concentration of creatine and creatine phosphate in the cytosol by coupling their phosphorylation and dephosphorylation respectively with ATP and ADP) and $CK_g$ (which couples direct phosphorylation of creatine to the glycolytic pathway.

The creatine kinase, muscle gene (CKM) encodes a muscle type isozyme of creatine kinase found exclusively in striated muscle. The encoded protein is involved in cellular energetics. During exercise CKM gene knockout mice show a lack of burst activity but maintain normal absolute muscle force (van Deursen et al. 1993). We have found that CKM gene transcripts are the most abundant transcripts in the Thoroughbred horse skeletal muscle transcriptome, supporting the pivotal role played by the CKM gene in exercise adaptation in the horse.

PDK4

The regulation of glucose utilisation is tightly controlled by the uptake of glucose by glucose transporters, the rate of glycolytic flux and the conversion of pyruvate to acetyl-CoA in mitochondria via the catalytic function of the pyruvate dehydrogenase complex (PDC). The critical rate limiting step in the oxidation of glucose is the regulation of assembly of the PDC which is controlled by pyruvate dehydrogenase kinase (PDK). PDK blocks the formation of the PDC resulting in the beta-oxidation of fatty acids to acetyl-CoA as the substrate for oxidative phosphorylation. Three genes (PDK2, PDK3 and PDK4) of the four genes that encode PDK isoforms are located in positively selected genomic regions in Thoroughbred (Gu et al 2009). The PDK4 gene promoter contains a binding site for the FOXO1A transcription factor, a key regulator of insulin signalling in liver and adipose tissue. Single nucleotide polymorphisms in FOXO1A have been found to have a protective effect on T2DM development and related phenotypes in humans. FOXO1A has also been found among positively selected genomic regions in Thoroughbred and its PDK4 promoter binding site sequence is conserved in horse. The transcription factors FOXO1 and SMAD have also been shown to be responsible for myostatin (MSTN) gene regulation and therefore play key roles in the regulation of muscle growth.

In a genome scan for positive selection, Gu et al (2009) detected a region that deviated very significantly from neutral expectations in two independent statistical tests ($F_{ST}$ and Ewens-Watterson test). This region contained the PDK4 gene. PDK4 gene expression is co-ordinated by the transcriptional co-activator PGC-1α via ERRα (estrogen-related receptor alpha) binding. PGC-1α, encoded by the PPARGC1A (peroxisome proliferator-activated receptor gamma, coactivator 1 alpha) gene, is a key regulator of energy metabolism that regulates insulin sensitivity by controlling glucose transport via SLC2A4 (solute carrier family 2 (facilitated glucose transporter), member 4; previously GLUT4) and drives the formation of oxidative muscle fibres and co-ordinates mitochondrial biogenesis via its interaction with nuclear encoded mitochondrial protein genes.

MSTN

Myostatin is also known as growth/differentiation factor 8 precursor (GDF-8). In several mammalian species (including cattle, sheep and dogs), the double muscling trait is caused by mutations in the myostatin (MSTN) gene. In dogs, MSTN gene mutations in racing whippets have been associated with the 'bully' phenotype and heterozygous individuals are significantly faster than individuals carrying the wild-type genotype (Mosher et al 2007). Mutations in the MSTN gene may be associated with athletic power.

We have analysed a number of single nucleotide polymorphisms (SNPs) in genes associated with athletic performance and have developed a simple DNA based method of predicting the athletic performance potential of a subject based on the SNPs.

The invention will be more clearly understood from the following examples.

EXAMPLES

Subjects

A Thoroughbred is a registered racehorse that can trace its ancestry to one of three foundation stallions and the approximately 30 foundation mares entered in The General Studbook, 1791 (Weatherby and Sons 1791). There are two types of Thoroughbred race: National Hunt races are run over hurdles or steeplechase fences over distances of up to 4.5 miles (7,200 m), while Flat races have no obstacles and are run over distances ranging from five furlongs (⅝ mile or 1,006 m) to 20 furlongs (4,024 m). The highest standard and most valuable elite Flat races are known as Group (Europe and Australasia) or Stakes races (North America). The most prestigious of these races include The Breeders' Cup races (United States), The Kentucky Derby (United States), The Epsom Derby (United Kingdom) et cetera.

Three hundred and fifty Group races are run in Europe (Britain, Ireland (incl. Northern Ireland), France, Germany, Italy) annually including 84 Group 1, 93 Group 2 and 173 Group 3 races. In the United Kingdom and Ireland 196 Group races are competed annually (43 Group 1, 50 Group 2 and 103 Group 3). Britain has the highest number of Group races (139) in Europe per annum, with 57% run over distances ≤1 mile (1609 meters) and 43% run over distances >1 mile. Australia has approximately 540-550 Group races per season from a total of almost 21,000 races and New Zealand hosts 78 Group races per season. After Group races, Listed races are the next highest grade of race.

Horses that compete over distances ≤1 mile are known as 'sprinters' whereas horses that compete over distances >1 mile are known as 'stayers'. Horses competing in 1 mile races ('milers' and 'middle distance') may be considered either sprinters or stayers and the way in which a race is executed by the rider often reflects the trainers perceived ability ('sprinter' or 'stayer') of the horse. The International Federation of Horseracing Authorities recognizes five race distance categories: Sprint (5-6.5 f, ≤1,300 m), Mile (6.51-9.49 f, 1,301-1,900 m), Intermediate (9.5-10.5 f, 1,901-2,112 m), Long (10.51-13.5 f, 2,114-2,716 m) and Extended (>13.51 f, >2,717 m); S-M-I-L-E [Note: 1 furlong=⅛ mile=201.2 meters].

To minimise confounding effects of racing over obstacles only horses with performance records in Flat races were considered for inclusion in the study cohorts. In all cases pedigree information was used to control for genetic background by exclusion of samples sharing relatives within two generations. Also, overrepresentation of popular sires within the pedigrees was avoided where possible.

Samples from Thoroughbred horses were collected with informed owner's consent from racing, breeding and sales establishments in Ireland, Britain and New Zealand during 1997-2006. All horses were categorized based on retrospective racecourse performance records as "elite Thoroughbreds" (TBE) or "other Thoroughbreds" (TBO). Elite Thoroughbreds were flat race horses that had won at least one Group (Group 1, Group 2 or Group 3) race. Other Thoroughbreds were those that had competed on the racetrack but had never won a flat race or had a handicap rating (Racing Post Racing (RPR)) of less than 89.

Example 1

COX4I2

During sprint exercise, energy in the form of ATP, necessary for muscle contraction, is generated principally by aerobic metabolic pathways (70% aerobic, 30% anaerobic) albeit in a limited oxygen environment. We suggest that this relative hypoxic environment triggers the well-conserved metabolic switch from COX4-1 to COX4-2 thereby increasing the efficiency of cellular respiration. COX4-2 is therefore an important regulator of energy supply during sprinting, but not necessarily in longer distance competitions where oxygen demands are met. This switch is mediated by the transcription factor HIF-1α in the cell that has been well-characterised as the master regulator of hypoxia-dependent gene expression (Semenza 1998). HIF-1α activates the transcription of genes encoding PDK1, LDHA, COX4-2 and LON and controls the switch from COX4-1 to COX4-2. In Thoroughbred muscle that is deprived of oxygen during intense exercise an enhanced response to reduced oxygen and the ability to generate ATP in the most efficient manner will provide a significant advantage to that individual.

Also, increased mitochondrial volume has been shown to be associated with higher aerobic capacity (Fluck 2006). Increased amount of glucocorticoid hormone has been shown to stimulate mitochondrial biogenesis, either by specifically targeting the mitochondrial genome or by an unknown mechanism (Weber et al 2002). Glucorticoid receptor elements (Glucocorticoid responsive and related elements) contain the recognition sequence (TGTT). The COX4I2 gene contains one of these elements in Intron 2. Therefore glucocorticoid binding may stimulate increased gene expression leading to increased mitochondrial volume and therefore aerobic energy capacity.

In some aspects, the present invention relates to a single nucleotide polymorphism (SNP) in COX4I2 that is significantly ($P<0.01$) associated with elite sprinting performance. The significant association of the COX4I2 homozygous TT genotype (EquCab2.0 22676361-C/T) in elite sprint race winners may be utilized in DNA-based tests of genetic potential for elite athletic performance in Thoroughbred horses.

Precise Location of the COX4I2 Gene (EquCab2.0 22676361-C/T) Polymorphism

The exact location of the COX4I2 polymorphism is on *Equus caballus* chromosome 22 at position 22676361 of the Horse Genome Sequence (*Equus caballus* Version 0.2.0) which can be viewed at www.broad.mit.edu/mammals/horse/. The COX4I2 polymorphism may be identified as EquCab2.0 COX4I2__22676361 (C/T) SNP.

The horse genome EquCab2 assembly is a Whole Genome Shotgun (WGS) assembly at 6.79× and was released in September 2007. A female Thoroughbred named "Twilight" was selected as the representative horse for genome sequencing. The project coordination and genome sequencing and assembly is provided by the Broad Institute. The N50 size is the length such that 50% of the assembled genome lies in blocks of the N50 size or longer. The N50 size of the contigs is 112.38 kb, and the total length of all contigs is 2.43 Gb. When the gaps between contigs in scaffolds are included, the total span of the assembly is 2.68 Gb. The horse EquCab2 was annotated using a standard Ensembl mammalian pipeline. Predictions from vertebrate mammals as well as horse proteins have been given priority over predictions from non-vertebrate mammals. The set of predictions has been compared to 1:1 homologues genes in human and mouse, and missing homologs in the horse annotation have been recovered using exonerate. Horse and human cDNAs have been used to add UTRs to protein based predictions. The final gene-set comprises 20,737 protein-coding genes, 2,863 identified as pseudogenes and 1,580 classified as retro-transposed genes.

Genotyping of the EquCab2.0 COX4I2-22676361-C/T Polymorphism

Genotyping of SNPs was conducted in a sample of Thoroughbreds (n=149) comprising both elite (n=79) and non-elite performers (n=70). The elite performer group contained a subset of animals (n=70) that competed preferentially in short distance (≤1 mile; n=34) and long distance (>1 mile; n=36) races.

Genomic DNA was extracted from either fresh whole blood or hair samples. Blood samples were collected in 7 ml Vacutainer K$_3$EDTA blood collection tubes (Becton Dickinson, Franklin Lakes, N.J.). Hair samples with visible hair roots were collected in labelled, airtight zip-lock bags. Samples were stored at 4° C. prior to DNA extraction using a modified version of a standard phenol/chloroform method (Sambrook and Russell 2001). DNA concentrations for all samples were estimated using a NanoDrop ND-1000 UV-Vis Spectrophotometer (NanoDrop Technologies, Wilmington, Del.).

The flanking sequence and SNP (bold and square brackets) is as follows; (bases indicated in lower case indicate that the sequence read was not optimal for this region of the flanking sequence)

```
                                              (SEQ. ID No. 1)
caagagtggagtgtgctccaagaactggaggctagcatgtagcagagga ggcagtagcagaggaggagaggttgatgggggagctgcatttggagagt ctggcaggcaggaccttgaatgccaggctaaggagtttATTGGGAGGCA

AGTGGGTGCTGATAAAGGCTCAAGGATTCCATCAGGCTGTTCCCACAAA

GACC[C/T]GGGCCACCTCAGGGCACCATATCCCCATATCCAGGAGCCA

GTTGTGTCCCAGAGAAAACAAGGGACTGGACCTTGAGACTTGGCCAGTG

TCCTTCACATCCTACCCTGTGCACGCCCTGTTTGGCCTGTGGTGCAGA

AGGCCCCTGGGAGACCTGAAGCAGAAGCTGCAGACCATTCCAGGTTAGT

GTGGAGCCCCAGA
```

Genotyping of the COX4I2 gene was performed by KBiosciences (www.kbioscience.co.uk) using either competitive allele specific PCR (KASPar) or Taqman (Applied Biosystems). KASPar is a proprietary in house homogeneous fluorescent genotyping system.

25 μL of total DNA was supplied to KBiosciences at a concentration of 15 ng/μL in "v-bottomed" 96 well microtitre plates. Also included were a number of samples for set-up and assay validation (n=24) and blank (n=1 per 96 well plate) samples to check for reproducibility and to control for errors in sample handling Genetic Analysis Study Following genotyping, a genetic analysis was carried out on the subjects (n=149) described above.

Individual dichotomous logistic regression models were fitted for each SNP. Genotype trend effects were modeled by estimating the risk associated with a linear trend in magnitude of effect relative to the common homozygote, heterozygote, and rare homozygote genotypes. P-values were determined from a likelihood ratio test statistic and approximated according to an asymptotic $\chi^2$ distribution with one degree of freedom. The best genetic model for significantly associated SNPs was determined by repeating the analysis with coding variables for additive, recessive and overdominant models.

Table 2 shows the EquCab2.0 COX4I2__22676361 (C/T) SNP genotype frequencies amongst the subjects.

| Elite sprinters (less than 8 furlongs) (n = 39) Vs Other elite race winners (n = 36) | | | | |
|---|---|---|---|---|
| | Sp (<8 f) vs En | | | |
| Genotype | OR | lower | upper | p-value |
| dominant (CC v CT-TT) | 1.77 | 0.55 | 5.76 | 3.37E-01 |
| recessive (CC-CT v TT) | 4.89 | 1.21 | 19.75 | 1.56E-02* |
| over-dominant (CC-TT v CT) | 0.56 | 0.2 | 1.52 | 2.50E-01 |

| Elite sprinters (less than 7 furlongs) (n = 28) Vs Other elite race winners (n = 36) | | | | |
|---|---|---|---|---|
| | Sp (<7 f) vs En | | | |
| Genotype | OR | lower | upper | p-value |
| dominant (CC v CT-TT) | 2.05 | 0.54 | 7.69 | 2.78E-01 |
| recessive (CC-CT v TT) | 5.6 | 1.31 | 23.86 | 1.25E-02* |
| over-dominant (CC-TT v CT) | 0.53 | 0.18 | 1.57 | 2.53E-01 |

Figure 2:
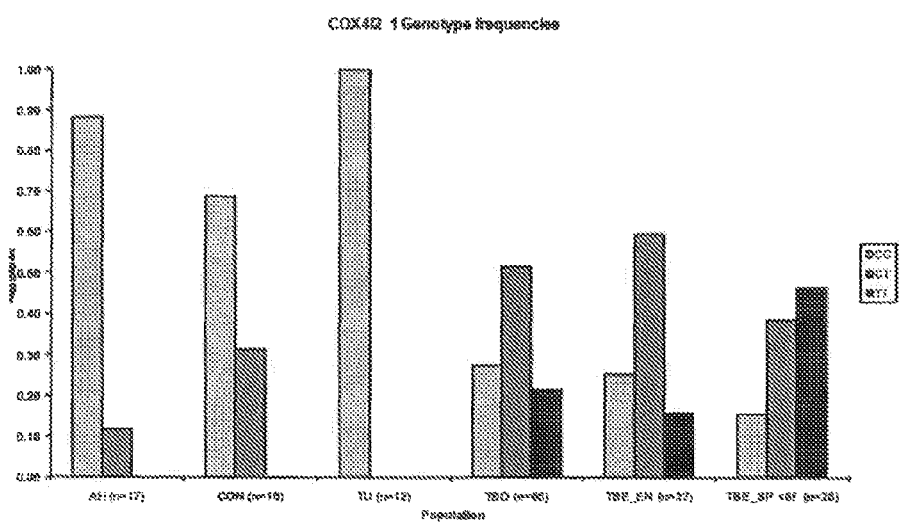
FIG. 2 is a bar chart showing the distribution of COX4I2 22676361 (C/T) SNP genotypes in Thoroughbred subpopulations (TBE_EN: elite performing Thoroughbreds over distances >8f; TBE_SP: elite performing Thoroughbreds over distances <8f; TBO: other Thoroughbreds that have raced but have never won a race and have a handicap rating <70) and in non-Thoroughbred horses (AH: Akhal-Teke; CON: Connemara Pony; TU: Tuva). Elite Thoroughbreds that have successfully competed over distances <8f have a significantly higher frequency of the TT genotype than other Thoroughbred sub-populations and non-Thoroughbreds.

Wherein:
Sp = sprinter
En = endurance (or 'stayer')
OR = Odds ration
Lower = lower confidence interval
upper = upper confirdence interval Referring to Table 2 the EquCab2.0 COX4I2__22676361 (C/T) SNP homozygote TT genotype is significantly associated with elite racing (sprinting) performance over distances <8 furlongs (less than 1 mile) (P<0.02) (FIG. 2) and this association is more pronounced over distances <7f (P<0.01).

Thoroughbred horses carrying the homozygote T allele (TT) of the COX4I2__22676361 (C/T) SNP have a greater sprinting ability compared to Thoroughbred horses carrying the heterozygous T allele (TC) or to Thoroughbred horses that do not carry the T allele (CC). Therefore, the sprinting performance of a Thoroughbred horse can be predicted by testing a biological sample for the presence or absence of the homozygote T allele of the COX4I2__22676361 (C/T) SNP.

Example 2

Genes Associated with Thoroughbred Racing Performance

We investigated associations between 80 SNPs in the following genes: ACN9, ACSS1, ACTA1, ACTN2, ADHFE1, GGPS1, GSN, MC3R, MTFR1, NDUFA8, PDK4, PON1, PTGS1, PTPN1, TNC, TOMM20, UGCG CKM, COX4I2, COX4I1, HIF1A, MYEF2, and PRKAA1 (details of the SNPs are given in the appendices with racing performance in Thoroughbreds).

The present invention identifies significant associations between SNPs and athletic performance phenotypes in a set of these genes including ACN9, ACSSJ, ACTN2, ADHFE1, CKM, COX4I2, GSN, MSTN, PON1, PTGS1 and PTPN1 (see the appendices). Because of the known gene expression response to exercise in equine skeletal muscle (Eivers et al 2009) and evidence for association with performance in dogs (Mosher et at 2008) and response to training, four of the genes (CKM, COX4I2, PDK4 and MSTN) that had a significant association with Thoroughbred racing performance were investigated in detail. SNPs in three of those genes (CKM, COX4I2 and PDK4) are associated with elite (Group race winning) performance and a SNP in the MSTN gene is associated with elite sprint race performance.

In this example, the following sample set was used:

TABLE 3

Details of samples included in each subpopulation.

| Sample Set B | n | No. sires | No. Gr race winners | Mean RPR | Range RPR | Total no. races | Mean no. races | No. races won | No. Gr races won | No. Gr 1 races won | Mean no. Gr races won |
|---|---|---|---|---|---|---|---|---|---|---|---|
| TB | 148 | 136 | | | | | | | | | |
| TBE | 86 | 86 | 84 | 115 | 87-134 | 1170 | 13.8 | 425 | 215 | 91 | 2.5 |
| TBO | 62 | 62 | 0 | 59 | 21-89 | 537 | 8.7 | 15 | 0 | 0 | 0 |

In which TB is Thoroughbred, TBE is Elite Group race winning Thoroughbred; and TBO is non-elite (i.e other non-winning) Thoroughbred. The TBE cohort was further subdivided into TBE_sprinter (n = 39) and TBE_endurance or 'stayer' (n = 32).

Genetic Analysis Study

Tests for association of SNPs with athletic performance were performed using the program PLINK (http://pngu.mgh-.harvard.edu/purcell/plink/ Purcell et al., 2007)

Standard Case/Control Association Analysis

To perform a standard case/control association analysis, the option: plink—file mydata—assoc was used, which generates a file plink.assoc containing the fields:

| | |
|---|---|
| CHR | Chromosome |
| SNP | SNP ID |
| BP | Physical position (base-pair) |
| A1 | Minor allele name (based on whole sample) |
| F_A | Frequency of this allele in cases |
| F_U | Frequency of this allele in controls |
| A2 | Major allele name |
| CHISQ | Basic allelic test chi-square (1df) |
| P | Asymptotic p-value for this test |
| OR | Estimated odds ratio (for A1) |

Association Analysis

It is possible to perform tests of association between a disease and a variant other than the basic allelic test (which compares frequencies of alleles in cases versus controls), by using the—model option. The tests offered here are (in addition to the basic allelic test):

Cochran-Armitage trend test
Genotypic (2 df) test
Dominant gene action (1df) test
Recessive gene action (1df) test One advantage of the Cochran-Armitage test is that it does not assume Hardy-Weinberg equilibrium, as the individual, not the allele, is the unit of analysis (although the permutation-based empirical p-values from the basic allelic test also have this property). SNPs showing severe deviations from Hardy-Weinberg are often likely to be bad SNPs, or reflect stratification in the sample, however, and so are probably best excluded in many cases.

The genotypic test provides a general test of association in the 2-by-3 table of disease-by-genotype. The dominant and recessive models are tests for the minor allele (which is the minor allele can be found in the output of either the—assoc or the—freq commands. That is, if D is the minor allele (and d is the major allele):

Allelic: D versus d
Dominant: (DD, Dd) versus dd
Recessive: DD versus (Dd, dd)
Genotypic: DD versus Dd versus dd As mentioned above, these tests are generated with option plink—file mydata—model which generates a file plink-.model containing the following fields:

| | |
|---|---|
| CHR | Chromosome number |
| SNP | SNP identifier |
| TEST | Type of test |
| AFF | Genotypes/alleles in cases |
| UNAFF | Genotypes/alleles in controls |
| CHISQ | Chi-squated statistic |
| DF | Degrees of freedom for test |
| P | Asymptotic p-value |

Each SNP will feature on five rows of the output, corresponding to the five tests applied. The column TEST refers to either ALLELIC, TREND, GENO, DOM or REC, referring to the different types of test mentioned above. The genotypic or allelic counts are given for cases and controls separately. For recessive and dominant tests, the counts represent the genotypes, with two of the classes pooled.

These tests only consider diploid genotypes: that is, for the X chromosome males will be excluded even from the ALLELIC test. This way the same data are used for the five tests presented here. Note that, in contrast, the basic association commands (—assoc and—linear, etc) include single male X chromosomes, and so the results may differ.

The genotypic and dominant/recessive tests will only be conducted if there is a minimum number of observations per cell in the 2-by-3 table: by default, if at least one of the cells has a frequency less than 5, then the alternate tests are skipped (NA is written in the results file). The Cochran-Armitage and allelic tests are performed in all cases. This threshold can be altered with the—cell option: plink—file mydata—model—cell 20

Results of the association tests are provided in full in the appendices. A number of SNPs in the four genes PDK4, COX4I2, CKM and MSTN were investigated. For each gene we selected the SNP with the most significant association (P value) (Table 4) for the trait for further investigation. The 4 SNPs with greatest association with athletic performance were PDK4_38973231-A/G, COX4I2_22684390-C/T, CKM_15884567-G/A, and MSTN_66493737-T/C. SNPs in PDK4, CKM and COX4I2 were associated with elite (Group race winning) performance and a SNP in MSTN was associated with elite sprinting performance in Thoroughbred racehorses. The best fit genotypic models were assigned based on the results in Table 5 below.

The best fit genotypic models were assigned based on the results in Table 5. The best model for association of the SNPs with athletic performance was concluded as follows:

PDK4—Allelic→A allele is preferred i.e. AA or AG
CKM—Allelic→A allele is preferred i.e. AA or AG
COX4I2—Recessive→T allele is preferred i.e. TT
MSTN—Genotypic→Genotype predicts distance category. (in the cohort used in this example, none of the 'stayers' were CC but 50% sprinters were CC)

Figure 4A:
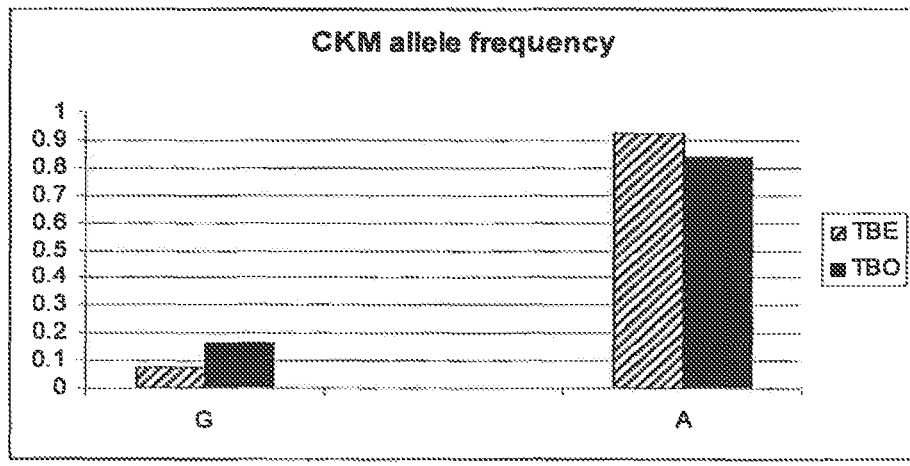
FIGS. 4 (A) to (D) are graphs showing the allele frequency distribution among elite (hatched bar) and non-elite Thoroughbreds for CKM 22684390 (C/T) SNP (A), COX4I2 22684390 (C/T) SNP (B) and PDK4 38973231 (A/G) SNP (C) and among elite sprinters (hatched bar) and elite endurance Thoroughbreds for MSTN 66493737 (T/C) SNP (D)
Figure 4B:
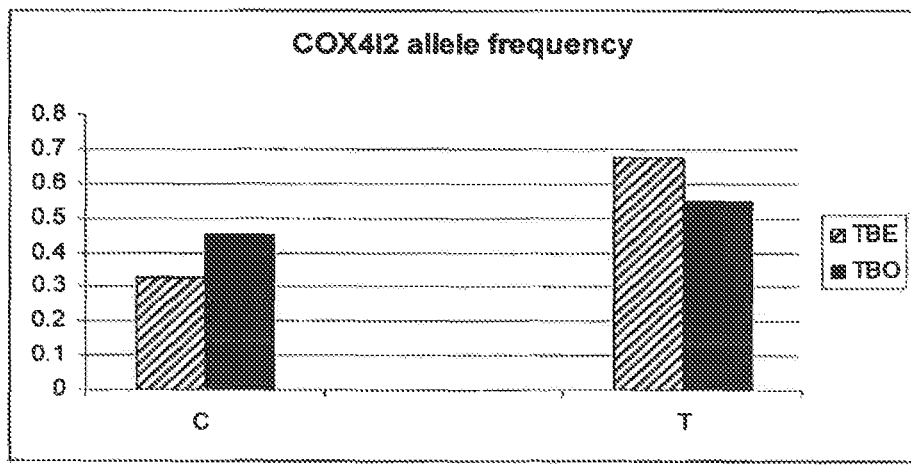
Figure 4:
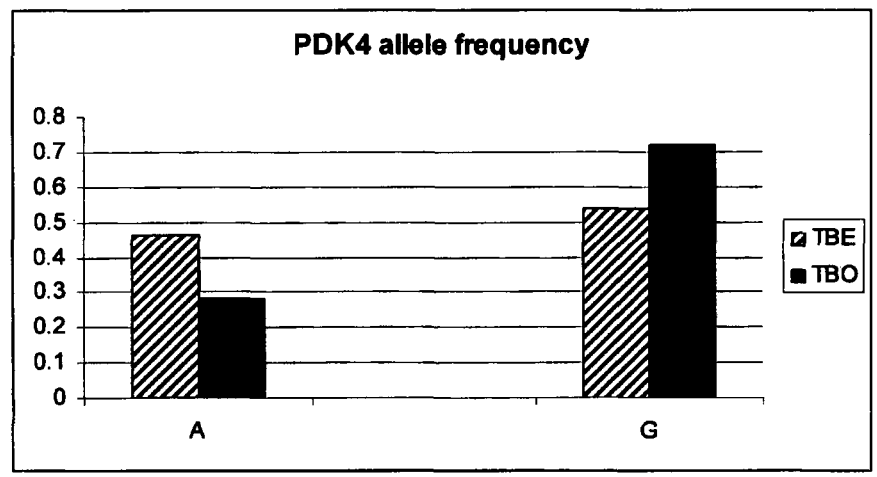
Figure 4:
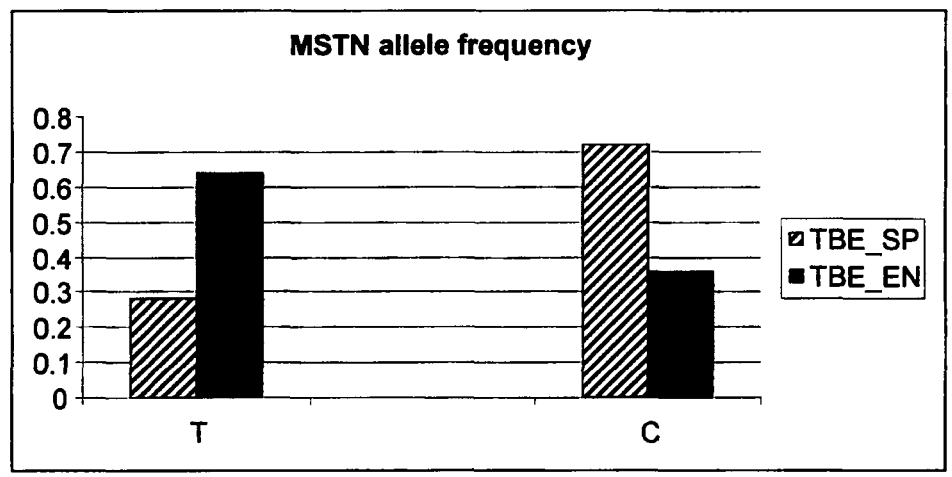
Figure 5A:
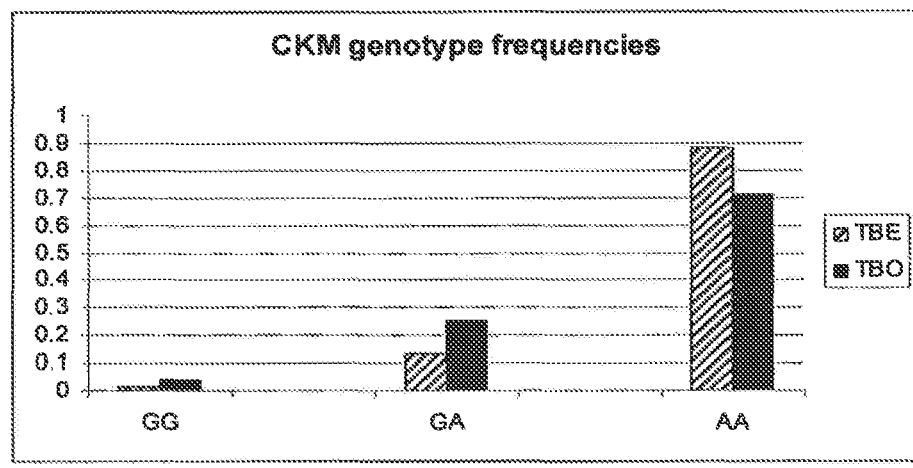
FIGS. 5 (A) to (D) are graphs showing the genotype frequency distributions among elite (hatched bar) and non-elite Thoroughbreds for CKM 22684390 (C/T) SNP (A), COX4I2 22684390 (C/T) SNP (B) and PDK4 38973231 (A/G) SNP (C) and among elite sprinters (hatched bar) and elite endurance Thoroughbreds for MSTN 66493737 (T/C) SNP (D)
Figure 5B:
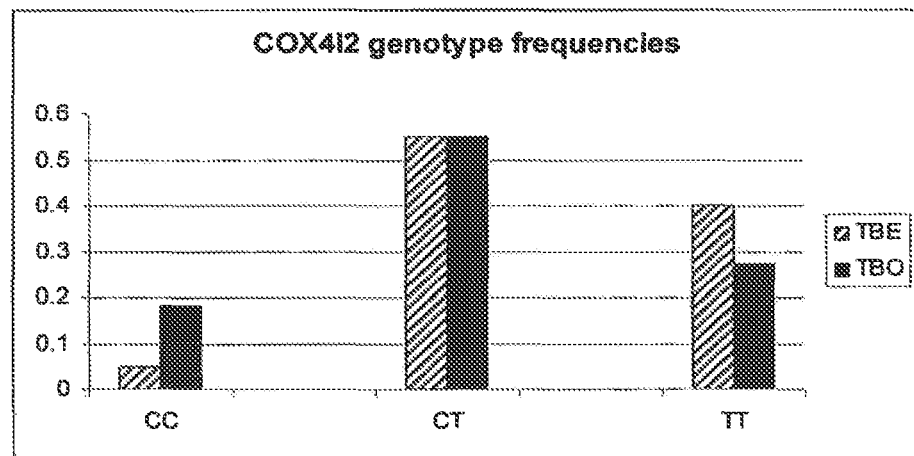
Figure 5C:
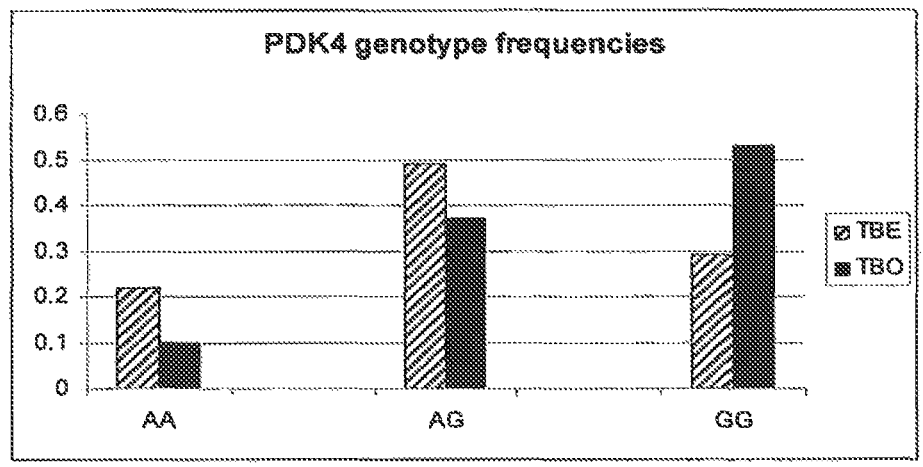
Figure 5D:
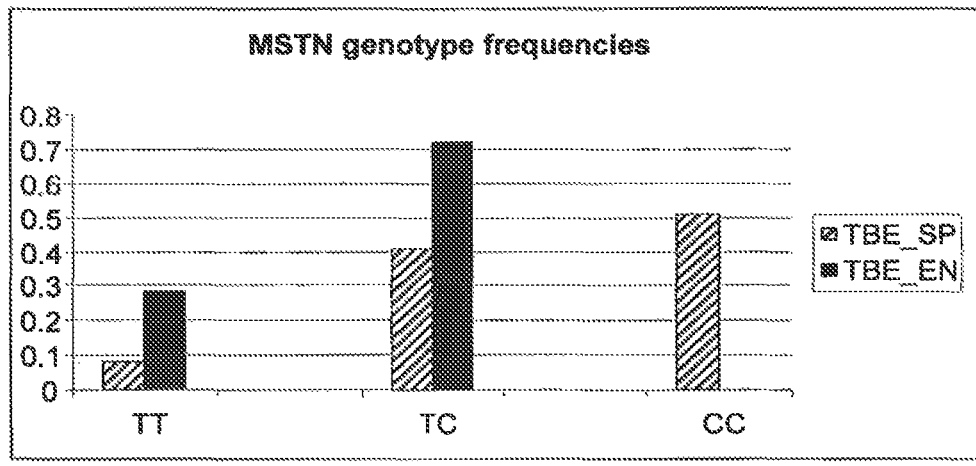

The allele frequency distributions among Elite and Non-elite Thoroughbreds for CKM, COX4I2 and PDK4 and among Elite Sprinters and Elite Endurance for MSTN are shown in FIG. 4. Table 6 below shows the allele frequencies for the four SNPs in Thoroughbreds (TBE and TBO).

TABLE 4

Results of SNP association tests for elite (Group winning) performance (PDK4, CKM and COX4I2) and elite sprinting performance (MSTN) in Thoroughbred racehorses. SNPs with the most significant association in each gene are shown here.

| CHR | SNP | BP | A1 | A2 | F_A(A1) | F_A(A2) | F_U(A1) | F_U(A2) | CHISQ | P | OR |
|---|---|---|---|---|---|---|---|---|---|---|---|
| 4 | PDK4_38973231 | 3924 | A | G | 0.464 | 0.536 | 0.282 | 0.718 | 9.874 | 0.001676 | 2.2 |
| 10 | CKM_15884567 | 2716 | G | A | 0.074 | 0.926 | 0.164 | 0.836 | 5.355 | 0.02066 | 0.4089 |
| 22 | COX4I2_22684390 | 1164 | C | T | 0.325 | 0.675 | 0.455 | 0.546 | 4.654 | 0.03098 | 0.5778 |
| 18 | MSTN_66493737 | 212 | T | C | 0.282 | 0.718 | 0.641 | 0.359 | 18.31 | 1.88E−05 | 4.5 |

In which A1: allele 1; A2: Allele 2; F_A(A1): frequency of allele 1 in elite TB (PDK4, CKM and COX4I2) and elite sprinters (MSTN); F_A(A2): frequency of allele 2 in elite TB (PDK4, CKM and COX4I2) and elite sprinters (MSTN); F_U(A1): frequency of allele 1 in non-elite TB (PDK4, CKM and COX4I2) and elite endurance (MSTN); F_U(A2): frequency of allele 2 in non-elite TB (PDK4, CKM and COX4I2) and elite endurance (MSTN).

The SNPs that were chosen for further investigation were as follows:

PDK4_38973231 (A/G)
COX4I2_22684390 (C/T)
CKM_15884567 (G/A)
MSTN_66493737 (T/C)

TABLE 5

Association test results for best-fit model

| CHR | SNP | A1 | A2 | TEST | AFF | UNAFF | CHISQ | DF | P |
|---|---|---|---|---|---|---|---|---|---|
| 4 | PDK4_38973231 | A | G | GENO | 18/41/24 | 6/23/33 | 9.644 | 2 | 0.008049 |
| 4 | PDK4_38973231 | A | G | TREND | 77/89 | 35/89 | 9.237 | 1 | 0.002372 |
| 4 | PDK4_38973231 | A | G | ALLELIC | 77/89 | 35/89 | 9.874 | 1 | 0.001676 |
| 4 | PDK4_38973231 | A | G | DOM | 59/24 | 29/33 | 8.791 | 1 | 0.003027 |
| 4 | PDK4_38973231 | A | G | REC | 18/65 | 6/56 | 3.706 | 1 | 0.05422 |
| 22 | COX4I2_22684390 | C | T | GENO | 4/44/32 | 10/30/15 | 6.979 | 2 | 0.03052 |
| 22 | COX4I2_22684390 | C | T | TREND | 52/108 | 50/60 | 5.58 | 1 | 0.01817 |
| 22 | COX4I2_22684390 | C | T | ALLELIC | 52/108 | 50/60 | 4.654 | 1 | 0.03098 |
| 22 | COX4I2_22684390 | C | T | DOM | 48/32 | 40/15 | 2.326 | 1 | 0.1272 |
| 22 | COX4I2_22684390 | C | T | REC | 4/76 | 10/45 | 6.093 | 1 | 0.01357 |
| 10 | CKM_15884567 | G | A | GENO | 1/10/70 | 2/14/39 | 5.03 | 2 | 0.08087 |
| 10 | CKM_15884567 | G | A | TREND | 12/150 | 18/92 | 4.865 | 1 | 0.02741 |
| 10 | CKM_15884567 | G | A | ALLELIC | 12/150 | 18/92 | 5.355 | 1 | 0.02066 |
| 10 | CKM_15884567 | G | A | DOM | 11/70 | 16/39 | 4.953 | 1 | 0.02605 |
| 10 | CKM_15884567 | G | A | REC | 1/80 | 2/53 | 0.876 | 1 | 0.3493 |
| 18 | MSTN_66493737 | T | C | GENO | 3/16/20 | 9/23/0 | 23.8 | 2 | 0.000006799 |
| 18 | MSTN_66493737 | T | C | TREND | 22/56 | 41/23 | 20.64 | 1 | 0.000005545 |
| 18 | MSTN_66493737 | T | C | ALLELIC | 22/56 | 41/23 | 18.31 | 1 | 0.00001875 |
| 18 | MSTN_66493737 | T | C | DOM | 19/20 | 32/0 | 22.85 | 1 | 0.000001755 |
| 18 | MSTN_66493737 | T | C | REC | 3/36 | 9/23 | 5.225 | 1 | 0.02226 |

TABLE 6

Allele frequencies for the four SNPs in Thoroughbreds (TBE and TBO)

| CHR | SNP | A1 | A2 | MAF | NCHROBS |
|---|---|---|---|---|---|
| 4 | PDK4_38973231 | A | G | 0.3862 | 290 |
| 10 | CKM_15884567 | G | A | 0.1103 | 272 |

TABLE 6-continued

Allele frequencies for the four SNPs in Thoroughbreds (TBE and TBO)

| CHR | SNP | A1 | A2 | MAF | NCHROBS |
|---|---|---|---|---|---|
| 22 | COX4I2_22684390 | C | T | 0.3778 | 270 |
| 18 | MSTN_66493737 | T | C | 0.4353 | 278 |

In which MAF is Minor Allele Frequency and NCHROBS Number of Chromosomes analysed.

The genotype frequency distributions among Elite and Non-elite Thoroughbreds for the SNPs in CKM, COX4I2 and PDK4 and among Elite Sprinters and Elite Endurance for the SNP in MSTN. The results of this study are shown in FIG. 5 and Table 7 below.

TABLE 7

Genotype frequencies in elite and non-elite Thoroughbred sub-populations for SNPs: PDK4 (PDK4_38973231); COX4I2 (COX4I2_22684390); CKM (CKM_15884567) and in elite sprinters and elite endurance Thoroughbreds for SNP: MSTN (MSTN_66493737).

|  |  | AA | AG | GG |  | AA | AG | GG |
|---|---|---|---|---|---|---|---|---|
| PDK4 | ALL | 24 | 64 | 57 | 145 | 0.17 | 0.44 | 0.39 |
|  | TBE | 18 | 41 | 24 | 83 | 0.22 | 0.49 | 0.29 |
|  | TBO | 6 | 23 | 33 | 62 | 0.10 | 0.37 | 0.53 |

|  |  | CC | CT | TT |  | CC | CT | TT |
|---|---|---|---|---|---|---|---|---|
| COX4I2 | ALL | 14 | 74 | 47 | 135 | 0.10 | 0.55 | 0.35 |
|  | TBE | 4 | 44 | 32 | 80 | 0.05 | 0.55 | 0.40 |
|  | TBO | 10 | 30 | 15 | 55 | 0.18 | 0.55 | 0.27 |

|  |  | GG | GA | AA |  | GG | GA | AA |
|---|---|---|---|---|---|---|---|---|
| CKM | ALL | 3 | 24 | 109 | 136 | 0.02 | 0.18 | 0.80 |
|  | TBE | 1 | 10 | 70 | 80 | 0.01 | 0.13 | 0.88 |
|  | TBO | 2 | 14 | 39 | 55 | 0.04 | 0.25 | 0.71 |

|  |  | TT | TC | CC |  | TT | TC | CC |
|---|---|---|---|---|---|---|---|---|
| MSTN | ALL | 23 | 75 | 41 | 139 | 0.17 | 0.54 | 0.29 |
|  | TBE_SP | 3 | 16 | 20 | 39 | 0.08 | 0.41 | 0.51 |
|  | TBE_EN | 9 | 23 | 0 | 32 | 0.28 | 0.72 | 0.00 |

Deviations from Hardy-Weinberg equilibrium (HWE) for the four SNPs in the sample cohort were investigated to determine departure from expected neutral genetic drift. Deviation from HWE may be an indicator of selection and may alter the expected distribution of genotypes in a population given the allele frequencies. This information is required to correctly assign genotype frequencies to enable the test for performance.

Deviation from HWE was identified in COX4I2_22684390-C/T in the Elite Thoroughbred sub-population Thus genotype frequencies may be adjusted in the test to account for the over-representation of the TT genotype among elite racehorses. Also, deviation from HWE was identified in MSTN_66493737-T/C in the elite endurance Thoroughbred cohort. Thus genotype frequencies may be adjusted in the test to account for the under-representation of the CC genotype among elite endurance racehorses.

Example 3

A Multi-Gene Prediction Test for Elite (Group Race Winning) Performance in Thoroughbred Horses The present invention provides a simple DNA based method (genotypic test) for predicting the athletic performance of a thoroughbred race horse based on the presence or absence of a SNP in one or more exercise response gene. The exercise response gene may be one or more of the genes listed in the appendices. For example the genotypic test may be based on a SNP in one or more of the PDK4, CKM, COX4I2, COX4I1, MSTN, ACSS1, ACTN2 or PTGS1 genes. Details of some of the SNPs that may be used to predict the athletic performance of a thoroughbred horse are given in the appendices. It will be appreciated that the genotypic test may be based on a combination of any one or more of these SNPs.

Figure 3:
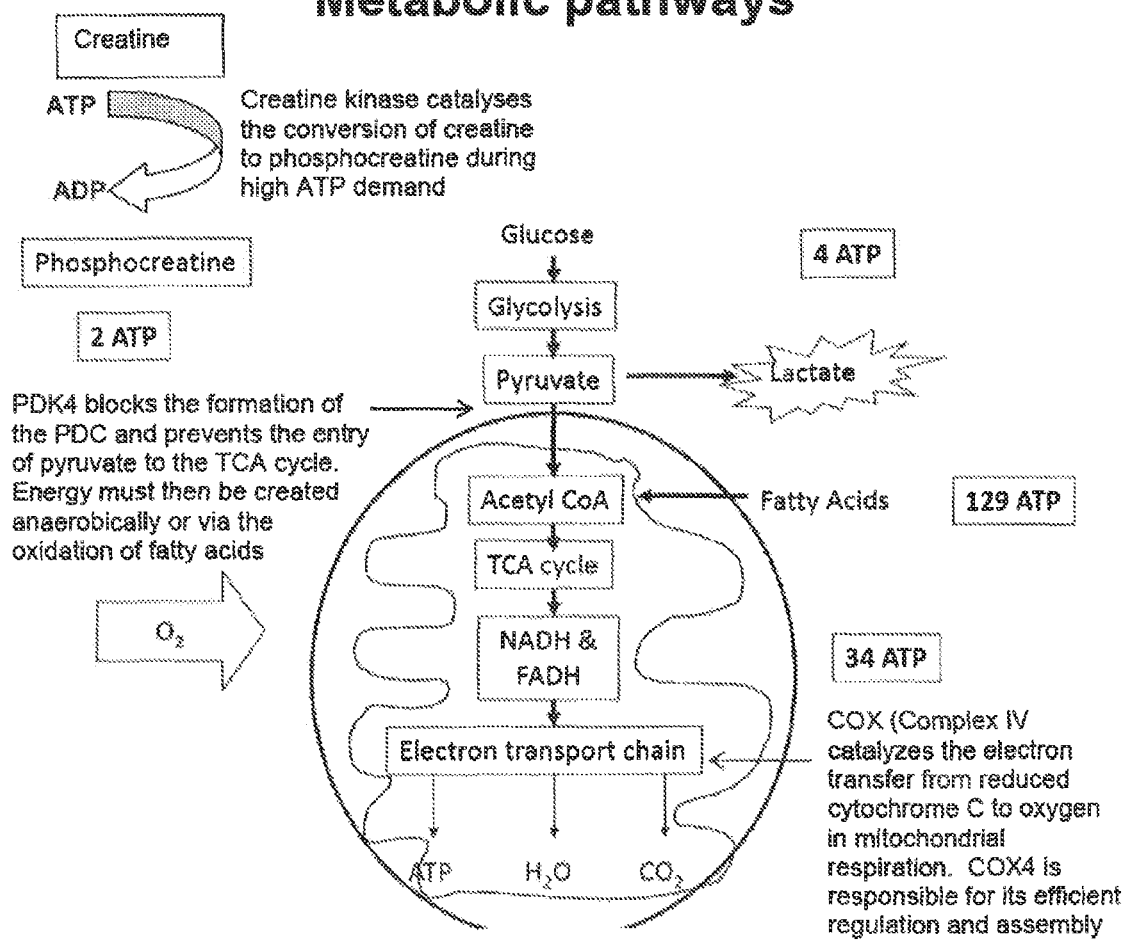
FIG. 3 is a schematic showing the relationship between three of the main metabolic pathways contributing to energy production during exercise, the function of three genes CKM, COX4I2 and PDK4 associated with elite racing performance are shown.

Referring to FIG. 3, the three main metabolic pathways contributing to energy production during exercise and the location in the pathways and the function of three genes (CKM, COX4I2 and PDK4) associated with elite racing performance are shown. Using knowledge of known function, the knowledge that the genes are expressed in skeletal muscle in response to exercise and the results in Example 2 above, in this non-limiting example, we developed a simple DNA based genotypic test for predicting elite performance in Thoroughbred horses based on SNPs in the PDK4, COX4I2 and CKM genes.

COX4I2 SNP (COX4I2_22684390 (C/T) SNP)

This SNP is located on Chromosome 22 of *Equus caballus* at position 22,684,390 bp forward strand of the Horse Genome Sequence (*Equus caballus* Version 2.0) which can be viewed at www.broad.mit.edu/mammals/horse/.

The horse genome EquCab2 assembly is a Whole Genome Shotgun (WGS) assembly at 6.79× and was released in September 2007. A female Thoroughbred named "Twilight" was selected as the representative horse for genome sequencing. The project coordination and genome sequencing and assembly is provided by the Broad Institute. The N50 size is the

TABLE 8

Tests for deviations from Hardy-Weinberg equilibrium in ALL (All TB); AFF (Elite and elite sprinters); UNAFF (non-elite and elite endurance).

| CHR | SNP | TEST | A1 | A2 | GENO | O(HET) | E(HET) | P |
|---|---|---|---|---|---|---|---|---|
| 4 | PDK4_38973231 | ALL | A | G | 24/64/57 | 0.4414 | 0.4741 | 0.3872 |
| 4 | PDK4_38973231 | AFF | A | G | 18/41/24 | 0.494 | 0.4974 | 1 |
| 4 | PDK4_38973231 | UNAFF | A | G | 6/23/33 | 0.371 | 0.4052 | 0.5332 |
| 10 | CKM_15884567 | ALL | G | A | 3/24/109 | 0.1765 | 0.1963 | 0.2033 |
| 10 | CKM_15884567 | AFF | G | A | 1/10/70 | 0.1235 | 0.1372 | 0.3553 |
| 10 | CKM_15884567 | UNAFF | G | A | 2/14/39 | 0.2545 | 0.2737 | 0.6188 |
| 22 | COX4I2_22684390 | ALL | C | T | 14/74/47 | 0.5481 | 0.4701 | 0.06812 |
| 22 | COX4I2_22684390 | AFF | C | T | 4/44/32 | 0.55 | 0.4388 | 0.03941 |
| 22 | COX4I2_22684390 | UNAFF | C | T | 10/30/15 | 0.5455 | 0.4959 | 0.5891 |
| 18 | MSTN_66493737 | ALL | T | C | 23/75/41 | 0.5396 | 0.4916 | 0.3022 |
| 18 | MSTN_66493737 | AFF | T | C | 3/16/20 | 0.4103 | 0.405 | 1 |
| 18 | MSTN_66493737 | UNAFF | T | C | 9/23/0 | 0.7188 | 0.4604 | 0.001815 | length such that 50% of the assembled genome lies in blocks of the N50 size or longer. The N50 size of the contigs is 112.38 kb, and the total length of all contigs is 2.43 Gb. When the gaps between contigs in scaffolds are included, the total span of the assembly is 2.68 Gb. The horse EquCab2 was annotated using a standard Ensembl mammalian pipeline. Predictions from vertebrate mammals as well as horse proteins have been given priority over predictions from non-vertebrate mammals. The set of predictions was been compared to 1:1 homologues genes in human and mouse, and missing homologs in the horse annotation have been recovered using exonerate. Horse and human cDNAs have been used to add UTRs to protein based predictions. The final gene-set comprises 20,737 protein-coding genes, 2,863 identified as pseudogenes and 1,580 classified as retro-transposed genes.

Further details of the SNP are as follows:
SNP: COX4I2_22684390 (C/T) P=0.03098 OR=0.5778
EquCab2.0 SNP_ID: BIEC2-617568
Genomic location of SNP: Intron 2
Substitution type: Transition
The SNP disrupts a glucocorticoid response element (GRE) binding site (C/TGTT). The favourable allele (T) retains the site (TGTT), therefore enabling GRE binding and increasing expression of the gene. The less favourable allele (C) disrupts the site (CGTT), therefore disabling GRE binding and not increasing expression of the gene. Alternatively, the SNP disrupts a p53 tumor suppressor binding site (CAC/TG). The favourable allele (T) retains the site (CATG), therefore enabling p53 binding and contributing to mitochondrial biogenesis. The less favourable allele (C) disrupts the site (CACG) therefore disabling the p53 binding and not contributing to mitochondrial biogenesis.

The flanking sequence and SNP (bold and square brackets) is as follows:

(SEQ ID No. 2)
GCTGGGCGATCCTGGGGACATAAAAGTGAATCACCTGGATGGTTCTTGC

CCTCAGGGTGCTCCCAGTCCAGTGGGGGAACCAACACAAGCCCAGATAA

CTGTAATATAGGATATGTGGCGAGGGTGAAGTGTGTTCAAGGGGCTGTG

AGGACCCAAAGGAGAGAGAGATGAAATCCTGGTGGGCCTTCCAGAGGAG

GGCA[T/C]GTTCTAGTTGACCTTGAATGGTGAGGCTGAGGGTGCTGCC

AGGTGGTGGGAACAGCATGGGTAAGGGTATGGGAGCGGAAGAGCATGGA

GGGTCCTAGGCATCAGTAAGTGCTGTAGGGGAAGGAACAGAGAGAGGCG

GTGAGGTGGCCAGGAAAGAAGGGGGCCTGACCCTGGGGAGCAGGAGGGA

TGTGTGACTCCAA

CKMSNP (CKM_15884567 (G/A) SNP)

This SNP is located on Chromosome 10 of *Equus caballus* at position 15,884,567 bp of the Horse Genome Sequence (*Equus caballus* Version 2.0) which can be viewed at www.broad.mit.edu/mammals/horse/.

The horse genome EquCab2 assembly is a Whole Genome Shotgun (WGS) assembly at 6.79× and was released in September 2007. A female Thoroughbred named "Twilight" was selected as the representative horse for genome sequencing. The project coordination and genome sequencing and assembly is provided by the Broad Institute. The N50 size is the length such that 50% of the assembled genome lies in blocks of the N50 size or longer. The N50 size of the contigs is 112.38 kb, and the total length of all contigs is 2.43 Gb. When the gaps between contigs in scaffolds are included, the total span of the assembly is 2.68 Gb. The horse EquCab2 was annotated using a standard Ensembl mammalian pipeline. Predictions from vertebrate mammals as well as horse proteins have been given priority over predictions from non-vertebrate mammals. The set of predictions was been compared to 1:1 homologues genes in human and mouse, and missing homologs in the horse annotation have been recovered using exonerate. Horse and human cDNAs have been used to add UTRs to protein based predictions. The final gene-set comprises 20,737 protein-coding genes, 2,863 identified as pseudogenes and 1,580 classified as retro-transposed genes.

Further details of the SNP are as follows:
SNP: CKM_15884567 (G/A) P=0.02066 OR=0.4089
EquCab2.0 SNP_ID: BIEC2-109575
Genomic location of SNP: Intron 4
Substitution type: Transition
The SNP disrupts an Interferon regulatory factor binding site (GCA/GA). The A allele retains the site (GCAA). The G allele disrupts the site (GCGA).

The flanking sequence and SNP (bold and square brackets) is as follows:

(SEQ ID No. 3)
CTGTCCCTAACAGACCTGGACCTTGGCCCCGTGGAGGTCCTAAAGGCRA

CTATACGCGATGTAAACCCAAATTCATGACATCCCCTGAAGCATGCTCT

TCCCCTGTCTGCCCGGGTCCCCGGAACAGCCACCCCAAGTGCTCTCTCC

CAAGTGGACTCTCCCTTCACACCCTGCCCCTCGCATCCAGTGCACCGGC

AAGC[A/G]ACACTATCCCGGTGCCCACTCCAGAAAGTCAATGTCTCAG

GAATCTGGGGAGCCATCAGTCAAAATTACTATCATACAGTATATATAGG

ATTCGCATATATTCCTATGCATAATAATTATACGTTTTGTGGATAATAA

ATATATGTATATATGCATAATATTTACATAATATATACATATTTATATA

CATTTTATACATT

PDK4 (PDK4_38973231 (A/G) SNP)

This SNP is located on Chromosome 4 of *Equus caballus* at position 38,973,231 bp of the Horse Genome Sequence (*Equus caballus* Version 2.0) which can be viewed at www.broad.mit.edu/mammals/horse/.

The horse genome EquCab2 assembly is a Whole Genome Shotgun (WGS) assembly at 6.79× and was released in September 2007. A female Thoroughbred named "Twilight" was selected as the representative horse for genome sequencing. The project coordination and genome sequencing and assembly is provided by the Broad Institute. The N50 size is the length such that 50% of the assembled genome lies in blocks of the N50 size or longer. The N50 size of the contigs is 112.38 kb, and the total length of all contigs is 2.43 Gb. When the gaps between contigs in scaffolds are included, the total span of the assembly is 2.68 Gb. The horse EquCab2 was annotated using a standard Ensembl mammalian pipeline. Predictions from vertebrate mammals as well as horse proteins have been given priority over predictions from non-vertebrate mammals. The set of predictions was been compared to 1:1 homologues genes in human and mouse, and missing homologs in the horse annotation have been recovered using exonerate. Horse and human cDNAs have been used to add UTRs to protein based predictions. The final gene-set comprises 20,737 protein-coding genes, 2,863 identified as pseudogenes and 1,580 classified as retro-transposed genes.

Further details of the SNP are as follows:
SNP: PDK4_38973231 (A/G) P=0.001676 OR=2.2
EquCab2.0 SNP_ID: BIEC2-903605
Genomic location of SNP: Intron 2
Substitution type: Transition
The SNP is 4 bp upstream from a transcription factor (Two-handed zinc finger homeodomain transcription factors) binding site (ta/gtgtGTTTcaga).
The flanking sequence and SNP (bold and square brackets) is as follows:

(SEQ ID No. 4)
ACTTTAACCCTCAACTTTCTAACTTAAAATTTATGTTTAACTATTCCAG

AGCAATATTCAGTTTTATTTGGCAAATGTTTTCATTTTTTATAGCAAAA

GTATTTAGAAATTTTTAAGAAAGATTTCATATTTCTTTCTACTTCATTC

ATTCATGTGTGGGTAGAAGTCTCGAAAGCAGCAGTAAAGACTATGGATT

GAAT[A/G]TGTGTTTCAGATTGTCATTGTTTAATGGGTATGGAATGCA

TATATTTCTTGAATCAATGAACAAAACGCTGTATAGTCAGCAGATTAGG

GTGAGGCTCTGGTGCATATCTGCTGCAGTGCATATCCTGGCTCTATTCT

CTGAAAATCTGCTCTTGTGGGTCATCTACCCTCTCTAAGCTTMAGCACC

CTTATTTGTTAAA

Risk Prediction

The prediction of 'risk' for complex traits is greatly enhanced by testing multiple genes contributing to a trait, rather than relying on single gene SNPs (Yang et al 2003) if the additive genetic variance is small. However, single SNPs may be used where the effect is large (i.e. high odds ratio). Based on subpopulation prediction using population allele frequencies (for SNPs in HWE) or observed genotype frequencies (for SNPs deviating from HWE) and Bayes Theorem we investigated the probability of being a member of one or other subpopulation (elite or non-elite) given a certain combination of genotypes for the sequence variants in the PDK4, CKM and COX4I2 genes. Results are provided in Table 9 below as a percentage chance of being a member of each of the two subpopulations.

TABLE 9

Predictive test for Elite racing ability using SNPs in the genes PDK4, CKM and COX4I2. (The genotype combinations are ranked by most to least favourable for racing ability)

| | | | | TBE Population 1: allele, genotype freqs | | | | | TBO Population 2: allele, genotype freqs | | | | |
|---|---|---|---|---|---|---|---|---|---|---|---|---|---|
| Locus | AA | AB | BB | A | AA | AB | BB | P(G\|C) | A | AA | AB | BB | P(G\|C) |
| PDK4 | 1 | | | 0.464 | 0.22 | 0.50 | 0.29 | 0.22 | 0.282 | 0.08 | 0.41 | 0.52 | 0.08 |
| COX4I2 | | | 1 | 0.325 | 0.05 | 0.55 | 0.40 | 0.40 | 0.455 | 0.21 | 0.50 | 0.30 | 0.30 |
| CKM | | | 1 | 0.074 | 0.01 | 0.14 | 0.86 | 0.86 | 0.164 | 0.03 | 0.27 | 0.70 | 0.70 |
| | | | | | P(G\|C) | | | 0.074 | | | | | 0.02 |
| PDK4 | AA | AG | GG | | P(C) | | | 0.5 | | | | | 0.5 |
| COX4I2 | CC | CT | TT | | P(G\|C) P(C) | | | 0.037 | | | | | 0.01 |
| CKM | GG | GA | AA | | | | | | | | | | |
| | | | | | P(C\|G) | | | 0.817 | | | | | 0.18 |

| | | | Sub-population prediction from genotype based on obs population genotype frequencies and Bayes Theorem | |
|---|---|---|---|---|
| PDK4 | COX4I2 | CKM | TBE | TBO |
| AA | TT | AA | 0.82 | 0.18 |
| AA | CT | AA | 0.79 | 0.21 |
| AG | TT | AA | 0.67 | 0.33 |
| AA | TT | GA | 0.65 | 0.35 |
| AG | CT | AA | 0.63 | 0.37 |
| AA | CT | GA | 0.60 | 0.40 |
| GG | TT | AA | 0.48 | 0.52 |
| AG | TT | GA | 0.45 | 0.55 |
| AA | CC | AA | 0.44 | 0.56 |
| AA | TT | GG | 0.44 | 0.56 |
| GG | CT | AA | 0.43 | 0.57 |
| AG | CT | GA | 0.40 | 0.60 |
| AA | CT | GG | 0.38 | 0.62 |
| AG | CC | AA | 0.27 | 0.73 |
| GG | TT | GA | 0.27 | 0.73 |
| AA | CC | GA | 0.25 | 0.75 |
| AG | TT | GG | 0.25 | 0.75 |
| GG | CT | GA | 0.23 | 0.77 |
| AG | CT | GG | 0.22 | 0.78 |
| GG | CC | AA | 0.14 | 0.86 |
| AG | CC | GA | 0.13 | 0.87 |
| GG | TT | GG | 0.13 | 0.87 |
| AA | CC | GG | 0.11 | 0.89 |
| GG | CT | GG | 0.11 | 0.89 |
| AG | CC | GG | 0.06 | 0.94 |

TABLE 9-continued

Predictive test for Elite racing ability using SNPs in the genes PDK4, CKM and COX4I2. (The genotype combinations are ranked by most to least favourable for racing ability)

| | | | | |
|---|---|---|---|---|
| GG | CC | GA | 0.06 | 0.94 |
| GG | CC | GG | 0.03 | 0.97 |

In which for PDK4: AA represents genotype AA, AB represents genotype AG and BB represents genotype GG; for COX4I2: AA represents genotype CC, AB represents genotype CT, and BB represents genotype TT; and for CKM: AA represents genotype GG, AB represents genotype GA, and BB represents genotype AA.

From Table 9 it can be seen that the most favourable combination of genotypes at these three genes is AA, TT, AA for PDK4, COX4I2 and CKM respectively (82% chance of being an elite racehorse, 18% chance of being a non-elite) and the least favourable combination of genotypes at these three genes is GG, CC, GG for PDK4, COX4I2 and CKM respectively (3% chance of being an elite racehorse, 97% chance of being a non-elite).

The risk prediction test may be performed using one or more of the SNPs listed in the appendices.

Example 4

Quantitative Association of SNPs with Handicap Rating (RPR)

Racing Post Ratings (RPR) are a handicap rating determined by a horse's overall performance in a given race with respect to the race level, field quality, weight carried and time of the race. RPR are not directly comparable to speed ratings, rather the rating is intended to represent the weight a horse would be required to carry in a handicap. For example, in races restricted to horses of the same age and sex, a horse with a Racing Post Rating of 120 would, in a handicap, carry three pounds more than a horse rated 117. In open races, sex and weight-for-age allowances are factored in. Thus, in a handicap, if a horse carrying 120 pounds defeats a horse carrying 128 pounds by a length, the horse carrying 128 pounds will generally receive a Racing Post Rating six or seven pounds higher than the horse who carried 120 pounds. Guideline values to help determine a good rating for winners of races in different divisions are given in Table 10 below.

TABLE 10

Guideline RPR for winning horses

| | 2-Year-Olds | 3-Year-Olds | 4-Year-Olds & Up |
|---|---|---|---|
| Group 1 | 120 | 125 | 130 |
| Group 2 | 115 | 117 | 120 |
| Group 3 | 105 | 110 | 115 |
| Listed Race | 95 | 105 | 110 |
| Maidens | 80 | 85 | — |

We examined whether there was a significant relationship between some of the SNPs that have shown a significant association with athletic performance and RPR in a quantitative association test analysis. Table 11 below shows three SNPs that are significantly associated with RPR.

TABLE 11

SNPs having a significant association with RPR

| CHR | SNP | STAT | EMP1 | NP |
|---|---|---|---|---|
| 4 | PDK4_38973231 | 8.095 | 0.005052 | 4750 |
| 4 | PDK4_38969307 | 6.825 | 0.009441 | 2541 |
| 3 | COX4I1_32772871 | 6.748 | 0.009681 | 2478 |

Table 12 below shows the mean RPR for each genotype for the three significantly associated SNPs listed in Table 11 above.

TABLE 12

Mean RPR for each genotype of the SNPs from Table 11

| CHR | SNP | VALUE | G11 | G12 | G22 |
|---|---|---|---|---|---|
| 4 | PDK4_38973231 | GENO | A/A | A/G | G/G |
| 4 | PDK4_38973231 | COUNTS | 19 | 46 | 44 |
| 4 | PDK4_38973231 | FREQ | 0.1743 | 0.422 | 0.4037 |
| 4 | PDK4_38973231 | MEAN | 99.95 | 97.7 | 80.3 |
| 4 | PDK4_38973231 | SD | 33.78 | 28.9 | 28.85 |
| 4 | PDK4_38969307 | GENO | A/A | A/C | C/C |
| 4 | PDK4_38969307 | COUNTS | 16 | 42 | 42 |
| 4 | PDK4_38969307 | FREQ | 0.16 | 0.42 | 0.42 |
| 4 | PDK4_38969307 | MEAN | 97.19 | 99.21 | 79.9 |
| 4 | PDK4_38969307 | SD | 36.23 | 28.06 | 28.45 |
| 3 | COX4I1_32772871 | GENO | T/T | T/C | C/C |
| 3 | COX4I1_32772871 | COUNTS | 13 | 42 | 50 |
| 3 | COX4I1_32772871 | FREQ | 0.1238 | 0.4 | 0.4762 |
| 3 | COX4I1_32772871 | MEAN | 100.6 | 99.71 | 83.3 |
| 3 | COX4I1_32772871 | SD | 29.46 | 28.92 | 30.49 |

Referring to Table 12 above, at PDK4__38973231-(A/G) the AA genotype has a mean RPR of 99.95, the AG genotype has a mean RPR of 97.7 and the GG genotype has a mean RPR of 80.3. Therefore we conclude that the AA and AG genotypes are the favourable genotypes correlated with higher RPR. At COX4I1__32772871-(C/T) the TT genotype has a mean RPR of 100.6, the TC genotype has a mean RPR of 99.71 and the CC genotype has a mean RPR of 83.3. Therefore we conclude that the TT and TC genotypes are the favourable genotypes correlated with higher RPR.

COX4I1 SNP (COX4I1__32772871 (C/T) SNP)

This SNP is located on Chromosome 3 of *Equus caballus* at position 32,772,871 bp of the Horse Genome Sequence (*Equus caballus* Version 2.0) which can be viewed at www.broad.mit.edu/mammals/horse/.

The horse genome EquCab2 assembly is a Whole Genome Shotgun (WGS) assembly at 6.79× and was released in September 2007. A female Thoroughbred named "Twilight" was selected as the representative horse for genome sequencing. The project coordination and genome sequencing and assembly is provided by the Broad Institute. The N50 size is the length such that 50% of the assembled genome lies in blocks of the N50 size or longer. The N50 size of the contigs is 112.38 kb, and the total length of all contigs is 2.43 Gb. When the gaps between contigs in scaffolds are included, the total span of the assembly is 2.68 Gb. The horse EquCab2 was annotated using a standard Ensembl mammalian pipeline. Predictions from vertebrate mammals as well as horse proteins have been given priority over predictions from non-vertebrate mammals. The set of predictions was been compared to 1:1 homologues genes in human and mouse, and missing homologs in the horse annotation have been recovered using exonerate.

Horse and human cDNAs have been used to add UTRs to protein based predictions. The final gene-set comprises 20,737 protein-coding genes, 2,863 identified as pseudogenes and 1,580 classified as retro-transposed genes.

Further details of the SNP are as follows:
SNP: COX4I1_32772871 (C/T) EMP1=0.009681
EquCab2.0 SNP_ID: BIEC2-816028
Genomic location of SNP: Intron
Substitution type: Transition
The flanking sequence and SNP (bold and square brackets) is as follows in which M is A or C:

(SEQ ID No. 32)
TCAGGTCTCAGTCGCACCAGAGCTGGATGGAGCCAGCGCAGCTCCATCT

CTCAGTGGCTGGGAGTGGGCTGCAGGGTGGTCCTCACACAAGATGGGCA

CCTCCCTCCTGGGCTCCATCCCAGGACTGTTTCCCAGGTTTGGGAAACT

GGCTCGCATTAGCCGAGTGGCGTGAGCCGGAATMTGATTTACTCACAGT

GCGC[T/C]GTGCTTGGTGGGGAACGACTTCCCTGCTTTGTACAGCACC

CTGCGTTTCCAGTGGTGGTTTGTCTGGTCACTAGTCTTTTATCAAGAGA

TAGTATAGTGAAGGTTAGGTCAAGGAAAAGGGAACTCTGACTTGTCAGA

GGGCTGTTTGAACTGTATGGGGACTGCATCTCGATAACCAGGATTCTGG

GTCTCCAGACCCA

In a quantitative association test analysis this SNP is significantly associated with RPR.

Example 5

A Gene Prediction Test for Elite Sprint Race Performance in Thoroughbred Horses

Thoroughbred horses excel in both sprint (<1,500 m) and longer distance (>1,800 m) races. Horses competing in middle distance races ('milers' and 'middle distance') may be considered either 'sprinters' or 'stayers' and the way in which a race is executed by the rider often reflects the trainer's perceived sprinting and endurance ability of the horse. Within the industry horses may be described as sprinters based on their conformation and usually have a stockier and more muscular stature and are faster maturing. They usually race as 2 year olds and over shorter distances as 3 year olds. Individuals perceived to be longer distance animals may be referred to as 'backward' requiring more time to mature and running over longer distances as 3 year olds. In some regions (e.g. Australia) breeders attempt to breed only faster 'sprint' type horses.

In some aspects, the invention provides a simple DNA based method (genotype test) for predicting the elite sprint race performance of a thoroughbred race horse based on the presence or absence of a SNP in one or more exercise response gene. The exercise response gene may be one or more of the genes listed in the appendices. For example the genotype test may be based on a SNP in one or more of the MSTN, ACN9, PTPN1, PON1, ADHFE1, or GSN genes. Details of some of the SNPs that may be used to predict the elite sprint race performance of a thoroughbred race horse are given in the appendices. It will be appreciated that the genotypic test may be based on a combination of any one or more of these SNPs.

In this non-limiting example, we studied the MSTN gene.
Methods
Association Sample The International Federation of Horseracing Authorities recognizes five distance categories: Sprint (5-6.5 f, ≤1,300 m), Mile (6.51-9.49 f, 1,301-1,900 m), Intermediate (9.5-10.5 f, 1,901-2,112 m), Long (10.51-13.5 f, 2,114-2,716 m) and Extended (>13.51 f, >2,717 m) races (International Federation of Horseracing Authorities Classifications, www.horseracingintfed.com) [Note: 1 furlong=⅛ mile=201.2 meters]. For the case-control investigations we compared two cohorts: samples were subdivided into short (≤8 f and ≤7 f) and long (>8 f) distance racing cohorts. To avoid animals with excessive consanguinity (within two generations) and over-representation of popular sires within the pedigrees, a set of Thoroughbred DNA samples (n=148) was selected from a large DNA sample repository (n>1,000) collected with informed owners' consent from Thoroughbred training, breeding and sales establishments in Ireland and New Zealand during 1998-2008.
Replication Sample To minimize non-genetic influences on performance the findings were validated by genotyping elite (Group and Listed race winning) racehorse samples (n=39) selected from a repository of DNA samples (n=419) from horses trained by the same trainer in Ireland during 2004-2008. A subset (n=142) of this repository was evaluated for genotypic trends with parameters of racecourse success in two-year-old racehorses. Race records were derived from three sources: European race records, The Racing Post on-line database (www.racingpost.co.uk); Australasian and South East Asian race records, Anion Pedigrees (www.arion.co.nz); and North American race records: Pedigree Online Thoroughbred database (www.pedigreequery.com). The replication samples had some sharing of relatives, accounted for in the analyses.
DNA Extraction, Re-Sequencing and Genotyping Genomic DNA was extracted from either fresh whole blood or hair samples using a modified version of a standard phenol/chloroform method (Sambrook & Russell 2001). Thirteen pairs of overlapping PCR primers were designed to cover the entire MSTN genomic sequence using the PCR Suite extension to the Primer3 web-based primer design tool (Rozen & Skaletsky 2000; van Baren & Heutink 2004) (Table 13). Twenty-four unrelated Thoroughbred DNA samples were included in a re-sequencing panel to identify Thoroughbred-specific sequence variants. As such this study was powered to detect 95% of SNPs with MAF>0.05 in the Thoroughbred population (Kruglyak & Nickerson 2001). Bidirectional DNA sequencing of PCR products was outsourced to Macrogen Inc. (Seoul, Korea) and carried out using AB 3730×1 sequencers (Applied Biosystems, Foster City, Calif.). Sequence variants were detected by visual examination of sequences following alignment using Consed version 19.0 (090206)[Gordon et al 1998] Genotyping was carried out using Sequenom (San Diego, USA) iPlex technology at Sequenom facilities in San Diego, USA (Association samples) and Hamburg, Germany (Replication samples).
Statistical Analyses All statistical analyses, including tests of association were performed using PLINK Version 1.05 (Purcell et al 2007). Quality control analyses included computation of sample allele frequency, percent missing genotypes and deviation from Hardy-Weinberg equilibrium. The series of case-control association tests were performed for two loci (g.66493737C>T and g.66494218A>C). Statistical significance was assessed using the Cochran-Armitage test for trend and an unconditioned genotypic model. Odds ratios and 95% CIs were calculated for the two most significant associations. The linear regression model was used to evaluate quantitative trait association at locus g.66493737C>T using the phenotypes: best race distance and kg/cm ratio.

Results

Horses, in particular Thoroughbreds, have a very high muscle mass to body weight ratio (55%) compared to other mammalian species (30-40%) (Gunn 1987). Myostatin gene (MSTN) variants have previously been shown to contribute to muscle hypertrophy; therefore, sequence variation in the equine MSTN gene, which contains three exons and spans 6,172 bp on chromosome 18 (reverse strand nt 66489608-66495780, EquCab2.0) was investigated. To-date, no sequence variants have been reported in genomic MSTN sequence in Thoroughbred horses and no MSTN SNPs are documented in the EquCab2.0 SNP database. Novel sequence variants were identified by re-sequencing the equine MSTN gene in 24 unrelated Thoroughbred horses using 14 overlapping primer pairs (Table 13) spanning all three exons and 288 bp of the 5' upstream region. Although no exonic sequence variants were detected, six SNPs were detected in intron 1 of MSTN [nt 66492979-66494807] (Table 14).

Population genetic diversity analyses suggest that selection for the region containing the MSTN gene has been strong in the Thoroughbred population. Thirteen microsatellite loci spanning equine chromosome 18 were genotyped in three populations of unrelated Thoroughbred (n=106), Akhal-Teke (n=18), Connemara (n=17) and Tuva (n=17) horses. In Thoroughbred, evaluation of linkage disequilibrium indicated conserved haplotypes encompassing the two loci in closest proximity to the MSTN gene: TKY101 (nt.63528459) and TKY016 (nt.66838920). Among population differentiation ($F_{ST}$) was high at TKY016 ($F_{ST}$ 0.23), which was among the top 10% of (n=394) genome-wide loci when ranked by $F_{ST}$ (Gu et al 2009). Interestingly, the highest $F_{ST}$ score on chromosome 18 was for TKY303 (nt.31.1 Mb; $F_{ST}$=0.31), which is in close proximity to the ACVR2A gene encoding activin A receptor, type IIA, a key signaling molecule for myostatin. The high $F_{ST}$ at TKY016, located 350 kb from MSTN, results from divergent allele frequency distributions among Thoroughbred and non-Thoroughbred populations and redistribution of Thoroughbred samples into distance cohorts (TBE≤8 f; n=25 and TBE>8 f n=22) identified a significant difference (Pearson's chi-square test; $\chi^2$=5.809; df=1; P=0.0159) in allele 144 frequency (TBE≤8 f=70%; TBE>8 f=45%).

To investigate associations between MSTN sequence variants and racing phenotypes we genotyped n=148 Thoroughbred horses. Four of the six MSTN sequence polymorphisms displayed MAF<0.05 in Thoroughbreds (Table 15) and were excluded from the association analyses. A series of population-based case-control investigations by separating the Thoroughbreds on the basis of retrospective racecourse performance into discrete cohorts containing unrelated animals (Table 16) was performed. Individual genotypes at the two SNPs used for the analyses (g.66493737C>T and g.66494218A>C) were not more common among elite Group race winning Thoroughbreds (Thoroughbred-elite, TBE) than horses that had never won a race (Thoroughbred-other, TBO) (Table 17). Also, no association was detected when handicap ratings, reflecting retrospective racing ability, were evaluated as a quantitative phenotype. However, considering the relative contribution of muscle power to sprint and longer distance racing, the elite Group race winning animals were subdivided into those that had won their best (most valuable or highest grade) race over distances ≤8 f (n=51) and those that had won their best race over distances >8 f (n=35) and found highly significant associations [Note: 1 furlong=⅛ mile=201.2 meters]. In Britain, of the 139 Group races per annum 57% are run over distances ≤1 mile and 43% are run over distances >1 mile. The elite performer cohort contained a subset of animals (n=71) that competed preferentially in short distance (≤8 f, n=39) and long distance (>8 f n=32) races.

For all analyses the significance of association was consistently higher for g.66493737C>T than g.66494218A>C and the linkage disequilibrium between these SNPs was relatively high ($r^2$=0.50). Conditioning on each SNP using a logistic regression model identified an independent effect for g.66493737C>T on g.66494218A>C (P=0.0108) but not for g.66494218A>C on g.66493737C>T (P=0.7388) and therefore only the results for g.66493737C>T were considered further. Among the two distance cohorts we found a highly significant (P=3.70×10$^{-5}$) association with g.66493737C>T and this association became marginally stronger (P=1.88× 10$^{-5}$) when the short distance cohort was further subdivided into animals (n=43) that had won their best race over distances ≤7 f (Table 17a).

The C allele was twice as frequent in the short distance (≤7 f) than in the long distance (>8 f) cohort (0.72 and 0.36 respectively) corresponding to an odds ratio of 4.54 (95% C.I. 2.23-9.23). When all Thoroughbreds were considered together the locus conformed to expected Hardy-Weinberg proportions (Table 18). However, there was a significant (P=0.0018) deviation from HWE in the longer distance cohort, possibly due to selection at this locus. Conversely, the C/C genotype was the most common genotype among sprinters (≤7 f, >51%). Genotype trend effects were modeled by estimating the risk associated with a linear trend in magnitude of effect relative to the common homozygote, heterozygote, and rare homozygote genotype using the Cochran-Armitage test for the trend model. The most parsimonious model was the genotypic model (P=1.18×10$^{-6}$) indicating that genotypes are predictive of racing distance (Table 17b).

TABLE 13

PCR primer details for SNP discovery
in the equine myostatin (MSTN) gene

| Amplicon | Primer sequences (5') | Primer sequences (3') | PCR product size (bp) | Chr location (EquCab2.0) | No. of SNPs identified |
|---|---|---|---|---|---|
| MSTN_1 | ATAAATGCAATTGT CTCAAAGTC (SEQ ID NO. 5) | CCATATGCAAGTT TCCATTCC (SEQ ID NO. 6) | 399 | chr18: 66489320 +66489718 | — |
| MSTN_2 | TCAGCCATTCAGCC TATTTG (SEQ ID NO. 7) | ACGGTTGGCATTT AACCATC (SEQ ID NO. 8) | 422 | chr18: 66489629 +66490050 | — |

TABLE 13-continued

PCR primer details for SNP discovery in the equine myostatin (MSTN) gene

| Amplicon | Primer sequences (5') | Primer sequences (3') | PCR product size (bp) | Chr location (EquCab2.0) | No. of SNPs identified |
|---|---|---|---|---|---|
| MSTN_3 | GGAGACTTGCTTTC ATTTACCTG (SEQ ID NO. 9) | GAAGCTTTTGGAT GGGATTG (SEQ ID NO. 10) | 552 | chr18: 66489914 +66490465 | — |
| MSTN_4 | CTCTGGGGTTTGCT TGGTG (SEQ ID NO. 11) | ACCTAGGGAATG GAGGATGG (SEQ ID NO. 12) | 695 | chr18: 66490336 +66491030 | — |
| MSTN_5 | GAAGAGGAGGGAG GGAAGAG (SEQ ID NO. 13) | TTCAGTCTTCATG TGGTCTTGG (SEQ ID NO. 14) | 762 | chr18: 66490908 +66491669 | — |
| MSTN_7 | AAGGTATTGTCATC TGCTTGG (SEQ ID NO. 15) | CCAAGACCAGGA GAAGATGG (SEQ ID NO. 16) | 783 | chr18: 66491846 +66492628 | — |
| MSTN_8 | GCTTGTTAGCATAG GAAACTGG (SEQ ID NO. 17) | CTGAGACCCGTCA AGACTCC (SEQ ID NO. 18) | 376 | chr18: 66492499 +66492874 | — |
| MSTN_9 | CGTCTTTCATGGGT TTGATG (SEQ ID NO. 19) | ATGTTCCTCCACG GTGTCTC (SEQ ID NO. 20) | 530 | chr18: 66492805 +66493334 | 1 (Indel) |
| MSTN_10 | TGAAGGAATGAAC TGTGGATG (SEQ ID NO. 21) | GTCTGCGATCCTG CTTTACC (SEQ ID NO. 22) | 580 | chr18: 66493261 +66493840 | 5 |
| MSTN_11 | TTTTGAAACTGTTG TGTCCTG (SEQ ID NO. 23) | TCATAATTGCGTT TGGTTGC (SEQ ID NO. 24) | 674 | chr18: 66493779 +66494452 | 1 |
| MSTN_12 | GCAAATGCTCAAA TGACCTAAAC (SEQ ID NO. 25) | TGTGCTGATTCTT GCTGGTC (SEQ ID NO. 26) | 799 | chr18: 66494344 +66495142 | — |
| MSTN_13 | TGAAGATTTAGTGT TTTGTCTCC (SEQ ID NO. 27) | CGAGATTCATTGT GGAGCAG (SEQ ID NO. 28) | 382 | chr18: 66495028 +66495409 | — |
| MSTN_14 | GAGACAACTTGCC ACACCAG (SEQ ID NO. 29) | TGCCCTGGTAATA ACAATGAAG (SEQ ID NO. 30) | 786 | chr18: 66495287 +66496072 | — |

TABLE 14

Details of SNPs discovered in equine myostatin gene following resequencing in a panel of 24 unrelated Thoroughbred horses. None of these SNPs are among the SNPs in the EquCab2.0 SNP Map and have not been previously reported in any publically available literature.

| SNP ID | Chr | EquCab2.0 SNP location | Allele 1 | Allele 2 | Gene structure | Amplicon | Substitution type |
|---|---|---|---|---|---|---|---|
| MSTN_9_383-386 | chr18 | 66493222-66493225 | delACTT | | Intron 1 | MSTN_9 | |
| MSTN_10_227 | chr18 | 66493525 | T | G | Intron 1 | MSTN_10 | Transversion |
| MSTN_10_284 | chr18 | 66493582 | T | G | Intron 1 | MSTN_10 | Transversion |
| MSTN_10_439 | chr18 | 66493737 | T | C | Intron 1 | MSTN_10 | Transition |
| MSTN_10_447 | chr18 | 66493745 | A | G | Intron 1 | MSTN_10 | Transition |
| MSTN_10_477 | chr18 | 66493775 | A | G | Intron 1 | MSTN_10 | Transition |
| MSTN_11_404 | chr18 | 66494218 | A | C | Intron 1 | MSTN_11 | Transversion |

TABLE 15

Genotyping results for MSTN SNPs

| Assay (SNP_ID) | Coverage | NA. | Total | nallele | COMMON | HET | RARE | p | q | F_p | F_q (MAF) | n |
|---|---|---|---|---|---|---|---|---|---|---|---|---|
| MSTN_66493525 (SEQ ID No. 33) | 96.67% | 5 | 145 | 2 | 138 | 5 | 2 | 281 | 9 | 0.969 | 0.031 | 290 |
| MSTN_66493582 (SEQ ID No. 34) | 92% | 12 | 138 | 2 | 135 | 3 | 0 | 273 | 3 | 0.989 | 0.011 | 276 |
| MSTN_66493737 (SEQ ID No. 31) | 93.33% | 10 | 140 | 2 | 42 | 75 | 23 | 159 | 121 | 0.568 | 0.432 | 280 |
| MSTN_66493745 (SEQ ID No. 35) | 97.33% | 4 | 146 | 2 | 139 | 6 | 1 | 284 | 8 | 0.973 | 0.027 | 292 |
| MSTN_66493775 (SEQ ID No. 36) | 96.67% | 5 | 145 | 2 | 139 | 5 | 1 | 283 | 7 | 0.976 | 0.024 | 290 |
| MSTN_66494218 (SEQ ID No. 37) | 91.33% | 13 | 137 | 2 | 59 | 67 | 11 | 185 | 89 | 0.675 | 0.325 | 274 |

TABLE 16

Population summary including details of retrospective racecourse success for each cohort.

| | n | No. sires | No. Males | No. Females | Mean RPR | Range RPR | Total no. races | Mean no. races | No. races won | No. Gr races won | No. Gr 1 races won | Mean no. Gr races won |
|---|---|---|---|---|---|---|---|---|---|---|---|---|
| TBE | 86 | 86 | 37 | 49 | 115 | 87-134 | 1170 | 13.8 | 425 | 215 | 91 | 2.5 |
| TBE > 8 f | 35 | 35 | 12 | 23 | 119 | 107-134 | — | — | — | 89 | 42 | — |
| TBE ≤ 8 f | 51 | 51 | 25 | 26 | 114 | 87-129 | — | — | — | 129 | 49 | — |
| TBE ≤ 7 f | 43 | 43 | 20 | 23 | 113 | 87-129 | — | — | — | 76 | 23 | — |
| TBO | 62 | 62 | 22 | 40 | 59 | 21-89 | 537 | 8.7 | 15 | 0 | 0 | 0 |

TABLE 17 a. Case-control association test results for a series of cohort comparisons for g.66493737C>T. TBE: elite Group race winning Thoroughbreds; TBO: other non-winning Thoroughbreds; TBE > 8 f, TBE ≤ 8 f and TBE ≤ 7 f: elite Group race winning Thoroughbreds that won their best (most valuable or highest grade) races over distances >8 f, ≤8 f and ≤7 f. In each case the frequency of the g.66493737-T allele is given. Odds ratios were calculated for the two most significant results. b. Best-fit model results for g.66493737C>T association with elite Group race winning performance over distances ≤7 f.

| a. | Pop 1 vs Pop 2 | Freq T_ Pop 1 | Freq T_Pop 2 | CHISQ | P | OR |
|---|---|---|---|---|---|---|
| | TBE vs TBO | 0.443 | 0.425 | 0.09 | 0.764 | — |
| | TBE > 8 f vs TBE ≤ 8 f | 0.641 | 0.309 | 17.02 | 3.70E−05 | 3.996 |
| | TBE > 8 f vs TBE ≤ 7 f | 0.641 | 0.282 | 18.31 | 1.88E−05 | 4.538 |
| | TBE > 8 f vs TBO | 0.641 | 0.425 | 7.76 | 0.005 | — |
| | TBE ≤ 8 f vs TBO | 0.309 | 0.425 | 3.06 | 0.080 | — |
| | TBE ≤ 7 f vs TBO | 0.282 | 0.425 | 4.15 | 0.042 | — |

| b. | | TBE > 8 f | TBE ≤ 7 f | P |
|---|---|---|---|---|
| | Genotypic (C/C, C/T, T/T) | 0/23/9 | 21/23/3 | 1.18E−06 |
| | Trend (C, T) | 23/41 | 65/29 | 5.23E−06 |

TABLE 18

Hardy-Weinberg equilibrium test results for locus g.66493737C>T.

| TEST | A1 | A2 | GENO | O(HET) | E(HET) | P |
|---|---|---|---|---|---|---|
| ALL | T | C | 23/75/41 | 0.5396 | 0.4916 | 0.3022 |
| TBE < 7 f | T | C | 3/16/20 | 0.4103 | 0.4050 | 1 |
| TBE > 8 f | T | C | 9/23/0 | 0.7188 | 0.4604 | 0.0018 |

MSTN SNP (MSTN_66493737 (77C) SNP)

This SNP is located on Chromosome 18 of *Equus caballus* at position 66,490,208-66,495,180 reverse strand of the Horse Genome Sequence (*Equus caballus* Version 2.0) which can be viewed at www.broad.mit.edu/mammals/horse/.

The horse genome EquCab2 assembly is a Whole Genome Shotgun (WGS) assembly at 6.79× and was released in September 2007. A female Thoroughbred named "Twilight" was selected as the representative horse for genome sequencing. The project coordination and genome sequencing and assembly is provided by the Broad Institute. The N50 size is the length such that 50% of the assembled genome lies in blocks of the N50 size or longer. The N50 size of the contigs is 112.38 kb, and the total length of all contigs is 2.43 Gb. When the gaps between contigs in scaffolds are included, the total span of the assembly is 2.68 Gb. The horse EquCab2 was annotated using a standard Ensembl mammalian pipeline. Predictions from vertebrate mammals as well as horse proteins have been given priority over predictions from non-vertebrate mammals. The set of predictions was been compared to 1:1 homologues genes in human and mouse, and missing homologs in the horse annotation have been recovered using exonerate. Horse and human cDNAs have been used to add UTRs to protein based predictions. The final gene-set comprises 20,737 protein-coding genes, 2,863 identified as pseudogenes and 1,580 classified as retro-transposed genes.

Further details of the SNP are as follows:
SNP: MSTN_66493737 (T/C) P=1.88E-050R=4.54
EquCab2.0 SNP_ID: not detected in EquCab2.0 database.
No report of SNP in on-line bioinformatics resources.
In house SNP_ID: MSTN-10_439
Genomic location of SNP: Intron 1
Substitution type: Transition
The flanking sequence and SNP (bold and square brackets) is as follows:

(SEQ ID No. 31)
AGCTAAGCAAGTAATTAGCACAAAAATTTGAATGTTATATTCAGGCTAT

CTCAAAAGTTAGAAAATACTGTCTTTAGAGCCAGGCTGTCATTGTGAGC

AAAATCACTAGCAATTTCTTTTATTTTGGTTCCCCAAGATTGTTTATAA

ATAAGGTAAATCTACTCCAGGACTATTTGATAGCAGAGTCATAAAGGAA

AATTA[T/C]TTGGTGCATTATAACCTGATTACTTAATAAGGAGAACAA

TATTTTGAAACTGTTGTGTCCTGTTTAAAGTAGATAAAGCACTGGGTAA

AGCAGGATCGCAGACACATGGCACAGAATCTTCCGTGTCATGCCTTCTC

TGTGAAGGTGTCTGTCTCCCTTTCCTTGAGTGTAGTTATGAACTGACTG

CAAAAAGAATATATG

Figure 6A:
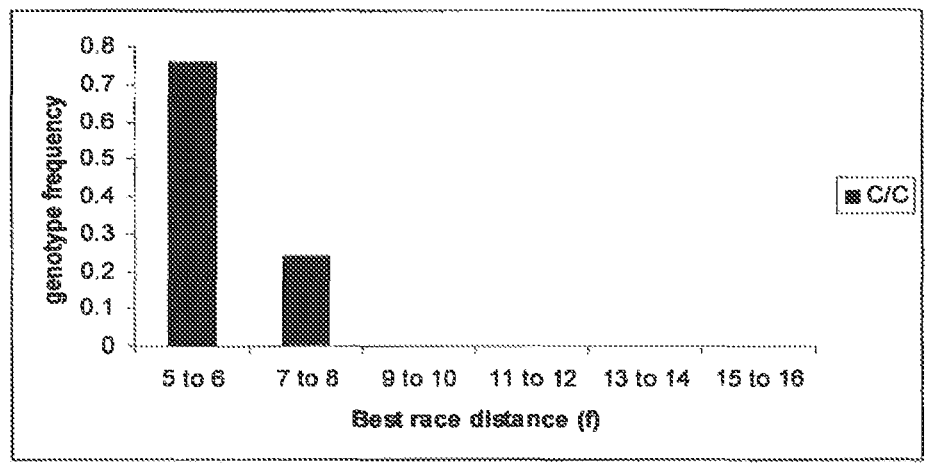
FIGS. 6 (A) to (C) are graphs showing the genotype frequency for best race distance for the MSTN 66493737 (T/C) SNP in which (A) shows the C/C genotype frequency; (B) shows the C/T genotype frequency; and (C) shows the T/T genotype frequency.
Figure 6B:
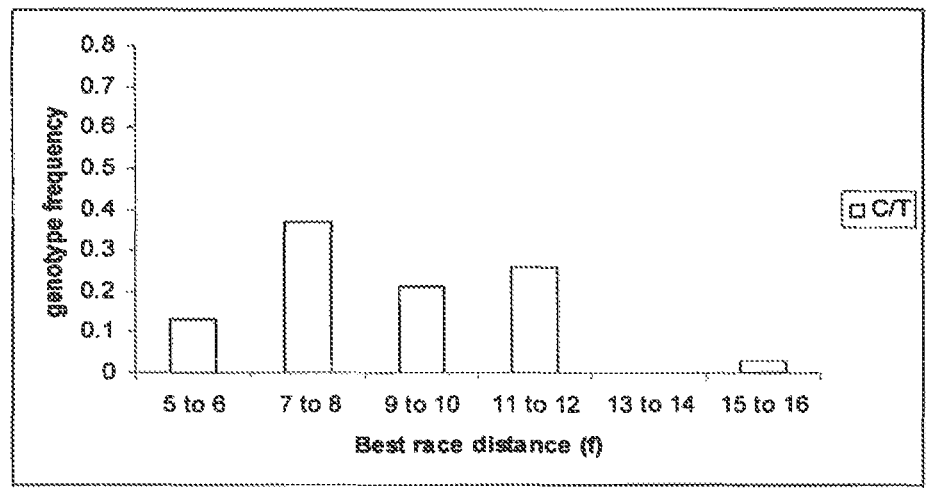
Figure 6C:
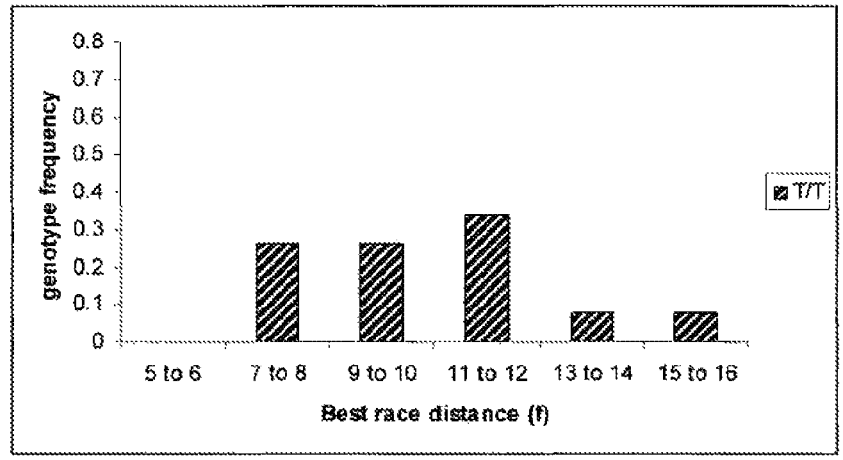
Figure 7:
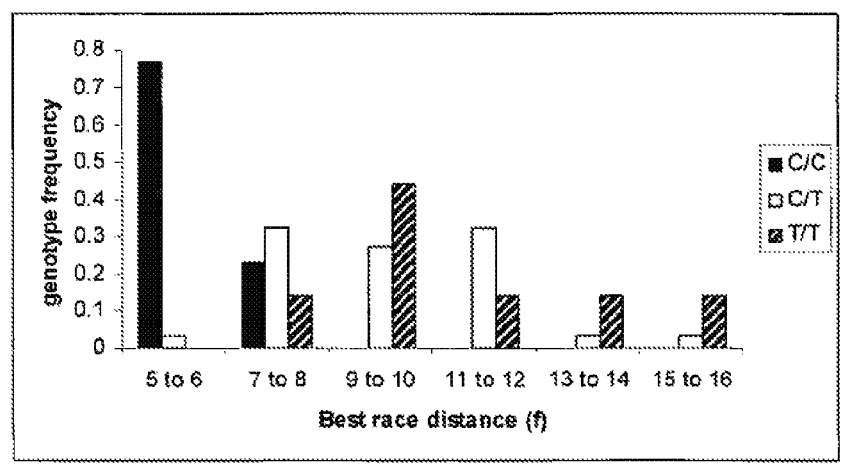
FIG. 7 is a graph showing the genotype frequency for best race distance for the MSTN 66493737 (T/C) SNP in which the best race distance for horses that had won their group race as a two-year-old was replaced with the average distance of their three-year-old races.

Considering best race distance (BRD) as a quantitative trait, we analyzed the data for the elite cohort using the distance (furlongs) of the highest grade or most valuable Group race won as the phenotype (n=79). BRD was highly significantly associated (P=4.85×10$^4$) with the g.66493737C>T SNP (Table 19). This result was independently validated (P=0.0047) in a cohort of 37 elite racehorses (n=27 Group race winners and n=10 Listed race winners) produced by the same trainer. For each genotype we determined the mean BRD (Table 20): C/C mean=6.2±0.8 f; C/T mean=9.1±2.4 f; and T/T mean=10.5±2.7 f. A distribution of the genotypes in two furlong increments is shown in FIGS. 6A to 6. It is important to note that a bias may be introduced to these distances as two-year-old Group races are limited to ≤8 f in Ireland and the United Kingdom (there are only three Group races for two-year-olds in Europe >8 f). Therefore we replaced BRD for horses that had won their only Group race as two-year-olds with the average distance of their three-year-old races (n=73), which resulted in a marginal increase in the means for the three genotypes (C/C mean=6.4±1.0 f; C/T mean=9.7±2.0 f; and T/T mean=10.9±2.4 0 and an increase in the significance of association (P=5.45×10$^{-9}$) (FIG. 7).

Figure 8:
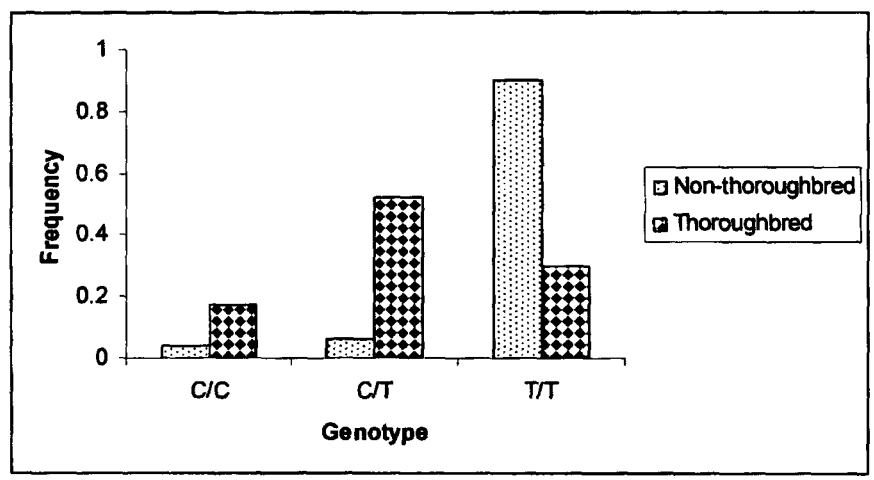
FIG. 8 is a graph showing the genotype frequency for the MSTN 66493737 (T/C) SNP in a non-thoroughbred population known for endurance exercise capabilities (Egyptian Arabian horse) and a thoroughbred population.

Eight National Hunt (races over obstacles and distances 16-36 racehorses were also genotyped for the g.66493737C>T SNP and the results support an association of the T allele with stamina (T/T, n=7; and C/T, n=1). Also, the genotype frequencies among a non-Thoroughbred population known for endurance exercise capabilities (n=31, Egyptian Arabian horse) were considerably different to the Thoroughbred population (FIG. 8). Together these findings indicate that the C/C genotype is particularly suited to sprint racing.

Figure 9:
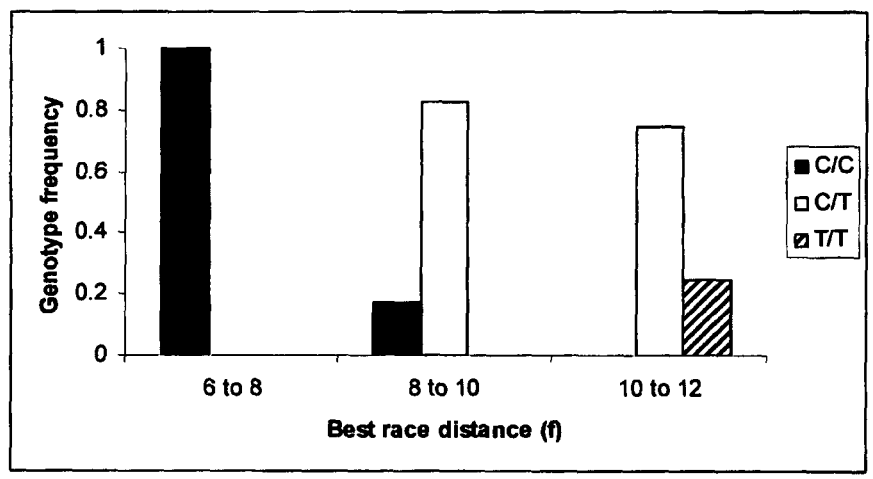
FIG. 9 is a graph showing the genotype frequency for the MSTN 66493737 (T/C) SNP for stallions with a Stamina Index 6-8f, 8-10 f, 10-12f.

In Thoroughbred breeding considerable weight is given to the contribution of the sire in the predicted best race distance of offspring. For breeding stallions a 'Stamina Index' (S.I.) is estimated as the average winning distance of all racing progeny. Therefore we investigated the distribution of genotypes for the n=19 unrelated breeding stallions with S.I. in our sample (FIG. 9). All (100%) stallions with S.I.=6-8 f had the C/C genotype; 83.3% and 75% stallions with S.I.=9-10 f and 10-12 f respectively were C/T; and 25% stallions with S.I.=10-12 f were T/T. While the sample size is small there is a clear indication that g.66493737C>T genotypes are predictive of S.I. in breeding stallions (FIG. 9).

These data indicate that genotypic information at this locus may have practical applications in the Thoroughbred horse racing and breeding industry. To evaluate this further, two-year-old racing form for n=142 horses-in-training with the same trainer during 2007 and 2008 (n=63, 2007; n=79, 2008) (Table 20a) was investigated. Consistently, for each parameter of racing success, C/C and C/T genotypes were more successful two-year-old racehorses than T/T animals (Table 20b). In terms of earnings, the greatest returns on training investment were for animals that were C/C or C/T; on average these horses earned 5.5-fold more than T/T horses. Even when individuals that had won >Sterling£100,000 (US$165,000) were excluded, on average C/C individuals earned 1.6-fold more than T/T individuals. The bulk of keeping and training expenses are not returned in prize money (72% Ireland, 78% United Kingdom for horses that have run in at least one race) [International Federation of Horseracing Authorities, www.horseracingintfed.com]; therefore, employing a strategy to train and race only C/C and C/T individuals as two-year-olds may be beneficial.

To eliminate potential confounding effects of shared sires, the racing successes of 41 half-sibs (progeny of a single sire) [C/T, n=22; T/T, n=19] (Table 20c) that were trained by the same trainer as two-year-olds was investigated. A significant genotype association with racing performance (Pearson's chi-square test: $\chi^2$=7.235; df=1; P=0.0071) was identified; five of the progeny were two-year-old Group race winners and all displayed the C/T genotype.

In many instances the goal of breeders is to breed a Derby winner. The Derby distance (12 f) predicts that individuals must have at least one copy of the T allele at g.66493737C>T. There were n=7 Derby winners in our sample: C/T n=6; and T/T n=1. Furthermore, n=51 progeny from a highly successful commercial breeding stallion that had won both the Epsom Derby and the Irish Derby were genotyped and had a S.I.=11.3 f. Among the progeny just two genotypes (n=29, C/T; and n=22, T/T) were identified suggesting that this individual (while not genotyped here) is T/T (both the sire and dam were genotyped: sire: T/T; dam: C/T). We estimated the mean BRD for the genotypes in n=9 of the stallion's progeny that had won Group races, further reinforcing the g.66493737C>T genotype trend (C/T: n=6, mean BRD=8 f; T/T: n=3, mean BRD=10.7 f).

Similar to their human counterparts, sprint racing Thoroughbreds are generally more compact and muscular than horses suited to longer distance races. Therefore, to investigate whether MSTN genotypes influence body mass, mass (kg) and height at withers (cm) measurements that were taken during two two-year-old racing seasons for n=97 (n=37 males, n=60 females) horses-in-training with the same trainer were used. Mass to height ratio displayed a significant (P=0.0147) relationship with g.66493737C>T genotype (2.94 kg/cm, C/C; 2.88 kg/cm, C/T; and 2.83 kg/cm, T/T). This association became stronger when males were considered independently (P=0.0025) of females (P=0.2272) [Table 21]. On average C/C males had 6.7% (i.e. 3.033 kg/cm versus 2.843 kg/cm) greater mass per cm than T/T males.

TABLE 19

Quantitative trait association tests and best race distance (BRD) means for a. association test sample; b. association test sample using mean three year old distances as phenotype (for two-year-olds that won their best race ≤8 f); and c. replication sample.

| | | Quantitative association test results | | | | | Best race distance means | | | |
|---|---|---|---|---|---|---|---|---|---|---|
| | n | BETA | SE | R2 | T | P | GENO | C/C | C/T | T/T |
| a. | 79 | 2.308 | 0.381 | 0.322 | 6.052 | 4.85E−08 | COUNTS | 21 | 46 | 12 |
| | | | | | | | FREQ | 0.266 | 0.582 | 0.152 |
| | | | | | | | MEAN | 6.167 | 9.087 | 10.540 |
| | | | | | | | SD | 0.827 | 2.365 | 2.742 |
| b. | 73 | 2.390 | 0.360 | 0.383 | 6.635 | 5.46E−09 | COUNTS | 19 | 42 | 12 |
| | | | | | | | FREQ | 0.260 | 0.575 | 0.164 |
| | | | | | | | MEAN | 6.421 | 9.682 | 10.930 |
| | | | | | | | SD | 1.022 | 2.081 | 2.441 |
| c. | 37 | −1.500 | 0.497 | 0.207 | −3.021 | 0.005 | COUNTS | 7 | 23 | 7 |
| | | | | | | | FREQ | 0.189 | 0.622 | 0.189 |
| | | | | | | | MEAN | 6.714 | 8.217 | 9.714 |
| | | | | | | | SD | 1.704 | 1.930 | 1.890 |

TABLE 20

Parameters of two-year-old racing (Ireland and United Kingdom) success for n = 142 horses-in-training with the same trainer during 2007 and 2008. a. Two year old horses-in-training 2007 & 2008; b. two year old horses-in-training 2007 & 2008 comparing C/C and C/T versus T/T genotypes; c. Half-sib two year old horses-in-training sharing a single sire.

| | n | no. run-ners | no. win-ners | total no. races | total no. races won | % run-ners | % win-ners to run-ners | % wins to run-ners | % win-ners to total | % wins to total | mean no. races per run-ner | total earn-ings (£) | mean earn-ings (£) | mean earnings excl. earners > £100 k | no. earners > £100 k |
|---|---|---|---|---|---|---|---|---|---|---|---|---|---|---|---|
| | | | | | | a. | | | | | | | | | |
| CC | 40 | 21 | 11 | 87 | 17 | 52.5 | 52.4 | 81.0 | 27.5 | 19.5 | 4.1 | 511114 | 20440 | 8203 | 1 |
| CT | 67 | 32 | 18 | 115 | 26 | 47.8 | 56.3 | 81.3 | 26.9 | 22.6 | 3.6 | 1801103 | 36968 | 4925 | 5 |
| TT | 35 | 13 | 6 | 40 | 6 | 37.1 | 46.2 | 46.2 | 17.1 | 15.0 | 3.1 | 87461 | 5175 | 5175 | 0 |
| | | | | | | b. | | | | | | | | | |
| CC/CT | 107 | 53 | 29 | 202 | 43 | 49.5 | 54.7 | 81.1 | 27.1 | 21.3 | 3.8 | 2312217 | 28704 | 6564 | 6 |
| TT | 35 | 13 | 6 | 40 | 6 | 37.1 | 46.2 | 46.2 | 17.1 | 15.0 | 3.1 | 87461 | 5175 | 5175 | 0 |
| | | | | | | c. | | | | | | | | | |
| CT | 22 | 12 | 9 | 46 | 18 | 54.5 | 75.0 | 150.0 | 40.9 | 39.1 | 3.8 | 1620087 | 73640 | — | 6 |
| TT | 19 | 9 | 5 | 23 | 5 | 47.4 | 55.6 | 55.6 | 26.3 | 21.7 | 2.6 | 67864 | 3572 | — | 0 |

TABLE 21

Quantitative association test results for g.66493737C>T with kg/cm ratio as phenotype

| | | Quantitative association test results | | | | | Kg/cm means | | | |
|---|---|---|---|---|---|---|---|---|---|---|
| | n | BETA | SE | R2 | T | P | GENO | C/C | T/C | T/T |
| Two year olds-in-training | 97 | −0.05671 | 0.02282 | 0.06104 | −2.485 | 0.015 | COUNTS | 29 | 47 | 21 |
| | | | | | | | FREQ | 0.299 | 0.485 | 0.217 |
| | | | | | | | MEAN | 2.939 | 2.875 | 2.826 |
| | | | | | | | SD | 0.155 | 0.162 | 0.168 |
| Males only | 37 | −0.09575 | 0.02941 | 0.2325 | −3.256 | 0.003 | COUNTS | 10 | 18 | 9 |
| | | | | | | | FREQ | 0.270 | 0.487 | 0.243 |
| | | | | | | | MEAN | 3.033 | 2.918 | 2.843 |
| | | | | | | | SD | 0.169 | 0.101 | 0.134 |
| Females only | 60 | −0.03773 | 0.03091 | 0.02505 | −1.221 | 0.227 | COUNTS | 19 | 29 | 12 |
| | | | | | | | FREQ | 0.317 | 0.483 | 0.200 |
| | | | | | | | MEAN | 2.889 | 2.848 | 2.814 |
| | | | | | | | SD | 0.124 | 0.187 | 0.194 |

Risk Prediction

Based on subpopulation prediction using population observed genotype frequencies and Bayes Theorem the probability of being a member of one or other subpopulation (elite sprinter or elite endurance or 'stayer') given a certain genotype at the MSTN gene was investigated. Results are give in Table 22 and are provided as a percentage chance of being a member of each of the two subpopulations.

Quantitative Association with Best Race Distance

It was examined whether there was a significant relationship between SNPs in the examined genes and best race distance (i.e. distance of the highest quality/most valuable Group race won) in a quantitative association test analysis using the subset of individuals that had won a Group race (i.e. TBE n=86). Table 24 below shows the SNPs significantly associated with best race distance.

TABLE 22

Predictive test for Elite Sprint racing ability

| | | | | | TBE SP Population 1: allele, genotype frequencies | | | | | | TBE EN Population 2: allele, genotype frequencies | | | |
|---|---|---|---|---|---|---|---|---|---|---|---|---|---|---|
| Locus | AA | AB | BB | A | AA | AB | BB | P(G\|C) | A | AA | AB | BB | P(G\|C) |
| MSTN | | 1 | | 0.28 | 0.08 | 0.41 | 0.51 | 0.41 | 0.64 | 0.28 | 0.72 | 0 | 0.72 |
| MSTN | TT | TC | CC | | P(G\|C) | | | 0.41 | | | | | 0.72 |
| | | | | | P(C) | | | 0.5 | | | | | 0.5 |
| | | | | | P(G\|C)P(C) | | | 0.21 | | | | | 0.36 |
| | | | | | P(C\|G) | | | 0.36 | | | | | 0.64 |
| | | | | TBE_SP | TBE_EN | | | | | | | | |
| 1 | TT | | | 0.22 | 0.78 | | | | | | | | |
| 2 | TC | | | 0.36 | 0.64 | | | | | | | | |
| 3 | CC | | | 1.00 | 0.00 | | | | | | | | |

In which AA represents genotype TT,
AB represents genotype CT, and
BB represents genotype CC From Table 22 it can be seen that subjects with the genotype CC in MSTN_66493737 (T/C) SNP have the greatest chance of being sprinters given that they are elite Thoroughbreds.

MSTN Gene Expression

MSTN mRNA expression in two independent real-time qRT-PCR assays (Table 23) has been investigated in resting skeletal muscle (gluteus medius) from biopsy samples that had been collected for n=60 untrained yearlings (C/C, n=15; C/T, n=28; T/T, n=17).

TABLE 24

SNPs associated with best race distance

| CHR | SNP | STAT | EMP1 | NP |
|---|---|---|---|---|
| 18 | MSTN_66493737 | 36.63 | 1.00E−06 | 1000000 |
| 18 | MSTN_66494218 | 15.97 | 0.0001744 | 137586 |
| 22 | COX4I2_22684844 | 6.495 | 0.01146 | 2094 |
| 22 | COX4I2_22684390 | 5.783 | 0.02526 | 949 |

TABLE 23

Primer sequences for qRT-PCR assays for MSTN gene expression and TTN reference gene expression

| Primer Name | Target Gene | Location | Sequence |
|---|---|---|---|
| TTN_FOR | Titin (TTN) | Exon 357 | gcatgacacaactggaaagc (SEQ ID No. 38) |
| TTN_REV | Titin (TTN) | Exon 357 | aactttgccctcatcaatgc (SEQ ID No. 39) |
| MSTN1-2_FOR | Myostatin (MSTN) | Exon 1 | tgacagcagtgatggctctt (SEQ ID No. 40) |
| MSTN1-2_REV | Myostatin (MSTN) | Exon 2 | ttgggttttccttccacttg (SEQ ID No. 41) |
| MSTN2-3_FOR | Myostatin (MSTN) | Exon 2 | ttcccaagaccaggagaaga (SEQ ID No. 42) |
| MSTN2-3_REV | Myostatin (MSTN) | Exon 3 | cagcatcgagattctgtgga (SEQ ID No. 43) |

Figure 10:
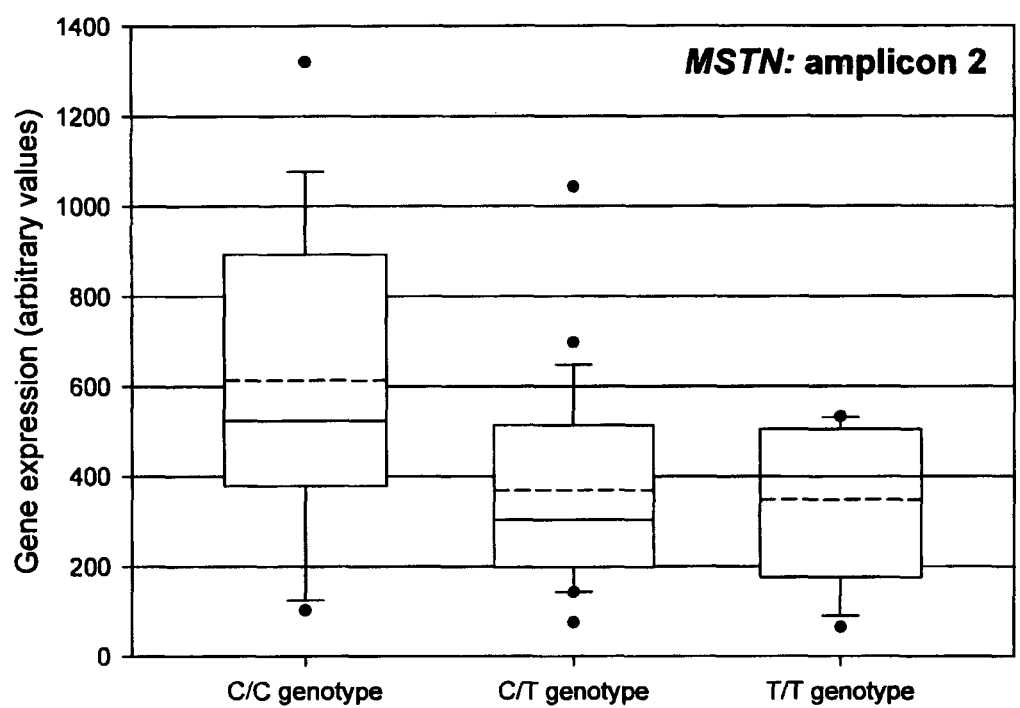
FIG. 10 is a graph showing the relative expression of MSTN gene for the MSTN 66493737 (T/C) SNP C/C, C/T and T/T genotypes.

We found a significant association with genotype for the MSTN 66493737 (T/C) SNP (P=0.003559). The C/C genotype cohort had higher MSTN mRNA levels (654.3±354.3; 613.7±327.0) than either of the C/T (405.7±234.1; 368.6±213.6) and T/T (350.1±185.5; 348.1±167.2) cohorts (FIG. 10).

It was also found that MSTN gene expression is significantly down-regulated (−4.2-fold, P=0.0043) following a period of training. In the Thoroughbred horse skeletal muscle transcriptome the greatest reduction in gene expression following a period of training is MSTN gene expression.

TABLE 24-continued

SNPs associated with best race distance

| CHR | SNP | STAT | EMP1 | NP |
|---|---|---|---|---|
| 22 | PTPN1_38585796 | 4.963 | 0.0377 | 609 |
| 4 | PON1_38697145 | 4.596 | 0.03938 | 583 |
| 22 | PTPN1_38597033 | 4.64 | 0.04406 | 521 |
| 22 | COX4I2_22684676 | 4.51 | 0.04742 | 484 |

Table 25 below shows the mean best race distance for each genotype for four of the SNPs from Table 24 above.

TABLE 25

Mean best race distance for each genotype

| CHR | SNP | VALUE | G11 | G12 | G22 |
|---|---|---|---|---|---|
| 18 | MSTN_66493737 | GENO | T/T | T/C | C/C |
| 18 | MSTN_66493737 | COUNTS | 12 | 46 | 21 |
| 18 | MSTN_66493737 | FREQ | 0.1519 | 0.5823 | 0.2658 |
| 18 | MSTN_66493737 | MEAN | 10.54 | 9.087 | 6.167 |
| 18 | MSTN_66493737 | SD | 2.742 | 2.365 | 0.8266 |
| 18 | MSTN_66494218 | GENO | C/C | C/A | A/A |
| 18 | MSTN_66494218 | COUNTS | 8 | 39 | 31 |
| 18 | MSTN_66494218 | FREQ | 0.1026 | 0.5 | 0.3974 |
| 18 | MSTN_66494218 | MEAN | 10.56 | 9.179 | 7.403 |
| 18 | MSTN_66494218 | SD | 2.872 | 2.48 | 2.043 |
| 22 | COX4I2_22684844 | GENO | C/C | C/T | T/T |
| 22 | COX4I2_22684844 | COUNTS | 4 | 39 | 40 |
| 22 | COX4I2_22684844 | FREQ | 0.04819 | 0.4699 | 0.4819 |
| 22 | COX4I2_22684844 | MEAN | 11.12 | 8.91 | 7.975 |
| 22 | COX4I2_22684844 | SD | 2.097 | 2.762 | 2.247 |
| 22 | COX4I2_22684390 | GENO | C/C | C/T | T/T |
| 22 | COX4I2_22684390 | COUNTS | 4 | 44 | 32 |
| 22 | COX4I2_22684390 | FREQ | 0.05 | 0.55 | 0.4 |
| 22 | COX4I2_22684390 | MEAN | 10.62 | 8.943 | 7.875 |
| 22 | COX4I2_22684390 | SD | 2.056 | 2.783 | 2.254 |

Wherein, at MSTN_66493737-(T/C) the TT genotype has a mean best race distance of 10.54 furlongs (f), the TC genotype has a mean best race distance of 9.087 f and the CC genotype has a mean best race distance of 6.167 f. Overall the mean best race distance was 8.55 f.

There are many practical applications for the genotypic test based on the MSTN genotype. These include:
1. Young stock (foals and yearlings)
Informed selection and sales decisions can be made to:
   identify sprinters
   identify middle-distance/potential Derby winners with speed
   identify individuals with enhanced stamina
2. Horses-in-training
Operating costs can be reduced and racing strategy can be fine tuned by:
   identifying the most precocious two-year olds
   horses can be trained and raced for optimal racing distance
3. Broodmares
Breeding outcomes can be optimised by:
   focusing on optimal breeding mares
   selecting compatible stallions
4. Stallions
A stallions potential can be promoted by:
   predicting stamina index for young stallions (5 year advantage)
   attracting compatible mares to enhance stallion profile For example, for the MSTN-66493737 T/C SNP for foals, young stock and horses-in-training selection of individuals may be made for individuals most likely to perform well as two year olds (C/C and C/T) and against 'backward' individuals (industry terminology for less physically developed young Thoroughbreds) that may benefit from waiting to race until they are three years old (T/T). Breeding objectives may be more confidently met by selecting C/C individuals for short distance racing, C/T individuals for middle-distance racing and T/T individuals for racing requiring greater stamina. For stallion owners, prediction of a stallion's genetic stamina index at the outset of a stud career (five years are required to estimate S.I. from retrospective three year old progeny racing performance) will immediately enhance a young stallion's profile and promote their genetic potential to mare owners. This in turn will enable mare owners, with targeted breeding strategies, to better select stallions to achieve specific breeding objectives. To eliminate uncertainty from a mating outcome (unless both sire and dam are homozygous) it will be necessary to genotype the foal, enabling selection of individuals for a targeted breeding outcome.

Example 6

Detecting SNPs

SNPs may be determined by any SNP genotyping method including for example the following non limiting methods:
Sequenom Inc
The iPLEX® Gold assay based on multiplex PCR followed by a single base primer extension reaction. After the PCR, remaining nucleotides are deactivated by SAP treatment. The single base primer extension step is performed, and the primer extension products analyzed using MALDI TOF MS.
KBiosciences
KBiosciences uses both its own novel form of competitive allele specific PCR system (KASPar) and Taqman™ chemistries for genotyping. KASPar assays are a proprietary in-house system developed to replace the previously used Amplifluor system.
Taqman Assays
TaqMan® SNP Genotyping Assays make it easy to perform SNP genotyping with the precision of TaqMan® reagent-based chemistry. TaqMan® Assays provide SNP detection capabilities. Also, the TaqMan® Sample-to-SNP™ Kit provides a streamlined protocol for performing TaqMan chemistry-based genotyping analysis from any sample with a single kit. The kit is comprised of two parts: the DNA Extract All Lysis Reagents and the TaqMan® GTXpress™ Master Mix. The DNA Extract All Lysis Reagents reduce prolonged procedures for the release of real-time PCR-ready DNA to a 5 minute protocol. They can process a wide variety of samples ranging from blood to buccal swabs. The TaqMan GTXpress Master Mix enables robust PCR amplification in less than 50 minutes.
Industrial Application
The predictive tests described herein may be applied to select individuals with high or low genetic potential for racing success. These tests can be performed on an individual at any stage in the life cycle e.g. Day 1 (birth), prior to sales (i.e.

yearlings, 2 year olds etc), during racing career (i.e. from 2 years old), during breeding (i.e. up to approx 25 years). Also, the tests may be applied to select appropriate stallion—mare matches for mating based on the genetic make-up of mare and stallion.

The invention is not limited to the embodiment hereinbefore described, with reference to the accompanying drawings, which may be varied in construction and detail.

REFERENCES

Ballard J. W. & Dean M. D. (2001) The mitochondrial genome: mutation, selection and recombination. *Curr Opin Genet Dev* 11, 667-72.

Blier P. U., Dufresne F. & Burton R. S. (2001) Natural selection and the evolution of mtDNA-encoded peptides: evidence for intergenomic co-adaptation. *Trends Genet* 17, 400-6.

Bray M S, Hagberg J M, Perusse L, Rankinen T, Roth S M, Wolfarth B, Bouchard C. The human gene map for performance and health-related fitness phenotypes: the 2006-2007 update. Med Sci Sports Exerc. 2009 January; 41(1): 35-73.

Cunningham E P, Dooley J J, Splan R K, Bradley D G. Microsatellite diversity, pedigree relatedness and the contributions of founder lineages to Thoroughbred horses. Anim Genet. 2001 December; 32(6):360-4.

Das J. (2006) The role of mitochondrial respiration in physiological and evolutionary adaptation. *Bioessays* 28, 890-901.

Dempsey and Wagner 1999 Exercise-induced arterial hypoxemia. J Appl Physiol. 1999 December; 87(6):1997-2006. Review. PMID: 10601141

Suzanne S. Eivers, Beatrice A. McGivney, Rita G. Fonseca, David E. MacHugh, Katie Menson, Stephen D. Park, Jose-Luis L. Rivero, Cormac T. Taylor, Lisa M. Katz and Emmeline W. Hill* Exercise-induced skeletal muscle gene expression in unconditioned and conditioned Thoroughbred horses and associations with physiological variables. *Physiological Genomics*, In Preparation (2009)

Martin Flack 2006 Functional, structural and molecular plasticity of mammalian skeletal muscle in response to exercise stimuli. The Journal of Experimental Biology 209, 2239-2248

Fukuda R, Zhang H, Kim J W, Shimoda L, Dang C V, Semenza G L. HIF-1 regulates cytochrome oxidase subunits to optimize efficiency of respiration in hypoxic cells. Cell. 2007 Apr. 6; 129(1):111-22.

Gordon D, Abajian C, Green P. Consed: a graphical tool for sequence finishing. Genome Res. 1998 March; 8(3):195-202.

Gramkow and Evans 2006 Gramkow H L, Evans D L. Correlation of race earnings with velocity at maximal heart rate during a field exercise test in Thoroughbred racehorses. Equine Vet J. Suppl. 2006 August; (36):118-22. PMID: 17402405

Gu J, On N, Park S D, Katz L M, Sulimova G, MacHugh D E, Hill E W. A genome scan for positive selection in thoroughbred horses. PLoS One. 2009 Jun. 2; 4(6):e5767.

Gunn H M. Muscle, bone and fat proportions and muscle distribution of thoroughbreds and quarter horses. In: Gillespie J R, Robinson N E eds. Equine exercise physiology 2. Davis, Calif.: ICEEP; 1987:253-264.

Harkins et al., 1993 Harkins J D, Hackett R P, Ducharme N G. Effect of furosemide on physiologic variables in exercising horses. Am J Vet Res. 1993 December; 54(12):2104-9. PMID: 8116946

Hoppeler and Vogt, 2001 Muscle tissue adaptations to hypoxia. J Exp Biol. 2001 September; 204(Pt 18):3133-9. Review. PMID: 11581327

Love S, Wyse C A, Stirk A J, Stear M J, Calver P, Voute L C, Mellor D J. Prevalence, heritability and significance of musculoskeletal conformational traits in Thoroughbred yearlings. Equine Vet J. 2006 November; 38(7):597-603. PMID: 17228572

Matoba S, Kang J G, Patino W D, Wragg A, Boehm M, Gavrilova O, Hurley P J, Bunz F, Hwang P M. p53 regulates mitochondrial respiration. Science. 2006 Jun. 16; 312 (5780):1650-3. Epub 2006 May 25.

Meiklejohn C. D., Montooth K. L. & Rand D. M. (2007) Positive and negative selection on the mitochondrial genome. Trends Genet 23, 259-63.

Mosher D S, Quignon P, Bustamante C D, Sutter N B, Mellersh C S, Parker H G, Ostrander E A. A mutation in the myostatin gene increases muscle mass and enhances racing performance in heterozygote dogs. PLoS Genet. 2007 May 25; 3(5):e79. Epub 2007 Apr. 30

Purcell S, Neale B, Todd-Brown K, Thomas L, Ferreira MAR, Bender D, Mailer J, Sklar P, de Bakker P I W, Daly M J & Sham P C (2007) PLINK: a toolset for whole-genome association and population-based linkage analysis. American Journal of Human Genetics, 81.

Revington M. Haematology of the racing Thoroughbred in Australia 2: haematological values compared to performance. Equine Vet J. 1983 April; 15(2):145-8. PMID: 6873047

Rivero J L, Ruz A, Marti-Korff S, Estepa J C, Aguilera-Tejero E, Werkman J, Sobotta M, Lindner A. Effects of intensity and duration of exercise on muscular responses to training of Thoroughbred racehorses. J Appl Physiol. 2007 May; 102(5):1871-82. Epub 2007 Jan. 25. PMID: 17255370

Saleem A, Adhihetty P J, Hood D A. Role of p53 in mitochondrial biogenesis and apoptosis in skeletal muscle. Physiol Genomics. 2009 Mar. 3; 37(1):58-66. Epub 2008 Dec. 23. Links Sambrook, J. and D. Russell (2001). Molecular Cloning; A Laboratory Manual, Cold Spring Harbor Laboratory.

Seaman J, Erickson B K, Kubo K, Hiraga A, Kai M, Yamaya Y, Wagner P D. Exercise induced ventilation/perfusion inequality in the horse. Equine Vet J. 1995 March; 27(2): 104-9. PMID: 7607141

Taylor C T, Colgan S P. Therapeutic targets for hypoxia-elicited pathways. Pharm Res. 1999 October; 16(10): 1498-505. Review. PMID: 10554089 van Deursen et al. 1993 Skeletal muscles of mice deficient in muscle creatine kinase lack burst activity Cell 74: 621-631

Weber K, Bruck P, Mikes Z, Kiipper J H, Klingenspor M, Wiesner R T. Glucocorticoid hormone stimulates mitochondrial biogenesis specifically in skeletal muscle. Endocrinology. 2002 January; 143(1):177-84.

Yang Q, Khoury M J, Botto L, Friedman J M, Flanders W D. Improving the prediction of complex diseases by testing for multiple disease-susceptibility genes. Am J Hum Genet. 2003 March; 72(3):636-49. Epub 2003 Feb. 14.

Young L E, Rogers K, Wood J L. Left ventricular size and systolic function in Thoroughbred racehorses and their relationships to race performance. J Appl Physiol. 2005 October; 99(4):1278-85. Epub 2005 May 26. PMID: 15920096

APPENDIX I

TBE (Elite) V TBO (non-winner) association test. SNPs raked by P value

| CHR | SNP | BP | A1 | F_A | F_U | A2 | CHISQ | P | OR |
|---|---|---|---|---|---|---|---|---|---|
| 4 | PDK4_38973231 | 3924 | A | 0.4639 | 0.2823 | G | 9.874 | 0.001676 | 2.2 |
| 4 | PDK4_38968139 | 0 | T | 0.4146 | 0.582 | C | 7.842 | 0.005106 | 0.5088 |
| 4 | PDK4_38969307 | 1168 | A | 0.4304 | 0.2712 | C | 7.409 | 0.006488 | 2.031 |
| 10 | CKM_15884567 | 2716 | C | 0.07407 | 0.1636 | A | 5.355 | 0.02066 | 0.4089 |
| 18 | MSTN_66493525 | 0 | G | 0.01205 | 0.05833 | T | 4.896 | 0.02692 | 0.1969 |
| 22 | COX4I2_22684390 | 1164 | C | 0.325 | 0.4545 | T | 4.654 | 0.03098 | 0.5778 |
| 22 | COX4I2_22684676 | 286 | C | 0.3415 | 0.4655 | T | 4.384 | 0.03628 | 0.5953 |
| 22 | COX4I2_22683226 | 6865 | T | 0.3636 | 0.4828 | G | 3.868 | 0.04922 | 0.6122 |
| 22 | ACSS1_759076 | 0 | A | 0.2317 | 0.1379 | C | 3.838 | 0.05009 | 1.885 |
| 3 | COX4I1_32772871 | 0 | T | 0.3642 | 0.2586 | C | 3.462 | 0.0628 | 1.642 |
| 9 | ADHFE1_18802749 | 66 | A | 0.03659 | 0.08197 | T | 2.728 | 0.0986 | 0.4253 |
| 18 | MSTN_66493775 | 30 | G | 0.01205 | 0.04167 | A | 2.559 | 0.1097 | 0.2805 |
| 25 | PTGS1_26007699 | 2168 | C | 0.1325 | 0.2016 | T | 2.494 | 0.1143 | 0.605 |
| 25 | PTGS1_25991437 | 1489 | C | 0.1098 | 0.175 | T | 2.49 | 0.1146 | 0.5812 |
| 22 | ACSS1_780613 | 12338 | C | 0.2625 | 0.3475 | T | 2.341 | 0.126 | 0.6685 |
| 1 | ACTN2_74842283 | 0 | G | 0.08537 | 0.1417 | A | 2.259 | 0.1329 | 0.5655 |
| 25 | GSN_25024464 | 0 | T | 0.09259 | 0.15 | A | 2.199 | 0.1381 | 0.5782 |
| 25 | GSN_25028755 | 4291 | A | 0.0875 | 0.1441 | G | 2.193 | 0.1386 | 0.5697 |
| 10 | CKM_15887661 | 3094 | C | 0.3025 | 0.386 | T | 2.088 | 0.1485 | 0.6899 |
| 1 | GGPS1_76001872 | 0 | A | 0.439 | 0.3559 | C | 1.967 | 0.1607 | 1.416 |
| 22 | PTPN1_38591965 | 1580 | C | 0.3025 | 0.3814 | A | 1.905 | 0.1675 | 0.7034 |
| 4 | ACN9_40285196 | 5470 | G | 0.3861 | 0.3083 | T | 1.806 | 0.179 | 1.411 |
| 1 | TOMM20_76186624 | 1936 | C | 0.2062 | 0.2727 | T | 1.61 | 0.2044 | 0.6929 |
| 4 | ACN9_40267593 | 0 | A | 0.02907 | 0.008065 | T | 1.601 | 0.2058 | 3.683 |
| 18 | MSTN_66493745 | 8 | G | 0.01765 | 0.04237 | A | 1.577 | 0.2092 | 0.406 |
| 21 | PRKAA1_25374247 | 9959 | A | 0.04321 | 0.01667 | G | 1.572 | 0.2099 | 2.665 |
| 22 | COX4I2-5900_22676361 | 0 | C | 0.4259 | 0.5 | T | 1.495 | 0.2215 | 0.7419 |
| 9 | ADHFE1_18793538 | 5477 | C | 0.142 | 0.1949 | T | 1.394 | 0.2378 | 0.6835 |
| 9 | ADHFE1_18802683 | 9145 | G | 0.05696 | 0.09322 | A | 1.321 | 0.2504 | 0.5876 |
| 1 | GGPS1_76002021 | 149 | C | 0.4304 | 0.3644 | A | 1.223 | 0.2688 | 1.318 |
| 10 | CKM_15881851 | 0 | A | 0.06329 | 0.0339 | G | 1.212 | 0.2709 | 1.926 |
| 18 | MSTN_66494218 | 443 | C | 0.3526 | 0.2895 | A | 1.193 | 0.2747 | 1.337 |
| 1 | ACTN2_74900867 | 19039 | T | 0.0625 | 0.09821 | A | 1.179 | 0.2775 | 0.6121 |
| 25 | TNC_19737599 | 6101 | C | 0.4145 | 0.4815 | G | 1.149 | 0.2837 | 0.7623 |
| 22 | PTPN1_38585796 | 0 | G | 0.1975 | 0.25 | C | 1.106 | 0.2929 | 0.7385 |
| 1 | MYEF2_141647593 | 20636 | T | 0.1456 | 0.1034 | C | 1.065 | 0.302 | 1.477 |
| 9 | MTFR1_19456942 | 17072 | A | 0.04819 | 0.07627 | T | 0.9663 | 0.3256 | 0.6132 |
| 1 | MYEF2_141651362 | 394 | A | 0.141 | 0.1017 | G | 0.9562 | 0.3282 | 1.45 |
| 9 | MTFR1_19472498 | 15556 | A | 0.05422 | 0.08333 | G | 0.9521 | 0.3292 | 0.6306 |
| 24 | HIF1A_8984849 | 4922 | G | 0.1582 | 0.2034 | A | 0.9436 | 0.3314 | 0.7362 |
| 25 | GSN_25033440 | 4685 | G | 0.3916 | 0.3361 | A | 0.9313 | 0.3345 | 1.271 |
| 1 | ACTN2_74853540 | 11257 | T | 0.2785 | 0.2288 | G | 0.8721 | 0.3504 | 1.301 |
| 1 | ACTN2_74872377 | 18837 | G | 0.09494 | 0.1293 | T | 0.8106 | 0.3679 | 0.7063 |
| 25 | TNC_19737816 | 217 | A | 0.425 | 0.475 | G | 0.6937 | 0.4049 | 0.8169 |
| 9 | ADHFE1_18787798 | 2714 | G | 0.03205 | 0.05172 | A | 0.6635 | 0.4153 | 0.6071 |
| 22 | MC3R-530_43059660 | 0 | C | 0.2692 | 0.3148 | T | 0.6469 | 0.4212 | 0.8019 |
| 1 | MYEF2_141626957 | 0 | C | 0.1386 | 0.1083 | T | 0.5781 | 0.447 | 1.324 |
| 1 | TOMM20_76184688 | 0 | T | 0.3253 | 0.2833 | A | 0.5759 | 0.4479 | 1.22 |
| 25 | PTGS1_25989948 | 0 | C | 0.1392 | 0.1724 | T | 0.5672 | 0.4514 | 0.7765 |
| 25 | TNC_19741797 | 3981 | C | 0.3036 | 0.2564 | G | 0.5027 | 0.4783 | 1.264 |
| 25 | TNC_19716930 | 0 | G | 0.09375 | 0.1167 | A | 0.3879 | 0.5334 | 0.7833 |
| 1 | MYEF2_141650968 | 3375 | C | 0.1341 | 0.1102 | T | 0.3629 | 0.5469 | 1.251 |
| 4 | PON1_38681590 | 784 | T | 0.08537 | 0.06667 | C | 0.3391 | 0.5604 | 1.307 |
| 25 | NDUFA8_25799774 | 680 | T | 0.5064 | 0.4712 | C | 0.3103 | 0.5775 | 1.152 |
| 21 | PRKAA1_25364288 | 0 | A | 0.03659 | 0.025 | G | 0.3031 | 0.5819 | 1.481 |
| 4 | PON1_38680806 | 0 | A | 0.1098 | 0.09016 | G | 0.2947 | 0.5872 | 1.244 |
| 25 | NDUFA8_25799094 | 3431 | G | 0.4661 | 0.5 | T | 0.2544 | 0.614 | 0.873 |
| 9 | MTFR1_19439870 | 129 | G | 0.3072 | 0.2807 | A | 0.228 | 0.633 | 1.136 |
| 1 | ACTN2_74881828 | 9451 | C | 0.275 | 0.25 | T | 0.2204 | 0.6387 | 1.138 |
| 4 | PON1_38693816 | 12226 | A | 0.1084 | 0.09167 | G | 0.2149 | 0.643 | 1.205 |
| 25 | UGCG_16689693 | 0 | T | 0.3494 | 0.375 | C | 0.1981 | 0.6562 | 0.8951 |
| 24 | HIF1A_8973233 | 0 | C | 0.3293 | 0.3534 | A | 0.1772 | 0.6738 | 0.898 |
| 1 | ACTA1+50243_68459659 | 50311 | C | 0.4634 | 0.4407 | T | 0.1431 | 0.7052 | 1.096 |
| 25 | NDUFA8_25801538 | 1764 | C | 0.4872 | 0.5086 | T | 0.1223 | 0.7265 | 0.9178 |
| 25 | NDUFA8_25795663 | 0 | A | 0.4873 | 0.5085 | G | 0.1207 | 0.7283 | 0.9189 |
| 25 | PTGS1_26005531 | 14094 | T | 0.4444 | 0.4237 | C | 0.1192 | 0.7299 | 1.088 |
| 4 | PON1_38697145 | 3329 | T | 0.07738 | 0.06667 | C | 0.1189 | 0.7303 | 1.174 |
| 22 | PTPN1_38590385 | 4589 | A | 0.3063 | 0.325 | C | 0.1119 | 0.738 | 0.9168 |
| 9 | ADHFE1_18788061 | 263 | C | 0.04938 | 0.05833 | T | 0.1097 | 0.7405 | 0.8386 |
| 24 | HIF1A_8979927 | 6694 | G | 0.175 | 0.1897 | A | 0.09736 | 0.755 | 0.9063 |
| 1 | TOMM20_76191732 | 5108 | T | 0.4337 | 0.4153 | C | 0.09633 | 0.7563 | 1.079 |
| 18 | MSTN_66493737 | 212 | T | 0.443 | 0.425 | C | 0.09028 | 0.7638 | 1.076 |
| 22 | ACSS1_762559 | 120 | A | 0.4767 | 0.4597 | T | 0.08426 | 0.7716 | 1.071 |
| 1 | ACTA1_68409348 | 0 | C | 0.1524 | 0.1404 | T | 0.07816 | 0.7798 | 1.102 |
| 9 | MTFR1_19439741 | 0 | A | 0.3086 | 0.2931 | G | 0.0774 | 0.7808 | 1.077 |
| 25 | UGCG_16710063 | 178 | G | 0.08537 | 0.07627 | C | 0.07577 | 0.7831 | 1.13 |

APPENDIX I-continued

TBE (Elite) V TBO (non-winner) association test. SNPs raked by P value

| CHR | SNP | BP | A1 | F_A | F_U | A2 | CHISQ | P | OR |
|---|---|---|---|---|---|---|---|---|---|
| 4 | ACN9_40305424 | 20228 | T | 0.2831 | 0.2966 | G | 0.06101 | 0.8049 | 0.9366 |
| 4 | ACN9_40279726 | 12133 | C | 0.3291 | 0.3421 | T | 0.0502 | 0.8227 | 0.9434 |
| 22 | PTPN1_38597033 | 5068 | T | 0.2615 | 0.2745 | C | 0.04911 | 0.8246 | 0.936 |
| 1 | MYEF2_141653617 | 2255 | T | 0.4177 | 0.4068 | G | 0.03336 | 0.8551 | 1.046 |
| 25 | UGCG_16709885 | 20192 | G | 0.3812 | 0.3917 | A | 0.0314 | 0.8593 | 0.957 |
| 22 | ACSS1_762439 | 0 | G | 0.4753 | 0.4831 | A | 0.0164 | 0.8981 | 0.9695 |
| 22 | COX4I2_22684844 | 168 | C | 0.2831 | 0.2881 | T | 0.008468 | 0.9267 | 0.9758 |
| 9 | ADHFE1_18785084 | 0 | T | 0.05921 | 0.06122 | C | 0.004285 | 0.9478 | 0.965 |
| 22 | ACSS1_768275 | 5716 | T | 0.07407 | 0.075 | G | 0.000858 | 0.9766 | 0.9867 |
| 25 | TNC_19731498 | 14568 | G | 0.3214 | 0 | T | 7.193 | 0.007319 | NA |

APPENDIX II

TBE_SP (elites printer) V TBE_EN (elite stayer) association test. SNPs raked by P value

| CHR | SNP | BP | A1 | F_A | F_U | A2 | CHISQ | P | OR |
|---|---|---|---|---|---|---|---|---|---|
| 18 | MSTN_66493737 | 212 | T | 0.2821 | 0.6406 | C | 18.31 | 1.88E−05 | 0.2204 |
| 18 | MSTN_66494218 | 443 | C | 0.2368 | 0.4844 | A | 9.357 | 0.002221 | 0.3304 |
| 4 | ACN9_40279726 | 12133 | C | 0.4079 | 0.25 | T | 4.026 | 0.0448 | 2.067 |
| 22 | PTPN1_38585796 | 0 | G | 0.225 | 0.1029 | C | 3.901 | 0.04826 | 2.53 |
| 22 | COX4I2_22684844 | 168 | C | 0.2195 | 0.3529 | T | 3.283 | 0.07001 | 0.5156 |
| 22 | PTPN1_38597033 | 5068 | T | 0.2931 | 0.1552 | C | 3.173 | 0.07488 | 2.257 |
| 4 | PON1_38697145 | 3329 | T | 0.04878 | 0.1286 | C | 3.074 | 0.07955 | 0.3476 |
| 22 | COX4I2-5900_22676361 | 0 | C | 0.359 | 0.5 | T | 2.957 | 0.0855 | 0.56 |
| 22 | COX4I2_22684390 | 1164 | C | 0.2692 | 0.3971 | T | 2.69 | 0.101 | 0.5595 |
| 4 | ACN9_40305424 | 20228 | G | 0.3415 | 0.2206 | G | 2.656 | 0.1032 | 1.832 |
| 1 | MYEF2_141650968 | 3375 | C | 0.0875 | 0.1765 | T | 2.6 | 0.1068 | 0.4475 |
| 18 | MSTN_66493525 | 0 | G | 0 | 0.02941 | T | 2.444 | 0.1179 | 0 |
| 18 | MSTN_66493775 | 30 | G | 0 | 0.02941 | A | 2.444 | 0.1179 | 0 |
| 25 | UGCG_16710063 | 178 | A | 0.05 | 0.1176 | G | 2.258 | 0.133 | 0.3947 |
| 9 | ADHFE1_18787798 | 2714 | G | 0.01351 | 0.06061 | A | 2.246 | 0.1339 | 0.2123 |
| 10 | CKM_15884567 | 2716 | G | 0.05128 | 0.1176 | A | 2.121 | 0.1453 | 0.4054 |
| 4 | PON1_38681590 | 784 | T | 0.0625 | 0.1324 | C | 2.094 | 0.1479 | 0.437 |
| 1 | MYEF2_141626957 | 0 | C | 0.09756 | 0.1765 | T | 2.003 | 0.157 | 0.5045 |
| 25 | GSN_25028755 | 4291 | A | 0.05263 | 0.1176 | G | 1.986 | 0.1588 | 0.4167 |
| 22 | COX4I2_22683226 | 6865 | T | 0.3108 | 0.4242 | G | 1.938 | 0.1639 | 0.612 |
| 1 | MYEF2_141651362 | 394 | G | 0.09722 | 0.1765 | A | 1.872 | 0.1712 | 0.5026 |
| 25 | GSN_25024464 | 0 | T | 0.05263 | 0.1143 | A | 1.836 | 0.1754 | 0.4306 |
| 24 | HIF1A_8984849 | 4922 | G | 0.1053 | 0.1818 | A | 1.711 | 0.1909 | 0.5294 |
| 4 | ACN9_40267593 | 0 | A | 0.01163 | 0.04286 | T | 1.506 | 0.2197 | 0.2627 |
| 22 | PTPN1_38590385 | 4589 | A | 0.2692 | 0.3636 | C | 1.483 | 0.2233 | 0.6447 |
| 1 | MYEF2_141653617 | 2255 | T | 0.3553 | 0.4545 | G | 1.449 | 0.2287 | 0.6612 |
| 4 | PON1_38693816 | 12226 | A | 0.08537 | 0.1471 | G | 1.408 | 0.2354 | 0.5413 |
| 22 | COX4I2_22684676 | 286 | C | 0.3049 | 0.3971 | T | 1.395 | 0.2376 | 0.666 |
| 1 | MYEF2_141647593 | 20636 | T | 0.1081 | 0.1765 | C | 1.369 | 0.2421 | 0.5657 |
| 4 | PON1_38680806 | 0 | A | 0.0875 | 0.1471 | G | 1.282 | 0.2574 | 0.5562 |
| 25 | TNC_19737599 | 6101 | A | 0.4583 | 0.3636 | G | 1.274 | 0.2591 | 1.481 |
| 10 | CKM_15887661 | 3094 | C | 0.2692 | 0.3529 | T | 1.194 | 0.2745 | 0.6754 |
| 1 | ACTA1+50243_68459659 | 50311 | C | 0.425 | 0.5147 | T | 1.189 | 0.2756 | 0.6969 |
| 9 | ADHFE1_18802749 | 66 | A | 0.025 | 0.05882 | T | 1.081 | 0.2985 | 0.4103 |
| 9 | MTFR1_19456942 | 17072 | A | 0.03659 | 0.07353 | C | 1.005 | 0.3161 | 0.4785 |
| 24 | HIF1A_8979927 | 6694 | G | 0.1316 | 0.1912 | A | 0.9498 | 0.3298 | 0.641 |
| 1 | ACTN2_74900867 | 19039 | T | 0.03846 | 0.07576 | A | 0.9478 | 0.3303 | 0.488 |
| 25 | TNC_19737816 | 217 | A | 0.4605 | 0.3824 | G | 0.8982 | 0.3433 | 1.379 |
| 22 | PTPN1_38591965 | 1580 | C | 0.3125 | 0.2424 | T | 0.8793 | 0.3484 | 1.42 |
| 9 | ADHFE1_18802683 | 9145 | G | 0.08108 | 0.04412 | A | 0.8156 | 0.3665 | 1.912 |
| 25 | PTGS1_25991437 | 1489 | C | 0.0875 | 0.1324 | T | 0.7669 | 0.3812 | 0.6286 |
| 21 | PRKAA1_25364288 | 0 | A | 0.0375 | 0.01471 | G | 0.7262 | 0.3941 | 2.61 |
| 21 | PRKAA1_25374247 | 9959 | A | 0.0375 | 0.01515 | G | 0.6779 | 0.4103 | 2.532 |
| 9 | ADHFE1_18793538 | 5477 | C | 0.1282 | 0.1765 | T | 0.6613 | 0.4161 | 0.6863 |
| 1 | GGPS1_76001872 | 0 | A | 0.4756 | 0.4091 | C | 0.6549 | 0.4184 | 1.31 |
| 18 | MSTN_66493745 | 8 | G | 0.01163 | 0.02941 | A | 0.6288 | 0.4278 | 0.3882 |
| 1 | TOMM20_76186624 | 1936 | A | 0.175 | 0.2273 | T | 0.6208 | 0.4307 | 0.7212 |
| 25 | GSN_25033440 | 4685 | G | 0.378 | 0.4412 | A | 0.614 | 0.4333 | 0.7699 |
| 4 | PDK4_38969307 | 1168 | A | 0.3919 | 0.4559 | C | 0.5947 | 0.4406 | 0.7692 |
| 9 | MTFR1_19439741 | 0 | A | 0.3375 | 0.2794 | G | 0.579 | 0.4467 | 1.314 |
| 9 | ADHFE1_18785084 | 0 | T | 0.07895 | 0.04839 | C | 0.5231 | 0.4695 | 1.686 |
| 22 | ACSS1_780613 | 12338 | C | 0.3026 | 0.25 | T | 0.4955 | 0.4815 | 1.302 |
| 22 | ACSS1_762559 | 120 | A | 0.5116 | 0.4571 | T | 0.4585 | 0.4983 | 1.244 |
| 9 | MTFR1_19472498 | 15556 | A | 0.04878 | 0.07353 | G | 0.4037 | 0.5252 | 0.6462 |
| 25 | PTGS1_26007699 | 2168 | C | 0.122 | 0.1571 | T | 0.3928 | 0.5308 | 0.7449 |
| 1 | GGPS1_76002021 | 149 | C | 0.4605 | 0.4091 | A | 0.3799 | 0.5376 | 1.233 |

APPENDIX II-continued

TBE_SP (elites printer) V TBE_EN (elite stayer) association test. SNPs raked by P value

| CHR | SNP | BP | A1 | F_A | F_U | A2 | CHISQ | P | OR |
|---|---|---|---|---|---|---|---|---|---|
| 1 | ACTN2_74853540 | 11257 | T | 0.3026 | 0.2576 | G | 0.3544 | 0.5516 | 1.251 |
| 25 | UGCG_16709885 | 20192 | G | 0.4189 | 0.3714 | A | 0.3392 | 0.5603 | 1.22 |
| 3 | COX4I1_32772871 | 0 | T | 0.3846 | 0.3382 | C | 0.338 | 0.561 | 1.223 |
| 9 | MTFR1_19439870 | 129 | G | 0.2805 | 0.3235 | A | 0.3279 | 0.5669 | 0.8151 |
| 25 | UGCG_16689693 | 0 | T | 0.3659 | 0.3235 | C | 0.294 | 0.5877 | 1.206 |
| 25 | TNC_19741797 | 3981 | C | 0.2778 | 0.3261 | G | 0.2761 | 0.5993 | 0.7949 |
| 1 | ACTA1_68409348 | 0 | C | 0.1625 | 0.1324 | T | 0.264 | 0.6074 | 1.272 |
| 25 | TNC_19731498 | 14568 | G | 0.35 | 0.25 | T | 0.262 | 0.6088 | 1.615 |
| 1 | ACTN2_74881828 | 9451 | C | 0.2875 | 0.2576 | T | 0.1628 | 0.6866 | 1.163 |
| 4 | PDK4_38973231 | 3924 | A | 0.439 | 0.4706 | G | 0.1494 | 0.6991 | 0.8804 |
| 22 | MC3R-530_43059660 | 0 | C | 0.2692 | 0.2424 | T | 0.1346 | 0.7138 | 1.151 |
| 22 | ACSS1_762439 | 0 | G | 0.5 | 0.4697 | A | 0.1329 | 0.7154 | 1.129 |
| 24 | HIF1A_8973233 | 0 | C | 0.3125 | 0.3382 | A | 0.1111 | 0.7389 | 0.8893 |
| 4 | PDK4_38968139 | 0 | T | 0.4375 | 0.4118 | C | 0.09958 | 0.7523 | 1.111 |
| 4 | ACN9_40285196 | 5470 | G | 0.3684 | 0.3939 | T | 0.09761 | 0.7547 | 0.8974 |
| 1 | TOMM20_76191732 | 5108 | T | 0.4512 | 0.4265 | C | 0.09241 | 0.7611 | 1.106 |
| 25 | TNC_19716930 | 0 | G | 0.07692 | 0.09091 | A | 0.09154 | 0.7622 | 0.8333 |
| 1 | ACTN2_74842283 | 0 | G | 0.075 | 0.08824 | A | 0.08642 | 0.7688 | 0.8378 |
| 22 | ACSS1_759076 | 0 | G | 0.2375 | 0.2206 | C | 0.05941 | 0.8074 | 1.101 |
| 25 | PTGS1_25989948 | 0 | C | 0.1351 | 0.1471 | T | 0.04164 | 0.8383 | 0.9062 |
| 9 | ADHFE1_18788061 | 263 | C | 0.05128 | 0.05882 | T | 0.03989 | 0.8417 | 0.8649 |
| 25 | NDUFA8_25799094 | 3431 | G | 0.4833 | 0.5 | T | 0.02746 | 0.8684 | 0.9355 |
| 25 | NDUFA8_25801538 | 1764 | C | 0.5135 | 0.5 | T | 0.02549 | 0.8732 | 1.056 |
| 25 | NDUFA8_25795663 | 0 | A | 0.5132 | 0.5 | G | 0.02486 | 0.8747 | 1.054 |
| 22 | ACSS1_768275 | 5716 | T | 0.07895 | 0.08571 | A | 0.02212 | 0.8818 | 0.9143 |
| 10 | CKM_15881851 | 0 | A | 0.06757 | 0.07353 | G | 0.01924 | 0.8897 | 0.913 |
| 1 | ACTN2_74872377 | 18837 | G | 0.09459 | 0.08824 | T | 0.01723 | 0.8956 | 1.08 |
| 1 | TOMM20_76184688 | 0 | T | 0.3333 | 0.3235 | A | 0.01636 | 0.8982 | 1.045 |
| 25 | PTGS1_26005531 | 14094 | T | 0.4625 | 0.4559 | C | 0.006481 | 0.9358 | 1.027 |
| 25 | NDUFA8_25799774 | 680 | T | 0.4865 | 0.4853 | C | 0.000202 | 0.9887 | 1.005 |

APPENDIX III

Significant associations between SNP and phenotype
TBE - elite (Group race winning) Thoroughbred
TBO - other (non-winning) Thoroughbred
TBE_SP8 - elite (Group race winning) Thoroughbred that won best race over a distance <8 f
TBE_SP7 - elite (Group race winning) Thoroughbred that won best race over a distance <7 f
TBE_EN - elite (Group race winning) Thoroughbred that won best race over a distance >8 f
SNPs are given by GeneSymbol_chromosomeposition(bp)

| | P | OR |
|---|---|---|
| TBE V TBO | | |
| PDK4_38973231 | 0.001676 | 2.2 |
| CKM_15884567 | 0.02066 | 0.4089 |
| COX4I2_22684390 | 0.03098 | 0.5778 |
| TBE SP8 V TBE EN | | |
| PON1_38697145 | 0.03584 | 0.2884 |
| PTPN1_38585796 | 0.01011 | 3.157 |
| MSTN_66493737 | 3.70E−05 | 0.2503 |
| TBE SP7 V TBE EN | | |
| ACN9_40279726 | 0.0448 | 2.067 |
| PTPN1_38585796 | 0.04826 | 2.53 |
| MSTN_66493737 | 1.88E−05 | 0.2204 |
| TBE EN V TBO | | |
| PDK4_38973231 | 0.008833 | 2.26 |
| PTPN1_38585796 | 0.01482 | 0.3443 |
| MSTN_66493737 | 0.005334 | 2.412 |
| TBE SP8 V TBO | | |
| ADHFE1_18802749 | 0.04945 | 0.2383 |
| PDK4_38973231 | 0.006401 | 2.159 |
| CKM_15884567 | 0.00545 | 0.2272 |
| COX4I2_22684390 | 0.007404 | 0.4478 |
| P-TBE SP7 V TBO | | |
| GSN_25024464 | 0.03537 | 0.3148 |
| PDK4_38973231 | 0.02048 | 1.99 |
| MSTN_66493737 | 0.04163 | 0.5315 |
| CKM_15884567 | 0.01821 | 0.2763 |
| COX4I2_22684390 | 0.009814 | 0.4421 |
| P TBE V TBO males | | |
| ACTN2_74842283 | 0.04372 | 0.308 |
| PDK4_38973231 | 0.003429 | 3.4 |
| PTGS1_26007699 | 0.005124 | 0.2174 |
| PTPN1_38590385 | 0.03461 | 0.3966 |
| COX4I1_32772871 | 0.04415 | 2.229 |

APPENDIX IV

Case control association test and best fit model for significantly associated SNPs
TBE V TBO (Case-control association test) P < 0.05

| CHR | SNP | BP | A1 | F_A | F_U | A2 | CHISQ | P | OR |
|---|---|---|---|---|---|---|---|---|---|
| 4 | PDK4_38973231 | 3924 | A | 0.4639 | 0.2823 | G | 9.874 | 0.001676 | 2.2 |
| 4 | PDK4_38968139 | 0 | T | 0.4146 | 0.582 | C | 7.842 | 0.005106 | 0.5088 |
| 4 | PDK4_38969307 | 1168 | A | 0.4304 | 0.2712 | C | 7.409 | 0.006488 | 2.031 |
| 10 | CKM_15884567 | 2716 | G | 0.07407 | 0.1636 | A | 5.355 | 0.02066 | 0.4089 |
| 18 | MSTN_66493525 | 0 | G | 0.01205 | 0.05833 | T | 4.896 | 0.02692 | 0.1969 |
| 22 | COX4I2_22684390 | 1164 | C | 0.325 | 0.4545 | T | 4.654 | 0.03098 | 0.5778 |
| 22 | COX4I2_22684676 | 286 | C | 0.3415 | 0.4655 | T | 4.384 | 0.03628 | 0.5953 |
| 22 | COX4I2_22683226 | 6865 | T | 0.3636 | 0.4828 | G | 3.868 | 0.04922 | 0.6122 |
| 22 | ACSS1_759076 | 0 | G | 0.2317 | 0.1379 | C | 3.838 | 0.05009 | 1.885 |

TBE V TBO Best-fit Model for significantly associated SNPs

| CHR | SNP | A1 | A2 | TEST | AFF | UNAFF | CHISQ | DF | P |
|---|---|---|---|---|---|---|---|---|---|
| 4 | PDK4_38973231 | A | G | ALLELIC | 77/89 | 35/89 | 9.874 | 1 | 0.001676 |
| 4 | PDK4_38973231 | A | G | TREND | 77/89 | 35/89 | 9.237 | 1 | 0.002372 |
| 4 | PDK4_38973231 | A | G | DOM | 59/24 | 29/33 | 8.791 | 1 | 0.003027 |
| 4 | PDK4_38973231 | A | G | GENO | 18/41/24 | 6/23/33 | 9.644 | 2 | 0.008049 |
| 4 | PDK4_38973231 | A | G | REC | 18/65 | 6/56 | 3.706 | 1 | 0.05422 |
| 4 | PDK4_38968139 | T | C | ALLELIC | 68/96 | 71/51 | 7.842 | 1 | 0.005106 |
| 4 | PDK4_38968139 | T | C | TREND | 68/96 | 71/51 | 6.841 | 1 | 0.008907 |
| 4 | PDK4_38968139 | T | C | REC | 16/66 | 23/38 | 5.837 | 1 | 0.01569 |
| 4 | PDK4_38968139 | T | C | GENO | 16/36/30 | 23/25/13 | 7.029 | 2 | 0.02977 |
| 4 | PDK4_38968139 | T | C | DOM | 52/30 | 48/13 | 3.881 | 1 | 0.04884 |
| 4 | PDK4_38969307 | A | C | DOM | 54/25 | 26/33 | 8.177 | 1 | 0.004243 |
| 4 | PDK4_38969307 | A | C | ALLELIC | 68/90 | 32/86 | 7.409 | 1 | 0.006488 |
| 4 | PDK4_38969307 | A | C | TREND | 68/90 | 32/86 | 6.996 | 1 | 0.008169 |
| 4 | PDK4_38969307 | A | C | GENO | 14/40/25 | 6/20/33 | 8.245 | 2 | 0.01621 |
| 4 | PDK4_38969307 | A | C | REC | 14/65 | 19511 | 1.554 | 1 | 0.2125 |
| 10 | CKM_15884567 | G | A | ALLELIC | 12/150 | 18/92 | 5.355 | 1 | 0.02066 |
| 10 | CKM_15884567 | G | A | DOM | 11/70 | 16/39 | 4.953 | 1 | 0.02605 |
| 10 | CKM_15884567 | G | A | TREND | 12/150 | 18/92 | 4.865 | 1 | 0.02741 |
| 10 | CKM_15884567 | G | A | GENO | 1/10/70 | 2/14/39 | 5.03 | 2 | 0.08087 |
| 10 | CKM_15884567 | G | A | REC | 1/80 | 2/53 | 0.876 | 1 | 0.3493 |
| 18 | MSTN_66493525 | G | T | ALLELIC | 2/164 | 7/113 | 4.896 | 1 | 0.02692 |
| 18 | MSTN_66493525 | G | T | TREND | 2/164 | 7/113 | 3.432 | 1 | 0.06394 |
| 18 | MSTN_66493525 | G | T | REC | 0/83 | 21217 | 2.806 | 1 | 0.09392 |
| 18 | MSTN_66493525 | G | T | DOM | 29618 | 20210 | 2.625 | 1 | 0.1052 |
| 18 | MSTN_66493525 | G | T | GENO | 0/2/81 | 20150 | 3.563 | 2 | 0.1683 |
| 22 | COX4I2_22684390 | C | T | REC | 4/76 | 10/45 | 6.093 | 1 | 0.01357 |
| 22 | COX4I2_22684390 | C | T | TREND | 52/108 | 50/60 | 5.58 | 1 | 0.01817 |
| 22 | COX4I2_22684390 | C | T | GENO | 4/44/32 | 10/30/15 | 6.979 | 2 | 0.03052 |
| 22 | COX4I2_22684390 | C | T | ALLELIC | 52/108 | 50/60 | 4.654 | 1 | 0.03098 |
| 22 | COX4I2_22684390 | C | T | DOM | 48/32 | 40/15 | 2.326 | 1 | 0.1272 |
| 22 | COX4I2_22684676 | C | T | REC | 28246 | 17472 | 5.557 | 1 | 0.01841 |
| 22 | COX4I2_22684676 | C | T | TREND | 56/108 | 54/62 | 5.268 | 1 | 0.02172 |
| 22 | COX4I2_22684676 | C | T | ALLELIC | 56/108 | 54/62 | 4.384 | 1 | 0.03628 |
| 22 | COX4I2_22684676 | C | T | GENO | 5/46/31 | 11/32/15 | 6.402 | 2 | 0.04072 |
| 22 | COX4I2_22684676 | C | T | DOM | 51/31 | 43/15 | 2.196 | 1 | 0.1383 |
| 22 | COX4I2_22683226 | T | G | REC | 26420 | 17137 | 6.057 | 1 | 0.01385 |
| 22 | COX4I2_22683226 | T | G | TREND | 56/98 | 56/60 | 4.776 | 1 | 0.02887 |
| 22 | COX4I2_22683226 | T | G | GENO | 5/46/26 | 12/32/14 | 6.449 | 2 | 0.03978 |
| 22 | COX4I2_22683226 | T | G | ALLELIC | 56/98 | 56/60 | 3.868 | 1 | 0.04922 |
| 22 | COX4I2_22683226 | T | G | DOM | 51/26 | 44/14 | 1.471 | 1 | 0.2252 |
| 22 | ACSS1_759076 | G | C | DOM | 35/47 | 15/43 | 4.187 | 1 | 0.04075 |
| 22 | ACSS1_759076 | G | C | TREND | 38/126 | 16/100 | 4.063 | 1 | 0.04382 |
| 22 | ACSS1_759076 | G | C | ALLELIC | 38/126 | 16/100 | 3.838 | 1 | 0.05009 |
| 22 | ACSS1_759076 | G | C | GENO | 3/32/47 | 1/14/43 | 4.231 | 2 | 0.1206 |
| 22 | ACSS1_759076 | G | C | REC | 28915 | 20821 | 0.458 | 1 | 0.4986 |

TBE SP7 V TBE EN (Case-control association test) P < 0.05

| CHR | SNP | BP | A1 | F_A | F_U | A2 | CHISQ | P | OR |
|---|---|---|---|---|---|---|---|---|---|
| 18 | MSTN_66493737 | 212 | T | 0.2821 | 0.6406 | C | 18.31 | 1.88E−05 | 4.54 |
| 18 | MSTN_66494218 | 443 | C | 0.2368 | 0.4844 | A | 9.357 | 0.002221 | |
| 4 | ACN9_40279726 | 12133 | C | 0.4079 | 0.25 | T | 4.026 | 0.0448 | 2.067 |
| 22 | PTPN1_38585796 | 0 | G | 0.225 | 0.1029 | C | 3.901 | 0.04826 | 2.53 |

TBE SP7 V TB EN Best-fit Model for significantly associated SNPs

| CHR | SNP | A1 | A2 | TEST | AFF | UNAFF | CHISQ | DF | P |
|---|---|---|---|---|---|---|---|---|---|
| 18 | MSTN_66493737 | T | C | GENO | 3/16/20 | 9/23/0 | 23.8 | 2 | 6.80E−06 |
| 18 | MSTN_66493737 | T | C | TREND | 22/56 | 41/23 | 20.64 | 1 | 5.55E−06 |
| 18 | MSTN_66493737 | T | C | ALLELIC | 22/56 | 41/23 | 18.31 | 1 | 1.88E−05 |
| 18 | MSTN_66493737 | T | C | DOM | 19/20 | 32/0 | 22.85 | 1 | 1.76E−06 |
| 18 | MSTN_66493737 | T | C | REC | 3/36 | 9/23 | 5.225 | 1 | 0.02226 |
| 18 | MSTN_66494218 | C | A | GENO | 2/14/22 | 6/19/7 | 10.08 | 2 | 0.006487 |
| 18 | MSTN_66494218 | C | A | TREND | 18/58 | 31/33 | 9.708 | 1 | 0.001835 |
| 18 | MSTN_66494218 | C | A | ALLELIC | 18/58 | 31/33 | 9.357 | 1 | 0.002221 |
| 18 | MSTN_66494218 | C | A | DOM | 16/22 | 40019 | 9.288 | 1 | 0.002306 |
| 18 | MSTN_66494218 | C | A | REC | 13181 | 46174 | 3.122 | 1 | 0.07726 |
| 4 | ACN9_40279726 | C | T | GENO | 6/19/13 | 2/13/19 | 4.04 | 2 | 0.1326 |
| 4 | ACN9_40279726 | C | T | TREND | 31/45 | 17/51 | 4.026 | 1 | 0.0448 |
| 4 | ACN9_40279726 | C | T | ALLELIC | 31/45 | 17/51 | 4.026 | 1 | 0.0448 |
| 4 | ACN9_40279726 | C | T | DOM | 25/13 | 15/19 | 3.413 | 1 | 0.06467 |
| 4 | ACN9_40279726 | C | T | REC | 11841 | 11720 | 1.783 | 1 | 0.1817 |
| 22 | PTPN1_38585796 | G | C | GENO | 0/18/22 | 0/7/27 | NA | NA | NA |
| 22 | PTPN1_38585796 | G | C | TREND | 18/62 | 7/61 | 4.896 | 1 | 0.02692 |
| 22 | PTPN1_38585796 | G | C | ALLELIC | 18/62 | 7/61 | 3.901 | 1 | 0.04826 |
| 22 | PTPN1_38585796 | G | C | DOM | 18/22 | 7/27 | 4.896 | 1 | 0.02692 |
| 22 | PTPN1_38585796 | G | C | REC | 0/40 | 0/34 | NA | NA | NA |

TBE Best Race Distance Quantitative Trait Association

| CHR | SNP | STAT | EMP1 | NP |
|---|---|---|---|---|
| 18 | MSTN_66493737 | 36.63 | 1.00E−06 | 1000000 |
| 18 | MSTN_66494218 | 15.97 | 0.000174 | 137586 |
| 22 | COX4I2_22684844 | 6.495 | 0.01146 | 2094 |
| 22 | COX4I2_22684390 | 5.783 | 0.02526 | 949 |
| 22 | PTPN1_38585796 | 4.963 | 0.0377 | 609 |
| 4 | PON1_38697145 | 4.596 | 0.03938 | 583 |
| 22 | PTPN1_38597033 | 4.64 | 0.04406 | 521 |
| 22 | COX4I2_22684676 | 4.51 | 0.04742 | 484 |
| 22 | COX4I2_22683226 | 4.248 | 0.05263 | 436 |
| 4 | ACN9_40279726 | 3.628 | 0.0545 | 421 |

TBE Best Race Distance Means (where distances are furlongs) for significantly associated SNPs

| CHR | SNP | VALUE | G11 | G12 | G22 |
|---|---|---|---|---|---|
| 18 | MSTN_66493737 | GENO | T/T | T/C | C/C |
| 18 | MSTN_66493737 | COUNTS | 12 | 46 | 21 |
| 18 | MSTN_66493737 | FREQ | 0.1519 | 0.5823 | 0.2658 |
| 18 | MSTN_66493737 | MEAN | 10.54 | 9.087 | 6.167 |
| 18 | MSTN_66493737 | SD | 2.742 | 2.365 | 0.8266 |
| 18 | MSTN_66494218 | GENO | C/C | C/A | A/A |
| 18 | MSTN_66494218 | COUNTS | 8 | 39 | 31 |
| 18 | MSTN_66494218 | FREQ | 0.1026 | 0.5 | 0.3974 |
| 18 | MSTN_66494218 | MEAN | 10.56 | 9.179 | 7.403 |
| 18 | MSTN_66494218 | SD | 2.872 | 2.48 | 2.043 |
| 22 | COX4I2_22684844 | GENO | C/C | C/T | T/T |
| 22 | COX4I2_22684844 | COUNTS | 4 | 39 | 40 |
| 22 | COX4I2_22684844 | FREQ | 0.04819 | 0.4699 | 0.4819 |
| 22 | COX4I2_22684844 | MEAN | 11.12 | 8.91 | 7.975 |
| 22 | COX4I2_22684844 | SD | 2.097 | 2.762 | 2.247 |
| 22 | COX4I2_22684390 | GENO | C/C | C/T | T/T |
| 22 | COX4I2_22684390 | COUNTS | 4 | 44 | 32 |
| 22 | COX4I2_22684390 | FREQ | 0.05 | 0.55 | 0.4 |
| 22 | COX4I2_22684390 | MEAN | 10.62 | 8.943 | 7.875 |
| 22 | COX4I2_22684390 | SD | 2.056 | 2.783 | 2.254 |
| 22 | PTPN1_38585796 | GENO | G/G | G/C | C/C |
| 22 | PTPN1_38585796 | COUNTS | 1 | 30 | 50 |
| 22 | PTPN1_38585796 | FREQ | 0.01235 | 0.3704 | 0.6173 |
| 22 | PTPN1_38585796 | MEAN | 8 | 7.75 | 9.09 |
| 22 | PTPN1_38585796 | SD | 0 | 2.176 | 2.736 |
| 4 | PON1_38697145 | GENO | T/T | T/C | C/C |
| 4 | PON1_38697145 | COUNTS | 1 | 11 | 72 |
| 4 | PON1_38697145 | FREQ | 0.0119 | 0.131 | 0.8571 |
| 4 | PON1_38697145 | MEAN | 6 | 10.82 | 8.278 |
| 4 | PON1_38697145 | SD | 0 | 2.892 | 2.359 |
| 22 | PTPN1_38597033 | GENO | T/T | T/C | C/C |
| 22 | PTPN1_38597033 | COUNTS | 2 | 30 | 33 |
| 22 | PTPN1_38597033 | FREQ | 0.03077 | 0.4615 | 0.5077 |
| 22 | PTPN1_38597033 | MEAN | 9.5 | 7.917 | 9.5 |
| 22 | PTPN1_38597033 | SD | 2.121 | 2.275 | 2.339 |

-continued

| | | | | | |
|---|---|---|---|---|---|
| 22 | COX4I2_22684676 | GENO | C/C | C/T | T/T |
| 22 | COX4I2_22684676 | COUNTS | 5 | 46 | 31 |
| 22 | COX4I2_22684676 | FREQ | 0.06098 | 0.561 | 0.378 |
| 22 | COX4I2_22684676 | MEAN | 10.1 | 8.859 | 7.903 |
| 22 | COX4I2_22684676 | SD | 2.133 | 2.75 | 2.286 |
| 22 | COX4I2_22683226 | GENO | T/T | T/G | G/G |
| 22 | COX4I2_22683226 | COUNTS | 5 | 46 | 26 |
| 22 | COX4I2_22683226 | FREQ | 0.06494 | 0.5974 | 0.3377 |
| 22 | COX4I2_22683226 | MEAN | 10.9 | 8.641 | 8.077 |
| 22 | COX4I2_22683226 | SD | 1.884 | 2.491 | 2.331 |
| 4 | ACN9_40279726 | GENO | C/C | C/T | T/T |
| 4 | ACN9_40279726 | COUNTS | 8 | 36 | 35 |
| 4 | ACN9_40279726 | FREQ | 0.1013 | 0.4557 | 0.443 |
| 4 | ACN9_40279726 | MEAN | 7.875 | 8.264 | 9.3 |
| 4 | ACN9_40279726 | SD | 2.1 | 2.628 | 2.544 |

Racing Post Handicap Rating (Best RPR) Quantitative Trait Association

| CHR | SNP | STAT | EMP1 | NP |
|---|---|---|---|---|
| 4 | PDK4_38973231 | 8.095 | 0.005052 | 4750 |
| 4 | PDK4_38969307 | 6.825 | 0.009441 | 2541 |
| 3 | COX4I1_32772871 | 6.748 | 0.009681 | 2478 |

Racing Post Handicap Rating (Best RPR) Means for significantly associated SNPs

| CHR | SNP | STAT | EMP1 | NP |
|---|---|---|---|---|
| 4 | PDK4_38973231 | GENO | A/A | A/G | G/G |
| 4 | PDK4_38973231 | COUNTS | 19 | 46 | 44 |
| 4 | PDK4_38973231 | FREQ | 0.1743 | 0.422 | 0.4037 |
| 4 | PDK4_38973231 | MEAN | 99.95 | 97.7 | 80.3 |
| 4 | PDK4_38973231 | SD | 33.78 | 28.9 | 28.85 |
| 4 | PDK4_38969307 | GENO | A/A | A/C | C/C |
| 4 | PDK4_38969307 | COUNTS | 16 | 42 | 42 |
| 4 | PDK4_38969307 | FREQ | 0.16 | 0.42 | 0.42 |
| 4 | PDK4_38969307 | MEAN | 97.19 | 99.21 | 79.9 |
| 4 | PDK4_38969307 | SD | 36.23 | 28.06 | 28.45 |
| 3 | COX4I1_32772871 | GENO | T/T | T/C | C/C |
| 3 | COX4I1_32772871 | COUNTS | 13 | 42 | 50 |
| 3 | COX4I1_32772871 | FREQ | 0.1238 | 0.4 | 0.4762 |
| 3 | COX4I1_32772871 | MEAN | 100.6 | 99.71 | 83.3 |
| 3 | COX4I1_32772871 | SD | 29.46 | 28.92 | 30.49 |

The invention claimed is:

1. A method of training a Thoroughbred race horse for optimal racing distance, the method comprising the steps of:
   a) identifying a Thoroughbred race horse that is or may become sufficiently developed for race training,
   b) obtaining a biological sample from the horse,
   c) performing a genotypic analysis of a MSTN-66493737 (T/C) SNP in the biological sample from the horse; and
   d) training the horse based on results of the test,
   wherein:
   i) a horse with a C/C genotype in the MSTN-66493737 (T/C) SNP is trained to race as a sprinter,
   ii) a horse with a C/T genotype in the MSTN-66493737 (T/C) SNP is trained to race over middle distances, or
   iii) a horse with a T/T genotype in the MSTN-66493737 (T/C) SNP is trained to race as a stayer.

2. The method of claim 1, wherein the horse has a C/C genotype in the MSTN-66493737 (T/C) SNP and is trained to race as a sprinter.

3. The method of claim 1, wherein the horse has a C/T genotype in the MSTN-66493737 (T/C) SNP and is trained to race over middle distances.

4. The method of claim 1, wherein the horse has a T/T genotype in the MSTN-66493737 (T/C) SNP and is trained to race as a stayer.

5. The method of claim 2 or 3, wherein the horse is a two-year old.

6. The method of claim 4, wherein the horse is a three-year old.

7. A method of breeding a Thoroughbred race horse with elite athletic performance potential, comprising the steps of:
   a) obtaining the result of a genotypic analysis of a MSTN-66493737 (T/C) SNP in a biological sample from a Thoroughbred broodmare;
   b) obtaining the result of a genotypic analysis of a MSTN-66493737 (T/C) SNP in a biological sample from a Thoroughbred stallion; and
   c) mating the broodmare with the stallion to produce a Thoroughbred offspring;
   wherein:
   i) the broodmare and the stallion each have a homozygous C/C genotype in the MSTN-66493737 (T/C) SNP and the offspring has elite sprinting performance potential,
   ii) the broodmare and the stallion each have a homozygous T/T genotype in the MSTN-66493737 (T/C) SNP and the offspring has stamina performance potential,
   iii) one of the broodmare or stallion has a homozygous T/T genotype in the MSTN-66493737 (T/C) SNP and the other horse in the mating pair has a homozygous C/C genotype in the MSTN-66493737 (T/C) SNP and the offspring has middle distance racing performance potential,
   iv) one of the broodmare or stallion has a homozygous C/C genotype in the MSTN-66493737 (T/C) SNP and the other horse in the mating pair has a heterozygous C/T genotype in the MSTN-66493737 (T/C) SNP and the offspring has either elite sprinting performance potential or middle distance racing performance potential,
   v) one of the broodmare or stallion has a homozygous T/T genotype in the MSTN-66493737 (T/C) SNP and the other horse in the mating pair has a heterozygous C/T genotype in the MSTN-66493737 (T/C) SNP and the offspring has either middle distance racing performance potential or stamina performance potential, or
   vi) the broodmare and the stallion each have a heterozygous C/T genotype in the MSTN-66493737 (T/C) SNP and the offspring has elite sprinting performance potential, middle distance racing performance potential, or stamina performance potential.

8. The method of claim 7, wherein the broodmare and the stallion each have a homozygous C/C genotype in the MSTN-66493737 (T/C) SNP and the offspring has elite sprinting performance potential.

9. The method of claim 7, wherein the broodmare and the stallion each have a homozygous T/T genotype in the MSTN-66493737 (T/C) SNP and the offspring has stamina performance potential.

10. The method of claim 7, wherein one of the broodmare or stallion has a homozygous T/T genotype in the MSTN-66493737 (T/C) SNP and the other horse in the mating pair has a homozygous C/C genotype in the MSTN-66493737 (T/C) SNP and the offspring has middle distance racing performance potential.

11. The method of claim 7, wherein one of the broodmare or stallion has a homozygous C/C genotype in the MSTN-66493737 (T/C) SNP and other horse in the mating pair has a heterozygous C/T genotype in the MSTN-66493737 (T/C) SNP and the offspring has either elite sprinting performance potential or middle distance racing performance potential.

12. The method of claim 7, wherein one of the broodmare or stallion has a homozygous T/T genotype in the MSTN-66493737 (T/C) SNP and the other horse in the mating pair has a heterozygous C/T genotype in the MSTN-66493737 T/C) SNP and the offspring has either middle distance racing performance potential or stamina performance potential.

13. The method of claim 7, wherein the broodmare and the stallion each have a heterozygous C/T genotype in the MSTN-66493737 (T/C) SNP and the offspring has elite sprinting performance potential, middle distance racing performance potential, or stamina performance potential.

14. The method of claim 7, further comprising the step of obtaining the genotype of a MSTN-66493737 (T/C) SNP in a biological sample from a foal produced by the mating.

15. A method for detecting the MSTN_66493737 (T/C) single nucleotide polymorphism in an MSTN gene in a horse, comprising: performing a nucleic acid-based assay to analyze a nucleic acid from a biological sample obtained from the horse, and detecting in the assay the C allele of the MSTN_66493737 (T/C) single nucleotide polymorphism.

16. The method of claim 15, wherein performing a nucleic acid-based assay comprises sequencing the nucleic acid.

17. The method of claim 15, wherein performing a nucleic acid-based assay comprises amplifying the nucleic acid.

18. The method of claim 17, wherein the amplifying comprises competitive allele specific PCR.

19. The method of claim 15, wherein the assay is a Taq-Man® single nucleotide polymorphism genotyping assay.

20. The method of claim 15, wherein performing a nucleic acid-based assay comprises hybridizing a probe to the nucleic acid.

21. The method of claim 15, wherein the biological sample is a biological sample which contains genetic material.

22. The method of claim 15, wherein the sample is selected from the group comprising: blood, saliva, skeletal muscle, hair, semen, bone marrow, soft tissue, internal organ, biopsy sample, and skin.

23. The method of claim 15, wherein the nucleic acid is genomic DNA.

24. The method of claim 15, further comprising extracting or releasing DNA from the sample.

25. The method of claim 15, wherein the horse is a Thoroughbred race horse.

* * * * *

SEQUENCE LISTING

<160> NUMBER OF SEQ ID NOS: 43

<210> SEQ ID NO 1
<211> LENGTH: 401
<212> TYPE: DNA
<213> ORGANISM: Equus caballus
<220> FEATURE:
<221> NAME/KEY: misc_feature
<223> OTHER INFORMATION: COX4I2 EquCab2.0 22676361_C/T SNP
<220> FEATURE:
<221> NAME/KEY: variation
<222> LOCATION: (201)..(201)
<223> OTHER INFORMATION: y is c or t

<400> SEQUENCE: 1

```
caagagtgga gtgtgctcca agaactggag gctagcatgt agcagaggag gcagtagcag      60
aggaggagag gttgatgggg gagctgcatt tggagagtct ggcaggcagg accttgaatg     120
ccaggctaag gagtttattg ggaggcaagt gggtgctgat aaaggctcaa ggattccatc     180
aggctgttcc cacaaagacc ygggccacct cagggcacca tatccccata tccaggagcc     240
agttgtgtcc cagagaaaac aagggactgg accttgagac ttggccagtg tccttcacat     300
cctaccctgt gcacgcccct gtttggcctg tggtgcagaa ggcccctggg agacctgaag     360
cagaagctgc agaccattcc aggttagtgt ggagcccag a                          401
```

<210> SEQ ID NO 2
<211> LENGTH: 401
<212> TYPE: DNA
<213> ORGANISM: Equus caballus
<220> FEATURE:
<221> NAME/KEY: misc_feature
<223> OTHER INFORMATION: COX4I2 EquCab 2.0 22684390_C/T SNP
<220> FEATURE:
<221> NAME/KEY: variation
<222> LOCATION: (201)..(201)
<223> OTHER INFORMATION: y is t or c

<400> SEQUENCE: 2

```
gctgggcgat cctggggaca taaaagtgaa tcacctggat ggttcttgcc ctcagggtgc    60
tcccagtcca gtgggggaac caacacaagc ccagataact gtaatatagg atatgtggcg   120
agggtgaagt gtgttcaagg ggctgtgagg acccaaagga gagagagatg aaatcctggt   180
gggccttcca gaggagggca ygttctagtt gaccttgaat ggtgaggctg agggtgctgc   240
caggtggtgg gaacagcatg ggtaagggta tgggagcgga agagcatgga gggtcctagg   300
catcagtaag tgctgtaggg gaaggaacag agagaggcgg tgaggtggcc aggaaagaag   360
ggggcctgac cctggggagc aggagggatg tgtgactcca a                       401
```

<210> SEQ ID NO 3
<211> LENGTH: 401
<212> TYPE: DNA
<213> ORGANISM: Equus caballus
<220> FEATURE:
<221> NAME/KEY: misc_feature
<223> OTHER INFORMATION: CKM EquCab 2.0 15884567_G/A SNP
<220> FEATURE:
<221> NAME/KEY: variation
<222> LOCATION: (48)..(48)
<223> OTHER INFORMATION: r is g or a
<220> FEATURE:
<221> NAME/KEY: variation
<222> LOCATION: (201)..(201)
<223> OTHER INFORMATION: r is g or a

<400> SEQUENCE: 3

```
ctgtccctaa cagacctgga ccttggcccc gtggaggtcc taaaggcrac tatacgcgat    60
gtaaacccaa attcatgaca tcccctgaag catgctcttc ccctgtctgc ccgggtcccc   120
ggaacagcca ccccaagtgc tctctcccaa gtggactctc ccttcacacc ctgcccctcg   180
catccagtgc accggcaagc racactatcc cggtgcccac tccagaaagt caatgtctca   240
ggaatctggg gagccatcag tcaaaattac tatcatacag tatatatagg attcgcatat   300
attcctatgc ataataatta tacgttttgt ggataataaa tatatgtata tatgcataat   360
atttacataa tatatacata tttatataca ttttatacat t                       401
```

<210> SEQ ID NO 4
<211> LENGTH: 401
<212> TYPE: DNA
<213> ORGANISM: Equus caballus
<220> FEATURE:
<221> NAME/KEY: misc_feature
<223> OTHER INFORMATION: PDK4 EquCab 2.0 38973231_A/G SNP
<220> FEATURE:
<221> NAME/KEY: variation
<222> LOCATION: (201)..(201)
<223> OTHER INFORMATION: r is g or a

<400> SEQUENCE: 4

```
actttaaccc tcaactttct aacttaaaat ttatgtttaa ctattccaga gcaatattca    60
```

```
gttttatttg gcaaatgttt tcattttta tagcaaaagt atttagaaat ttttaagaaa    120
gatttcatat ttctttctac ttcattcatt catgtgtggg tagaagtctc gaaagcagca    180
gtaaagacta tggattgaat rtgtgtttca gattgtcatt gtttaatggg tatggaatgc    240
atatatttct tgaatcaatg aacaaaacgc tgtatagtca gcagattagg gtgaggctct    300
ggtgcatatc tgctgcagtg catatcctgg ctctattctc tgaaaatctg ctcttgtggg    360
tcatctaccc tctctaagct tmagcaccct tatttgttaa a                       401
```

<210> SEQ ID NO 5
<211> LENGTH: 23
<212> TYPE: DNA
<213> ORGANISM: Equus caballus
<220> FEATURE:
<221> NAME/KEY: misc_feature
<223> OTHER INFORMATION: MSTN_1 forward primer

<400> SEQUENCE: 5
ataaatgcaa ttgtctcaaa gtc                                            23

<210> SEQ ID NO 6
<211> LENGTH: 21
<212> TYPE: DNA
<213> ORGANISM: Equus caballus
<220> FEATURE:
<221> NAME/KEY: misc_feature
<223> OTHER INFORMATION: MSTN_1 reverse primer

<400> SEQUENCE: 6
ccatatgcaa gtttccattc c                                              21

<210> SEQ ID NO 7
<211> LENGTH: 20
<212> TYPE: DNA
<213> ORGANISM: Equus caballus
<220> FEATURE:
<221> NAME/KEY: misc_feature
<223> OTHER INFORMATION: MSTN_2 forward primer

<400> SEQUENCE: 7
tcagccattc agcctatttg                                                20

<210> SEQ ID NO 8
<211> LENGTH: 20
<212> TYPE: DNA
<213> ORGANISM: Equus caballus
<220> FEATURE:
<221> NAME/KEY: misc_feature
<223> OTHER INFORMATION: MSTN_2 reverse primer

<400> SEQUENCE: 8
acggttggca tttaaccatc                                                20

<210> SEQ ID NO 9
<211> LENGTH: 23
<212> TYPE: DNA
<213> ORGANISM: Equus caballus
<220> FEATURE:
<221> NAME/KEY: misc_feature
<223> OTHER INFORMATION: MSTN_3 forward primer

<400> SEQUENCE: 9
ggagacttgc tttcatttac ctg                                            23

```
<210> SEQ ID NO 10
<211> LENGTH: 20
<212> TYPE: DNA
<213> ORGANISM: Equus caballus
<220> FEATURE:
<221> NAME/KEY: misc_feature
<223> OTHER INFORMATION: MSTN_3 reverse primer

<400> SEQUENCE: 10
gaagcttttg gatgggattg                                                    20

<210> SEQ ID NO 11
<211> LENGTH: 19
<212> TYPE: DNA
<213> ORGANISM: Equus caballus
<220> FEATURE:
<221> NAME/KEY: misc_feature
<223> OTHER INFORMATION: MSTN_4 forward primer

<400> SEQUENCE: 11
ctctggggtt tgcttggtg                                                     19

<210> SEQ ID NO 12
<211> LENGTH: 20
<212> TYPE: DNA
<213> ORGANISM: Equus caballus
<220> FEATURE:
<221> NAME/KEY: misc_feature
<223> OTHER INFORMATION: MSTN_4 reverse primer

<400> SEQUENCE: 12
acctagggaa tggaggatgg                                                    20

<210> SEQ ID NO 13
<211> LENGTH: 20
<212> TYPE: DNA
<213> ORGANISM: Equus caballus
<220> FEATURE:
<221> NAME/KEY: misc_feature
<223> OTHER INFORMATION: MSTN_5 forward primer

<400> SEQUENCE: 13
gaagaggagg gagggaagag                                                    20

<210> SEQ ID NO 14
<211> LENGTH: 22
<212> TYPE: DNA
<213> ORGANISM: Equus caballus
<220> FEATURE:
<221> NAME/KEY: misc_feature
<223> OTHER INFORMATION: MSTN_5 reverse primer

<400> SEQUENCE: 14
ttcagtcttc atgtggtctt gg                                                 22

<210> SEQ ID NO 15
<211> LENGTH: 21
<212> TYPE: DNA
<213> ORGANISM: Equus caballus
<220> FEATURE:
<221> NAME/KEY: misc_feature
<223> OTHER INFORMATION: MSTN_7 forward primer

<400> SEQUENCE: 15
aaggtattgt catctgcttg g                                                  21

<210> SEQ ID NO 16
```

```
<211> LENGTH: 20
<212> TYPE: DNA
<213> ORGANISM: Equus caballus
<220> FEATURE:
<221> NAME/KEY: misc_feature
<223> OTHER INFORMATION: MSTN_7 reverse primer

<400> SEQUENCE: 16
ccaagaccag gagaagatgg                                               20

<210> SEQ ID NO 17
<211> LENGTH: 22
<212> TYPE: DNA
<213> ORGANISM: Equus caballus
<220> FEATURE:
<221> NAME/KEY: misc_feature
<223> OTHER INFORMATION: MSTN_8 forward primer

<400> SEQUENCE: 17
gcttgttagc ataggaaact gg                                            22

<210> SEQ ID NO 18
<211> LENGTH: 20
<212> TYPE: DNA
<213> ORGANISM: Equus caballus
<220> FEATURE:
<221> NAME/KEY: misc_feature
<223> OTHER INFORMATION: MSTN_8 reverse primer

<400> SEQUENCE: 18
ctgagacccg tcaagactcc                                               20

<210> SEQ ID NO 19
<211> LENGTH: 20
<212> TYPE: DNA
<213> ORGANISM: Equus caballus
<220> FEATURE:
<221> NAME/KEY: misc_feature
<223> OTHER INFORMATION: MSTN_9 forward primer

<400> SEQUENCE: 19
cgtctttcat gggtttgatg                                               20

<210> SEQ ID NO 20
<211> LENGTH: 20
<212> TYPE: DNA
<213> ORGANISM: Equus caballus
<220> FEATURE:
<221> NAME/KEY: misc_feature
<223> OTHER INFORMATION: MSTN_9 reverse primer

<400> SEQUENCE: 20
atgttcctcc acggtgtctc                                               20

<210> SEQ ID NO 21
<211> LENGTH: 21
<212> TYPE: DNA
<213> ORGANISM: Equus caballus
<220> FEATURE:
<221> NAME/KEY: misc_feature
<223> OTHER INFORMATION: MSTN_10 forward primer

<400> SEQUENCE: 21
tgaaggaatg aactgtggat g                                             21

<210> SEQ ID NO 22
<211> LENGTH: 20
```

```
<212> TYPE: DNA
<213> ORGANISM: Equus caballus
<220> FEATURE:
<221> NAME/KEY: misc_feature
<223> OTHER INFORMATION: MSTN_10 reverse primer

<400> SEQUENCE: 22
gtctgcgatc ctgctttacc                                               20

<210> SEQ ID NO 23
<211> LENGTH: 21
<212> TYPE: DNA
<213> ORGANISM: Equus caballus
<220> FEATURE:
<221> NAME/KEY: misc_feature
<223> OTHER INFORMATION: MSTN_11 forward primer

<400> SEQUENCE: 23
ttttgaaact gttgtgtcct g                                             21

<210> SEQ ID NO 24
<211> LENGTH: 20
<212> TYPE: DNA
<213> ORGANISM: Equus caballus
<220> FEATURE:
<221> NAME/KEY: misc_feature
<223> OTHER INFORMATION: MSTN_11 reverse primer

<400> SEQUENCE: 24
tcataattgc gtttggttgc                                               20

<210> SEQ ID NO 25
<211> LENGTH: 23
<212> TYPE: DNA
<213> ORGANISM: Equus caballus
<220> FEATURE:
<221> NAME/KEY: misc_feature
<223> OTHER INFORMATION: MSTN_12 forward primer

<400> SEQUENCE: 25
gcaaatgctc aaatgaccta aac                                           23

<210> SEQ ID NO 26
<211> LENGTH: 20
<212> TYPE: DNA
<213> ORGANISM: Equus caballus
<220> FEATURE:
<221> NAME/KEY: misc_feature
<223> OTHER INFORMATION: MSTN_12 reverse primer

<400> SEQUENCE: 26
tgtgctgatt cttgctggtc                                               20

<210> SEQ ID NO 27
<211> LENGTH: 23
<212> TYPE: DNA
<213> ORGANISM: Equus caballus
<220> FEATURE:
<221> NAME/KEY: misc_feature
<223> OTHER INFORMATION: MSTN_13 forward primer

<400> SEQUENCE: 27
tgaagattta gtgttttgtc tcc                                           23

<210> SEQ ID NO 28
<211> LENGTH: 20
<212> TYPE: DNA
```

<210> SEQ ID NO 28
<211> LENGTH: 20
<212> TYPE: DNA
<213> ORGANISM: Equus caballus
<220> FEATURE:
<221> NAME/KEY: misc_feature
<223> OTHER INFORMATION: MSTN_13 reverse primer

<400> SEQUENCE: 28
cgagattcat tgtggagcag                                          20

<210> SEQ ID NO 29
<211> LENGTH: 20
<212> TYPE: DNA
<213> ORGANISM: Equus caballus
<220> FEATURE:
<221> NAME/KEY: misc_feature
<223> OTHER INFORMATION: MSTN_14 forward primer

<400> SEQUENCE: 29
gagacaactt gccacaccag                                          20

<210> SEQ ID NO 30
<211> LENGTH: 22
<212> TYPE: DNA
<213> ORGANISM: Equus caballus
<220> FEATURE:
<221> NAME/KEY: misc_feature
<223> OTHER INFORMATION: MSTN_14 reverse primer

<400> SEQUENCE: 30
tgccctggta ataacaatga ag                                       22

<210> SEQ ID NO 31
<211> LENGTH: 403
<212> TYPE: DNA
<213> ORGANISM: Equus caballus
<220> FEATURE:
<221> NAME/KEY: misc_feature
<223> OTHER INFORMATION: MSTN EquCab2.0 66493737_T/C SNP
<220> FEATURE:
<221> NAME/KEY: variation
<222> LOCATION: (202)..(202)
<223> OTHER INFORMATION: y is t or c

<400> SEQUENCE: 31
agctaagcaa gtaattagca caaaaatttg aatgttatat tcaggctatc tcaaaagtta      60
gaaaatactg tctttagagc caggctgtca ttgtgagcaa aatcactagc aatttctttt     120
attttggttc cccaagattg tttataaata aggtaaatct actccaggac tatttgatag     180
cagagtcata aggaaaaatt ayttggtgca ttataacctg attacttaat aaggagaaca     240
atattttgaa actgttgtgt cctgtttaaa gtagataaag cactgggtaa agcaggatcg     300
cagacacatg gcacagaatc ttccgtgtca tgccttctct gtgaaggtgt ctgtctccct     360
ttccttgagt gtagttatga actgactgca aaaagaatat atg                       403

<210> SEQ ID NO 32
<211> LENGTH: 401
<212> TYPE: DNA
<213> ORGANISM: Equus caballus
<220> FEATURE:
<221> NAME/KEY: misc_feature
<223> OTHER INFORMATION: COX4I1 EquCab2.0 32772871_C/T SNP
<220> FEATURE:
<221> NAME/KEY: variation
<222> LOCATION: (181)..(181)
<223> OTHER INFORMATION: m is a or c
<220> FEATURE:
<221> NAME/KEY: variation
<222> LOCATION: (201)..(201)

<223> OTHER INFORMATION: y is c or t

<400> SEQUENCE: 32

| tcaggtctca | gtcgcaccag | agctggatgg | agccagcgca | gctccatctc | tcagtggctg | 60 |
| ggagtgggct | gcagggtggt | cctcacacaa | gatgggcacc | tccctcctgg | gctccatccc | 120 |
| aggactgttt | cccaggtttg | ggaaactggc | tcgcattagc | cgagtggcgt | gagccggaat | 180 |
| mtgatttact | cacagtgcgc | ygtgcttggt | ggggaacgac | ttccctgctt | tgtacagcac | 240 |
| cctgcgtttc | cagtggtggt | ttgtctggtc | actagtcttt | tatcaagaga | tagtatagtg | 300 |
| aaggttaggt | caaggaaaag | ggaactctga | cttgtcagag | ggctgtttga | actgtatggg | 360 |
| gactgcatct | cgataaccag | gattctgggt | ctccagaccc | a | | 401 |

<210> SEQ ID NO 33
<211> LENGTH: 403
<212> TYPE: DNA
<213> ORGANISM: Equus caballus
<220> FEATURE:
<221> NAME/KEY: misc_feature
<223> OTHER INFORMATION: MSTN EquCab2.0 66493525_T/G SNP
<220> FEATURE:
<221> NAME/KEY: variation
<222> LOCATION: (202)..(202)
<223> OTHER INFORMATION: k is t or g

<400> SEQUENCE: 33

| tggaggaaca | tccacttaga | attctttggg | aatctgagta | gttacactta | ctgagcagct | 60 |
| gtaccaatca | gtctggaaga | aggaacccct | cccccaggcc | tgaattacct | ggggacaaga | 120 |
| cacactgagg | aactaactga | gcctcgggaa | ttaagagaaa | atatagtaca | tctgttatgt | 180 |
| tttggctttg | gaatagcctt | tkaaaggaac | aaagctaagc | aagtaattag | cacaaaaatt | 240 |
| tgaatgttat | attcaggcta | tctcaaaagt | tagaaaatac | tgtctttaga | gccaggctgt | 300 |
| cattgtgagc | aaaatcacta | gcaatttctt | ttattttggt | tccccaagat | tgtttataaa | 360 |
| taaggtaaat | ctactccagg | actatttgat | agcagagtca | taa | | 403 |

<210> SEQ ID NO 34
<211> LENGTH: 403
<212> TYPE: DNA
<213> ORGANISM: Equus caballus
<220> FEATURE:
<221> NAME/KEY: misc_feature
<223> OTHER INFORMATION: MSTN EquCab2.0 66493582_T/G SNP
<220> FEATURE:
<221> NAME/KEY: variation
<222> LOCATION: (202)..(202)
<223> OTHER INFORMATION: k is t or g

<400> SEQUENCE: 34

| gctgtaccaa | tcagtctgga | agaaggaacc | cttcccccag | gcctgaatta | cctggggaca | 60 |
| agacacactg | aggaactaac | tgagcctcgg | gaattaagag | aaaatatagt | acatctgtta | 120 |
| tgttttggct | ttggaatagc | cttttaaagg | aacaaagcta | agcaagtaat | tagcacaaaa | 180 |
| atttgaatgt | tatattcagg | ckatctcaaa | agttagaaaa | tactgtcttt | agagccaggc | 240 |
| tgtcattgtg | agcaaaatca | ctagcaattt | cttttatttt | ggttcccaa | gattgtttat | 300 |
| aaataaggta | aatctactcc | aggactattt | gatagcagag | tcataaagga | aaattatttg | 360 |
| gtgcattata | acctgattac | ttaataagga | gaacaatatt | ttg | | 403 |

<210> SEQ ID NO 35
<211> LENGTH: 403

```
<212> TYPE: DNA
<213> ORGANISM: Equus caballus
<220> FEATURE:
<221> NAME/KEY: misc_feature
<223> OTHER INFORMATION: MSTN EquCab2.0 66493745_A/G SNP
<220> FEATURE:
<221> NAME/KEY: variation
<222> LOCATION: (202)..(202)
<223> OTHER INFORMATION: r is a or g

<400> SEQUENCE: 35
aagtaattag cacaaaaatt tgaatgttat attcaggcta tctcaaaagt tagaaaatac    60
tgtctttaga gccaggctgt cattgtgagc aaaatcacta gcaatttctt ttattttggt   120
tccccaagat tgtttataaa taaggtaaat ctactccagg actatttgat agcagagtca   180
taaaggaaaa ttatttggtg crttataacc tgattactta ataaggagaa caatattttg   240
aaactgttgt gtcctgttta agtagataaa agcactgggt aaagcaggat cgcagacaca   300
tggcacagaa tcttccgtgt catgccttct ctgtgaaggt gtctgtctcc ctttccttga   360
gtgtagttat gaactgactg caaaaagaat atatgaaata tat                    403

<210> SEQ ID NO 36
<211> LENGTH: 403
<212> TYPE: DNA
<213> ORGANISM: Equus caballus
<220> FEATURE:
<221> NAME/KEY: misc_feature
<223> OTHER INFORMATION: MSTN EquCab2.0 66493775_A/G SNP
<220> FEATURE:
<221> NAME/KEY: variation
<222> LOCATION: (202)..(202)
<223> OTHER INFORMATION: r is a or g

<400> SEQUENCE: 36
attcaggcta tctcaaaagt tagaaaatac tgtctttaga gccaggctgt cattgtgagc    60
aaaatcacta gcaatttctt ttattttggt tccccaagat tgtttataaa taaggtaaat   120
ctactccagg actatttgat agcagagtca taaaggaaaa ttatttggtg cattataacc   180
tgattactta ataaggagaa cratattttg aaactgttgt gtcctgttta agtagataa    240 agcactgggt aaagcaggat cgcagacaca tggcacagaa tcttccgtgt catgccttct   300
ctgtgaaggt gtctgtctcc ctttccttga gtgtagttat gaactgactg caaaaagaat   360
atatgaaata tattatcttt cagaagcaat atagatacta cag                    403

<210> SEQ ID NO 37
<211> LENGTH: 403
<212> TYPE: DNA
<213> ORGANISM: Equus caballus
<220> FEATURE:
<221> NAME/KEY: misc_feature
<223> OTHER INFORMATION: MSTN EquCab2.0 66494218_A/C SNP
<220> FEATURE:
<221> NAME/KEY: variation
<222> LOCATION: (202)..(202)
<223> OTHER INFORMATION: m is a or c

<400> SEQUENCE: 37
aggagattat taagcaatgt gcctgcctgg aaatgtgcac cccgggtgct ctcaacaata    60
gtactatggt caaggtgtaa gcaggactct gagctataac ctctttgatt aaaatgttta   120
tttattaggc attttatgat aattagctca tgattatcat tatgctatgt ttacttcatc   180
attttcttta ctaatacatt amattttaaa aaatattttt cctaatctcc agggaataa    240 cttttcaaaat ctaatatgtt aatttgtgaa gaacataaaa acactatgag aaatagtttt   300
```

```
gagtaacaga agtcattttg gtgttcagca aatgctcaaa tgacctaaac gtctacaaat    360
ttcttccttc tctattatta gtgaaaaaaa cttgttatta taa                      403
```

<210> SEQ ID NO 38
<211> LENGTH: 20
<212> TYPE: DNA
<213> ORGANISM: Equus caballus
<220> FEATURE:
<221> NAME/KEY: misc_feature
<223> OTHER INFORMATION: TTN forward primer

<400> SEQUENCE: 38

```
gcatgacaca actggaaagc                                                 20
```

<210> SEQ ID NO 39
<211> LENGTH: 20
<212> TYPE: DNA
<213> ORGANISM: Equus caballus
<220> FEATURE:
<221> NAME/KEY: misc_feature
<223> OTHER INFORMATION: TTN reverse primer

<400> SEQUENCE: 39

```
aactttgccc tcatcaatgc                                                 20
```

<210> SEQ ID NO 40
<211> LENGTH: 20
<212> TYPE: DNA
<213> ORGANISM: Equus caballus
<220> FEATURE:
<221> NAME/KEY: misc_feature
<223> OTHER INFORMATION: MSTN1-2 forward primer

<400> SEQUENCE: 40

```
tgacagcagt gatggctctt                                                 20
```

<210> SEQ ID NO 41
<211> LENGTH: 20
<212> TYPE: DNA
<213> ORGANISM: Equus caballus
<220> FEATURE:
<221> NAME/KEY: misc_feature
<223> OTHER INFORMATION: MSTN1-2 reverse primer

<400> SEQUENCE: 41

```
ttgggttttc cttccacttg                                                 20
```

<210> SEQ ID NO 42
<211> LENGTH: 20
<212> TYPE: DNA
<213> ORGANISM: Equus caballus
<220> FEATURE:
<221> NAME/KEY: misc_feature
<223> OTHER INFORMATION: MSTN2-3 forward primer

<400> SEQUENCE: 42

```
ttcccaagac caggagaaga                                                 20
```

<210> SEQ ID NO 43
<211> LENGTH: 20
<212> TYPE: DNA
<213> ORGANISM: Equus caballus
<220> FEATURE:
<221> NAME/KEY: misc_feature
<223> OTHER INFORMATION: MSTN2-3 reverse primer

```
<400> SEQUENCE: 43
cagcatcgag attctgtgga                                                                    20
```